(12) United States Patent
Larsen et al.

(10) Patent No.: US 9,657,062 B2
(45) Date of Patent: May 23, 2017

(54) GHRELIN ANALOGUES

(71) Applicant: Zealand Pharma A/S, Glostrup (DE)

(72) Inventors: Simon Birksø Larsen, Copenhagen (DK); Ditte Riber, Brønshøj (DK)

(73) Assignee: Zealand Pharma A/S, Glostrup (DK)

( * ) Notice: Subject to any disclaimer, the term of this patent is extended or adjusted under 35 U.S.C. 154(b) by 0 days.

(21) Appl. No.: 14/376,088

(22) PCT Filed: Feb. 1, 2013

(86) PCT No.: PCT/EP2013/052107
§ 371 (c)(1),
(2) Date: Jul. 31, 2014

(87) PCT Pub. No.: WO2013/113916
PCT Pub. Date: Aug. 8, 2013

(65) Prior Publication Data
US 2015/0018518 A1  Jan. 15, 2015

Related U.S. Application Data

(60) Provisional application No. 61/704,393, filed on Sep. 21, 2012, provisional application No. 61/594,970, filed on Feb. 3, 2012.

(51) Int. Cl.
*A61K 38/25* (2006.01)
*C07K 14/60* (2006.01)
*C07K 14/00* (2006.01)
*A61K 38/00* (2006.01)

(52) U.S. Cl.
CPC ............ *C07K 14/001* (2013.01); *C07K 14/60* (2013.01); *A61K 38/00* (2013.01)

(58) Field of Classification Search
None
See application file for complete search history.

(56) References Cited

U.S. PATENT DOCUMENTS

2009/0275511 A1*  11/2009  Dong ............................. 514/12

FOREIGN PATENT DOCUMENTS

| EP | 1506786 A1 | 2/2005 |
|---|---|---|
| EP | 1524274 A1 | 4/2005 |
| JP | 2006-515271 A | 5/2006 |
| JP | 2009-510088 A | 3/2009 |
| JP | 2010-504966 A | 2/2010 |
| WO | WO-2004/009616 A2 | 1/2004 |
| WO | WO-2005/026392 A2 | 3/2005 |
| WO | WO-2006/058539 A2 | 6/2006 |
| WO | WO-2007/038678 A2 | 4/2007 |
| WO | WO-2007/041278 A2 | 4/2007 |
| WO | WO-2008/039415 A2 | 4/2008 |

OTHER PUBLICATIONS

Braga et al., "Making Crystals from Crystals: a green route to crystal engineering and polymorphism," Chem. Commun., 2005, pp. 3635-3645.*
Seddon, K.R., "Pseudopolymorph: a polemic," Crystal Growth & Design, 2004, 4(6), pp. 1087, web release date Oct. 19, 2004.*
Vippagunta et al. "Crystalline Solids," Advanced Drug Delivery Reviews, 2001, 48, pp. 3-26.*
Katugampola et al., "[125I -His9]-ghrelin, a novel radioligand for localizing GHS orphan receptors in human and rat tissue; up-regulation of receptors with atherosclerosis," Brit. J. Pharmacol. 134:143-149 (2001).*
De Smet et al., "Endogenous and exogenous ghrelin enhance the colonic and gastric manifestations of dextran sodium sulphate-induced colitis in mice," Neurogastroenterol. Motil. 21:59-70 (2009).*
WHO Cardiovascular guidelines "Prevention of Cardiovascular Disease: Guidelines for assessment and management of cardiovascular risk" accessed at Mar. 16, 2015 at URL who.intJcardiovascular_diseases/guidelines/Full%20text.pdf.*
Compston, et al. "Mutliple Sclerosis," The Lancet 359:1221-1231 (2002).*
Magiera et al., "Serum ghrelin in female patients with rheumatoid arthritis during treatment with infliximab," Rheumtaol Int 33:1611-1613 (2013).*
Masayasu et al., "Ghrelin: structure and function," Physiol Rev. 85(2):495-522 (2005).
International Search Report and Written Opinion for International Patent Application No. PCT/EP2013/052107, mailed Oct. 1, 2013 (20 pages).
DeBoer, "Use of ghrelin as a treatment for inflammatory bowel disease: mechanistic considerations," Int J Pept. 2011:189242 (2011) (8 pages).
Gonzalez-Rey et al., "Therapeutic action of ghrelin in a mouse model of colitis," Gastroenterology. 130(6):1707-20 (2006).
Wu et al., "Orexigenic hormone ghrelin attenuates local and remote organ injury after intestinal ischemia-reperfusion," PLoS One. 3(4):e2026 (2008) (8 pages).
Wu et al., "Orexigenic hormone ghrelin ameliorates gut barrier dysfunction in sepsis in rats," Crit Care Med. 37(8):2421-6 (2009) (18 pages).
Cheng et al., "Ghrelin ameliorates intestinal barrier dysfunction in experimental colitis by inhibiting the activation of nuclear factor-kappa B," Biochem Biophys Res Commun. 458(1):140-7 (2015).
Konturek et al., "Ghrelin ameliorates colonic inflammation. Role of nitric oxide and sensory nerves," J Physiol Pharmacol. 60(2):41-7 (2009).
Morley et al., "Cachexia: pathophysiology and clinical relevance," Am J Clin Nutr. 83(4):735-43 (2006).
Hillman, "Ghrelin Biology and Its Role in Weight-related Disorders," <http://www.discoverymedicine.com/Jennifer-B-Hillman/2011/06/17/ghrelin-biology-and-its-role-in-weight-related-disorders/>, retrieved on Feb. 17, 2016 (7 pages).

* cited by examiner

*Primary Examiner* — Julie Ha
*Assistant Examiner* — Kristina M Hellman
(74) *Attorney, Agent, or Firm* — Clark & Elbing LLP; Kristina Bicker-Brady

(57) ABSTRACT

The present invention relates, inter alia, to ghrelin analogs and their medical use, for example in the treatment of cachexia, chronic obstructive pulmonary disease, gastrointestinal disorders (e.g., gastroparesis and/or inflammatory disorders such as colitis, gut barrier dysfunction, and ischemia reperfusion injury), loss of body weight, and decreased appetite.

16 Claims, 2 Drawing Sheets

GHRELIN ANALOGUES

CROSS-REFERENCE TO RELATED APPLICATIONS

This application is the U.S. National Stage of the International Patent Application No. PCT/EP2013/052107, filed Feb. 1, 2013, which claims the benefit of U.S. Provisional Application No. 61/704,393, filed Sep. 21, 2012, and U.S. Provisional Application No. 61/594,970, filed Feb. 3, 2012, each of which is incorporated herein by reference.

FIELD OF THE INVENTION

The present invention relates, inter alia, to ghrelin analogues and their medical use, for example in the treatment of a condition caused or characterized by loss of body weight or decreased appetite, e.g. the treatment and/or prevention of cachexia, effects of gastrectomy or vagectomy, anorexia or bulimia, chronic obstructive pulmonary disease, and gastro-intestinal disorders (e.g., gastroparesis and/or inflammatory disorders such as colitis, gut barrier dysfunction, and ischemia reperfusion injury), in an individual in need thereof.

BACKGROUND OF THE INVENTION

Cachexia is a wasting syndrome characterized by physical wasting associated with loss of weight and muscle mass. These symptoms leave individuals affected by the syndrome extremely weak and unable to perform everyday tasks. Cachexia often is associated with diseases such as cancer, AIDS, and cardiovascular disease. According to the National Cancer Institute, almost one-third of cancer deaths may be caused by cachexia. Despite this remarkable statistic, there currently appear to be no effective treatments for cachexia.

A number of hormones that influence satiety, gastrointestinal motility, and blood glucose levels are secreted in the gastrointestinal tract. One of these hormones is ghrelin.

The peptide ghrelin was identified as the ligand of the growth-hormone secretagogue receptor type 1a (GHSR1a), and plays an important role in a number of biological systems, such as the release of growth hormone, the release of insulin, the stimulation of appetite, and gastric motility. Ghrelin is a 28 amino acid peptide hormone with its third residue (Ser3) modified with an octanoyl acid moiety. This latter modification appears to be important for ghrelin's interaction with GHSR1a, and, thus, its activity. Ghrelin is formed by the cleavage of preproghrelin, which produces at least two distinct peptides, ghrelin and obestatin.

SUMMARY OF THE INVENTION

The invention provides a compound of the formula I:

$$R^1-Z-R^2 \quad (I)$$

wherein
$R^1$ is hydrogen, $C_{1-4}$ alkyl, formyl, acetyl, trifluoroacetyl or benzoyl;
$R^2$ is OH or $NH_2$; and
Z is an amino acid sequence having the formula Ia:

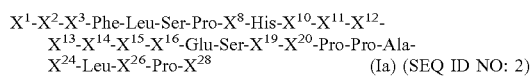
(Ia) (SEQ ID NO: 2)

or is a truncated form thereof lacking from 1 to 23 amino acids from the C-terminus;

wherein
$X^1$ is an amino acid residue selected from Ala, Inp, Pro, DPro, Sar, Aib, Phe and Ser;
$X^2$ is Ser; or
$X^1$ and $X^2$ together constitute a residue of a non-naturally occurring amino acid, wherein the shortest bond separation between the amino nitrogen atom and the carbon atom of the carbonyl group in the non-naturally occurring amino acid is 3 to 7 bonds;
when $X^1$ is an amino acid residue selected from Pro, DPro, Phe and Ser, or when $X^1$ and $X^2$ together constitute a residue of the non-naturally occurring amino acid, then $X^3$ is selected among:

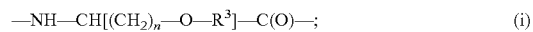 (i)

 (ii)

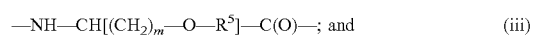 (iii)

 (iv)

and when $X^1$ is an amino acid residue selected from Ala, Sar, Inp and Aib, then $X^3$ is selected among:

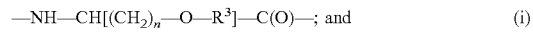 (i)

 (ii)

wherein
$R^3$ and $R^4$ are, independently, $C_{1-35}$-alkyl or -alkenyl groups;
$R^5$ and $R^6$ are, independently, $C_{1-35}$-acyl groups; and
n, m and p are integers 1, 2, 3, 4 or 5;
when present
$X^8$ is selected from Glu, Lys and Tyr;
$X^{10}$ is selected from Gln, Glu and Ser;
$X^{11}$ is selected from Arg, Lys and Ser;
$X^{12}$ is selected from Val, Ala, Pro, Lys, Thr and Leu;
$X^{13}$ is selected from Gln and Ser;
$X^{14}$ is selected from Gln, Lys, Tyr and Ser, or is absent;
$X^{15}$ is selected from Arg and Ser;
$X^{16}$ is selected from Lys, Ser and Pro;
$X^{19}$ is selected from Lys and Ser;
$X^{20}$ is selected from Lys, Glu and Ser;
$X^{24}$ is selected from Lys, Tyr and Ser;
$X^{26}$ is selected from Gln and Ser; and
$X^{28}$ is selected from Arg and Ser;
and, optionally, one or more of said amino acid residues $X^8$, $X^{10}$, $X^{11}$, $X^{13}$, $X^{14}$, $X^{16}$, $X^{19}$, $X^{20}$, $X^{24}$, $X^{26}$ and $X^{28}$, independently, is replaced with a modified lysine residue comprising a lipophilic substituent having the formula $Z^1Z^2$—, wherein $Z^2$ is a spacer moiety or is absent, and $Z^1$ is a lipophilic moiety conjugated, either via $Z^2$ or directly, to the side-chain of said lysine residue;
or a pharmaceutically acceptable salt or solvate of any of the above.

In some embodiments, the present invention provides a compound comprising the formula I:

$$R^1-Z-R^2 \quad (I)$$

wherein
$R^1$ is hydrogen, $C_{1-4}$ alkyl, formyl, acetyl, trifluoroacetyl or benzoyl;
$R^2$ is OH or $NH_2$; and
Z is an amino acid sequence having the formula Ia:

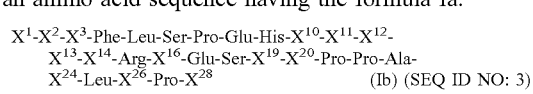
(Ib) (SEQ ID NO: 3)

or is a truncated form thereof lacking from 1 to 23 amino acids from the C-terminus;

wherein
$X^1$ is an amino acid residue selected from Ala, Inp, Pro, DPro, Sar, Aib, Phe and Ser;
$X^2$ is Ser; or
$X^1$ and $X^2$ together constitute a residue of a non-naturally occurring amino acid, wherein the shortest bond separation between the amino nitrogen atom and the carbon atom of the carbonyl group in the non-naturally occurring amino acid is 3 to 7 bonds;
when $X^1$ is an amino acid residue selected from Pro, DPro, Phe and Ser, or when $X^1$ and $X^2$ together constitute a residue of the non-naturally occurring amino acid, then $X^3$ is selected among:

$$-NH-CH[(CH_2)_n-O-R^3]-C(O)-;\quad\text{(i)}$$

$$-NH-CH(R^4)-C(O)-;\quad\text{(ii)}$$

$$-NH-CH[(CH_2)_m-O-R^5]-C(O)-;\text{ and}\quad\text{(iii)}$$

$$-NH-CH[(CH_2)_p-NH-R^6]-C(O)-;\quad\text{(iv)}$$

and when $X^1$ is an amino acid residue selected from Ala, Sar, Inp and Aib, then $X^3$ is selected among:

$$-NH-CH[(CH_2)_n-O-R^3]-C(O)-;\text{ and}\quad\text{(i)}$$

$$-NH-CH(R^4)-C(O)-;\quad\text{(ii)}$$

wherein
$R^3$ and $R^4$ are, independently, $C_{1-35}$-alkyl or -alkenyl groups;
$R^5$ and $R^6$ are, independently, $C_{1-35}$-acyl groups; and
n, m and p are integers 1, 2, 3, 4 or 5;
when present
$X^{10}$ is selected from Gln and Ser;
$X^{11}$ is selected from Arg and Lys;
$X^{12}$ is selected from Val, Ala, Thr and Leu;
$X^{13}$ is selected from Gln and Ser;
$X^{14}$ is selected from Gln and Ser, or is absent;
$X^{16}$ is Lys;
$X^{19}$ is Lys;
$X^{20}$ is Lys;
$X^{24}$ is Lys; and
$X^{26}$ is selected from Gln and Ser;
$X^{28}$ is Arg;
and, optionally, one or more of said amino acid residues $X^{10}$, $X^{11}$, $X^{13}$, $X^{14}$, $X^{16}$, $X^{19}$, $X^{20}$, $X^{24}$, $X^{26}$ and $X^{28}$, independently, is replaced with a modified lysine residue comprising a lipophilic substituent having the formula $Z^1Z^2-$, wherein $Z^2$ is a spacer moiety or is absent, and $Z^1$ is a lipophilic moiety conjugated, either via $Z^2$ or directly, to the side-chain of said lysine residue;
or a pharmaceutically acceptable salt or solvate of any of the above.

In some embodiments, the present invention provides a compound comprising the formula I:

$$R^1-Z-R^2\quad\text{(I)}$$

wherein
$R^1$ is hydrogen, $C_{1-4}$ alkyl, formyl, acetyl, trifluoroacetyl or benzoyl;
$R^2$ is OH or $NH_2$; and
Z is an amino acid sequence having the formula Ia:

$$X^1\text{-}X^2\text{-}X^3\text{-Phe-Leu-Ser-Pro-Glu-His-}X^{10}\text{-}X^{11}\text{-}X^{12}\text{-}$$
$$X^{13}\text{-}X^{14}\text{-Arg-}X^{16}\text{-Glu-Ser-}X^{19}\text{-}X^{20}\text{-Pro-Pro-Ala-}$$
$$X^{24}\text{-Leu-}X^{26}\text{-Pro-}X^{28}\quad\text{(Ib) (SEQ ID NO: 3)}$$

or is a truncated form thereof lacking from 1 to 23 amino acids from the C-terminus;

wherein
$X^1$ is an amino acid residue selected from Ala, Inp, Pro, DPro, Sar, Aib, Phe and Ser;
$X^2$ is Ser; or
$X^1$ and $X^2$ together constitute a residue of a non-naturally occurring amino acid, wherein the shortest bond separation between the amino nitrogen atom and the carbon atom of the carbonyl group in the non-naturally occurring amino acid is 3 to 7 bonds;
when $X^1$ is an amino acid residue selected from Pro, DPro, Phe and Ser, or when $X^1$ and $X^2$ together constitute a residue of the non-naturally occurring amino acid, then $X^3$ is selected from among:

$$-NH-CH[(CH_2)_n-O-R^3]-C(O)-;\quad\text{(i)}$$

$$-NH-CH(R^4)-C(O)-;\quad\text{(ii)}$$

$$-NH-CH[(CH_2)_m-O-R^5]-C(O)-;\text{ and}\quad\text{(iii)}$$

$$-NH-CH[(CH_2)_p-NH-R^6]-C(O)-;\quad\text{(iv)}$$

and when $X^1$ is an amino acid residue selected from Ala, Sar, Inp and Aib, then $X^3$ is selected from among:

$$-NH-CH[(CH_2)_n-O-R^3]-C(O)-;\text{ and}\quad\text{(i)}$$

$$-NH-CH(R^4)-C(O)-;\quad\text{(ii)}$$

wherein
$R^3$ and $R^4$ are, independently, $C_{1-35}$-alkyl or -alkenyl groups;
$R^5$ and $R^6$ are, independently, $C_{1-35}$-acyl groups; and
n, m and p are integers 1, 2, 3, 4 or 5;
when present
$X^{10}$ is Gln;
$X^{11}$ is selected from Arg and Lys;
$X^{12}$ is selected from Val, Ala, Thr and Leu;
$X^{13}$ is Gln;
$X^{14}$ is Gln or is absent;
$X^{16}$ is Lys;
$X^{19}$ is Lys;
$X^{20}$ is Lys;
$X^{24}$ is Lys; and
$X^{26}$ is Gln;
$X^{28}$ is Arg;
and optionally, wherein one or more of said amino acid residues $X^{10}$, $X^{11}$, $X^{13}$, $X^{14}$, $X^{16}$, $X^{19}$, $X^{20}$, $X^{24}$, $X^{26}$ and $X^{28}$ independently, is replaced with a modified lysine residue comprising a lipophilic substituent having the formula $Z^1Z^2-$, wherein $Z^2$ is a spacer moiety or is absent, and $Z^1$ is a lipophilic moiety conjugated, either via $Z^2$ or directly, to the side-chain of said lysine residue;
or a pharmaceutically acceptable salt or solvate of any of the above.

In some embodiments $X^{28}$ is not one of the residues which may be replaced by the modified lysine residue.

In any of the above formulae, it may be desirable that $X^1$ is Pro and $X^3$ is selected from $$-NH-CH[(CH_2)_n-O-R^3]-C(O)-;\text{ and}\quad\text{(i)}$$

$$-NH-CH[(CH_2)_p-NH-R^6]-C(O)-.\quad\text{(iv)}$$

Thus the invention further provides a compound comprising the formula I:

$$\text{(I)}\quad R^1-Z-R^2$$

wherein
R$^1$ is hydrogen, C$_{1-4}$ alkyl, formyl, acetyl, trifluoroacetyl or benzoyl;
R$^2$ is OH or NH$_2$; and
Z is an amino acid sequence having the formula Ic:

Pro-Ser-X$^3$-Phe-Leu-Ser-Pro-Glu-His-X$^{10}$-X$^{11}$-X$^{12}$-X$^{13}$-X$^{14}$-Arg-X$^{16}$-Glu-Ser-X$^{19}$-X$^{20}$-Pro-Pro-Ala-X$^{24}$-Leu-X$^{26}$-Pro-X$^{28}$ (Ic) (SEQ ID NO: 4)

or is a truncated form thereof lacking from 1 to 23 amino acids from the C-terminus;
wherein
X$^3$ is selected from among:

—NH—CH[(CH$_2$)$_n$—O—R$^3$]—C(O)—; and (i)

—NH—CH[(CH$_2$)$_p$—NH—R$^6$]—C(O)—; (iv)

wherein
R$^3$ is a C$_{1-35}$-alkyl or -alkenyl group;
R$^6$ is a C$_{1-35}$-acyl group; and
n and p are integers 1, 2, 3, 4 or 5;
when present
X$^{10}$ is selected from Gln and Ser;
X$^{11}$ is selected from Arg and Lys;
X$^{12}$ is selected from Val, Ala, Thr and Leu;
X$^{13}$ is selected from Gln and Ser;
X$^{14}$ is selected from Gln and Ser, or is absent;
X$^{16}$ is Lys;
X$^{19}$ is Lys;
X$^{20}$ is Lys;
X$^{24}$ is Lys; and
X$^{26}$ is selected from Gln and Ser;
X$^{28}$ is Arg;
and optionally, wherein one or more of said amino acid residues X$^{10}$, X$^{11}$, X$^{13}$, X$^{14}$, X$^{16}$, X$^{19}$, X$^{20}$, X$^{24}$, X$^{26}$ and X$^{28}$ independently, is replaced with a modified lysine residue comprising a lipophilic substituent having the formula Z$^1$Z$^2$—, wherein Z$^2$ is a spacer moiety or is absent, and Z$^1$ is a lipophilic moiety conjugated, either via Z$^2$ or directly, to the side-chain of said lysine residue;
or a pharmaceutically acceptable salt or solvate of any of the above In certain embodiments, X$^3$ is —NH—CH[(CH$_2$)$_n$—O—R$^3$]—C(O)— (where n and R$^3$ are as defined above), X$^{12}$ is Val and X$^{20}$ is Ser.

Thus the compound may have the formula I:

R$^1$—Z—R$^2$ (I)

wherein
R$^1$ is hydrogen, C$_{1-4}$ alkyl, formyl, acetyl, trifluoroacetyl or benzoyl;
R$^2$ is OH or NH$_2$; and
Z is an amino acid sequence having the formula Id:

Pro-Ser-X$^3$-Phe-Leu-Ser-Pro-Glu-His-X$^{10}$-X$^{11}$-Val-X$^{13}$-X$^{14}$-Arg-X$^{16}$-Glu-Ser-X$^{19}$-Ser-Pro-Pro-Ala-X$^{24}$-Leu-X$^{26}$-Pro-X$^{28}$ (Id) (SEQ ID NO: 5)

or is a truncated form thereof lacking from 1 to 23 amino acids from the C-terminus;
wherein
X$^3$ is —NH—CH[(CH$_2$)$_n$—O—R$^3$]—C(O)—
wherein
R$^3$ is a C$_{1-35}$-alkyl or -alkenyl group and n is an integer 1, 2, 3, 4 or 5;
when present
X$^{10}$ is selected from Gln and Ser;
X$^{11}$ is selected from Arg and Lys;
X$^{13}$ is selected from Gln and Ser;
X$^{14}$ is selected from Gln and Ser, or is absent;
X$^{16}$ is Lys;
X$^{19}$ is Lys;
X$^{24}$ is Lys; and
X$^{26}$ is selected from Gln and Ser;
X$^{28}$ is Arg;
and optionally, wherein one or more of said amino acid residues X$^{10}$, X$^{11}$, X$^{13}$, X$^{14}$, X$^{16}$, X$^{19}$, X$^{24}$, X$^{26}$ and X$^{28}$ independently, is replaced with a modified lysine residue comprising a lipophilic substituent having the formula Z$^1$Z$^2$—, wherein Z$^2$ is a spacer moiety or is absent, and Z$^1$ is a lipophilic moiety conjugated, either via Z$^2$ or directly, to the side-chain of said lysine residue;
or a pharmaceutically acceptable salt or solvate of any of the above.

In alternative embodiments, X$^3$ is —NH—CH[(CH$_2$)$_p$—NH—R$^6$]—C(O)—, X$^{12}$ is Val and X20 is Ser.

Thus the compound may have the formula I:

R$^1$—Z—R$^2$ (I)

wherein
R$^1$ is hydrogen, C$_{1-4}$ alkyl, formyl, acetyl, trifluoroacetyl or benzoyl;
R$^2$ is OH or NH$_2$; and
Z is an amino acid sequence having the formula Id:

Pro-Ser-X$^3$-Phe-Leu-Ser-Pro-Glu-His-X$^{10}$-X$^{11}$-Val-X$^{13}$-X$^{14}$-Arg-X$^{16}$-Glu-Ser-X$^{19}$-Ser-Pro-Pro-Ala-X$^{24}$-Leu-X$^{26}$-Pro-X$^{28}$ (Id) (SEQ ID NO: 5)

or is a truncated form thereof lacking from 1 to 23 amino acids from the C-terminus;
wherein
X$^3$—NH—CH[(CH$_2$)$_p$—NH—R$^6$]—C(O)—
wherein
R$^6$ is a C$_{1-35}$-acyl group and p is an integer 1, 2, 3, 4 or 5;
when present
X$^{10}$ is selected from Gln, Glu and Ser;
X$^{11}$ is selected from Arg and Lys;
X$^{13}$ is selected from Gln and Ser;
X$^{14}$ is selected from Gln and Ser, or is absent;
X$^{16}$ is Lys;
X$^{19}$ is Lys;
X$^{24}$ is Lys; and
X$^{26}$ is selected from Gln and Ser;
X$^{28}$ is Arg;
and optionally, wherein one or more of said amino acid residues X$^{10}$, X$^{11}$, X$^{13}$, X$^{14}$, X$^{16}$, X$^{19}$, X$^{24}$, X$^{26}$ and X$^{28}$ independently, is replaced with a modified lysine residue comprising a lipophilic substituent having the formula Z$^1$Z$^2$—, wherein Z$^2$ is a spacer moiety or is absent, and Z$^1$ is a lipophilic moiety conjugated, either via Z$^2$ or directly, to the side-chain of said lysine residue;
or a pharmaceutically acceptable salt or solvate of any of the above.

In some embodiments X$^{28}$ is not one of the residues which may be replaced by the modified lysine residue.

Further aspects of the present invention include, but are not limited to, a compound, or a pharmaceutically acceptable salt or solvate thereof, of the invention for use in therapy (e.g., in treatment of any of the diseases, disorders, conditions, or syndromes described herein).

Further aspects of the present invention include, but are not limited to, a pharmaceutical composition comprising a compound, or a pharmaceutically acceptable salt or solvate thereof, of the invention and a pharmaceutically acceptable carrier.

Further aspects of the present invention include, but are not limited to, a method of treating any of the diseases, disorders, conditions, or syndromes described herein in a subject in need thereof, the method comprising administering a therapeutically effective amount of a compound, or a pharmaceutically acceptable salt or solvate thereof, of the invention, or a pharmaceutical composition of the invention to the subject.

Further aspects of the present invention include, but are not limited to, use of a compound, or a pharmaceutically acceptable salt or solvate thereof, of the invention, or a pharmaceutical composition of the invention, in the manufacture of a medicament for use in therapy (e.g. in treatment of any of the diseases, disorders, conditions, or syndromes described herein).

Further aspects of the present invention include, but are not limited to, a nucleic acid molecule (which may comprise DNA, RNA, or a mixture thereof) encoding a compound (peptide) of the invention.

Further aspects of the present invention include, but are not limited to, an expression vector comprising such a nucleic acid molecule of the invention.

Further aspects of the present invention include, but are not limited to, a host cell containing such a nucleic acid construct or expression vector of the invention.

DETAILED DESCRIPTION OF THE INVENTION

Figure 1:
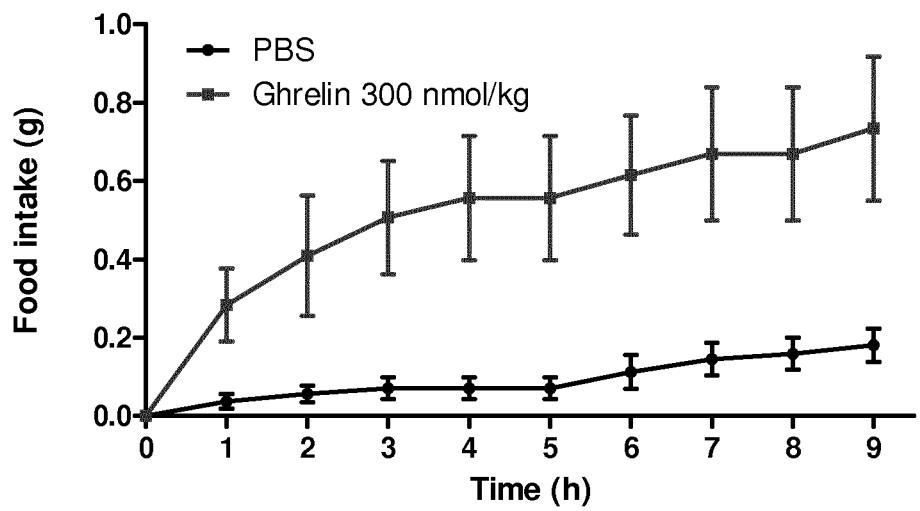
FIG. 1: Effects of ghrelin or vehicle administration early in the light phase on food intake in normal mice. (A) Food intake when animals had free access to food directly after administration; (B) food intake when animals had access to food 2 hours after administration.
Figure 1:
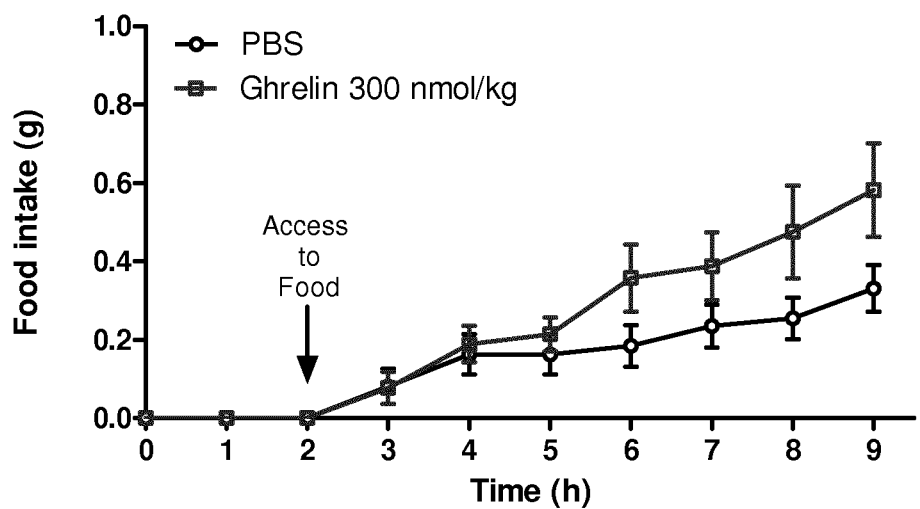

Throughout the present specification, the conventional one-letter and three-letter codes for residues of naturally occurring amino acids are used. Unless otherwise indicated, reference is made to the L-isomeric forms of the amino acids in question. Where appropriate, the D-isomeric form of an amino acid is indicated in the conventional manner by the prefix "D" before the conventional three-letter code (e.g. DPro). Frequently employed three- or four-letter codes are employed for residues of a number of less common or non-naturally occurring amino acids, including Orn (ornithine, i.e. 2,5-diaminopentanoic acid), Dbu (2,4-diaminobutyric acid), Gaba (gamma-aminobutyric acid), Sar (sarcosine, i.e. N-methylglycine), Aib (α-aminoisobutyric acid), Bal (β-alanine, i.e. 3-aminopropanoic acid, also referred to as β-ala), Dap (2,3-diaminopropanoic acid, also referred to as Dpr), Inp (isonipecotic acid, i.e. 4-carboxypiperidine), IPro (i.e. pyrrolidine-3-carboxylic acid), cACC (cis-4-aminocyclohexane carboxylic acid), tACC (trans-4-aminocyclohexane carboxylic acid), Mamb (3-aminomethyl-benzoic acid) and Cmp (4-carboxymethyl-piperidine).

Unless otherwise indicated, the term "ghrelin" refers to native human ghrelin having the sequence H-Gly-Ser-Ser(O-octanoyl)-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-OH (SEQ ID NO: 1).

In the latter sequence, the abbreviation Ser(O-octanoyl) for the residue in position 3 designates a modified (acylated) serine residue in which the hydrogen atom of the side-chain hydroxy group in serine is replaced by an n-octanoyl group.

Among sequences disclosed herein are sequences (including SEQ ID NO: 1, above) incorporating an "H—" moiety at the amino terminus (N-terminus) of the sequence, and either an "—OH" moiety or an "—NH$_2$" moiety at the carboxy terminus (C-terminus) of the sequence. In such cases, and unless otherwise indicated, an "H—" moiety at the N-terminus of the sequence in question indicates a hydrogen atom [i.e. $R^1$=H in formula I; corresponding to the presence of a free primary or secondary amino group at the N-terminus], while an "—OH" (as in SEQ ID NO: 1, above) or an "—NH$_2$" moiety at the C-terminus of the sequence indicates a hydroxy group [i.e. $R^2$=OH; corresponding to the presence of a carboxy (COOH) group at the C-terminus] or an amino group [i.e. $R^2$=NH$_2$; corresponding to the presence of an amido (CONH$_2$) group at the C-terminus], respectively. In each sequence of the invention, a C-terminal "—OH" moiety may be substituted for a C-terminal "—NH$_2$" moiety, and vice-versa.

Compounds (ghrelin analogues) of the invention exhibit agonist activity at the human ghrelin receptor, i.e. the growth hormone secretagogue receptor type 1a (GHSR1a) having the sequence encoded by the sequence with accession number AY429112.1 (GI:38016896) (SEQ ID NO: 6). Activity may be determined by measuring $Ca^{2+}$ signalling in cells expressing the ghrelin receptor. The cells are preferably mammalian cells. They may be human cells, such as HEK293 cells, or non-human mammalian cells e.g. rodent cells. In certain embodiments the cells do not express an endogenous ghrelin receptor and have been transfected with nucleic acid encoding the human ghrelin receptor such that they express the human ghrelin receptor. The agonist activity of a given compound may be quantified by determining an $EC_{50}$ value for the compound. A suitable assay may be performed at a concentration of 20000 cells per 100 µl medium, e.g. in standard 96 well tissue culture plates, or more specifically may be performed under the conditions described in Example 3 below.

The compound of the invention may have greater agonist activity at the ghrelin receptor than human ghrelin (including the octanoyl moiety at Ser3, i.e. compound 1 described in the examples). For example, the compound may have a lower $EC_{50}$ than human ghrelin when determined under identical conditions, e.g. the conditions mentioned above. Data for in vitro activation of the human GHSR1a receptor [expressed as an $EC_{50}$ value, i.e. the concentration at which the test compound in question exhibits 50% of its maximal activity, as determined by a ghrelin receptor functional assay as described herein (vide infra)] by more than 60 widely representative compounds of the invention are shown in Table 1 (vide infra).

Under the conditions described in Example 3, compounds of the invention will then typically exhibit $EC_{50}$ values of ≤40 nM, such as ≤30 nM, for example ≤20 nM, e.g. ≤10 nM, and numerous compounds of the invention exhibit $EC_{50}$ values of ≤5 nM. Some compounds of the invention exhibit $EC_{50}$ values of, ≤1 nM, such as ≤0.5 nM, or ≤0.3 nM.

The compounds of the invention may be capable of modulating (e.g. increasing) food intake in mammals, such as: primates including humans, great apes (e.g. gorillas, chimpanzees, orangutans), old world monkeys, new world monkeys; rodents (e.g. mice, rats, guinea pigs, hamsters); cats; dogs; lagomorphs (including rabbits); cows; sheep; goats; horses; pigs; or any other livestock, agricultural, laboratory or domestic mammals. Preferably they have activity in humans.

For example, the compounds may increase aggregate food intake in a subject as compared to an equivalent untreated subject. They may increase aggregate food intake in a subject as compared to an equivalent subject equivalently treated with human ghrelin (including the octanoyl moiety at Ser3, i.e. compound 1 described in the examples), e.g. a subject treated with the same dose (w/w) of human ghrelin in the same dosing pattern.

In either instance, aggregate food may be increased over a period of 1 hour, 2 hours, 3 hours, 4 hours, 5 hours, 6 hours, 10 hours, 12 hours or 24 hours after administration.

Aggregate food intake compared to untreated subjects, or compared to subjects treated with human ghrelin, may be increased by at least 10%, 20%, 30%, 40%, 50%, 60%, 70%, 80%, 90%, 100% or even more over the respective period.

The compounds may be capable of exerting their effect on food intake when the subjects are provided with access to food at the same time as administration of the compound. Additionally or alternatively, the compounds may be capable of exerting their effect on food intake when the subjects are provided with access to food only after administration of the compound, e.g. 15 minutes, 30 minutes, 45 minutes, 1 hour, 2 hours, 3 hours, or even longer, after administration of the compound. In certain embodiments the compounds are capable of increasing food intake when the subjects are provided with access to food only 2 hours after administration of the compound.

The effect of the compounds may be measured in any suitable mammalian test subject, such as a rodent. An example is the C57BL/6J mouse as used in the examples. A suitable individual test dosage may be 300 nmol/kg body weight, although the skilled person will be capable of determining suitable dosages.

As discussed above, one aspect of the present invention relates to a compound having the formula I:

$$R^1\text{—}Z\text{—}R^2 \tag{I}$$

wherein
$R^1$ is hydrogen, $C_{1-4}$ alkyl, formyl, acetyl, trifluoroacetyl or benzoyl;
$R^2$ is OH or $NH_2$; and
Z is an amino acid sequence having the formula Ia:

or is a truncated form thereof lacking from 1 to 23 amino acids from the C-terminus;
wherein
$X^1$ is an amino acid residue selected from Ala, Inp, Pro, DPro, Sar, Aib, Phe and Ser;
$X^2$ is Ser; or
$X^1$ and $X^2$ together constitute a residue of a non-naturally occurring amino acid, wherein the shortest bond separation between the amino nitrogen atom and the carbon atom of the carbonyl group in the non-naturally occurring amino acid is 3 to 7 bonds;
when $X^1$ is an amino acid residue selected from Pro, DPro, Phe and Ser, or when $X^1$ and $X^2$ together constitute a residue of the non-naturally occurring amino acid, then $X^3$ is selected among:

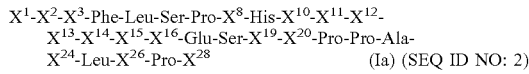

and when $X^1$ is an amino acid residue selected from Ala, Sar, Inp and Aib, then $X^3$ is selected among:

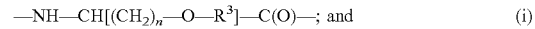

wherein
$R^3$ and $R^4$ are, independently, $C_{1-35}$-alkyl or -alkenyl groups;
$R^5$ and $R^6$ are, independently, $C_{1-35}$-acyl groups; and
n, m and p are integers 1, 2, 3, 4 or 5;
when present
$X^8$ is selected from Glu, Lys and Tyr;
$X^{10}$ is selected from Gln, Glu and Ser;
$X^{11}$ is selected from Arg, Lys and Ser;
$X^{12}$ is selected from Val, Ala, Pro, Lys, Thr and Leu;
$X^{13}$ is selected from Gln and Ser;
$X^{14}$ is selected from Gln, Lys, Tyr and Ser, or is absent;
$X^{15}$ is selected from Arg and Ser;
$X^{16}$ is selected from Lys, Ser and Pro;
$X^{19}$ is selected from Lys and Ser;
$X^{20}$ is selected from Lys, Glu and Ser;
$X^{24}$ is selected from Lys, Tyr and Ser;
$X^{26}$ is selected from Gln and Ser; and
$X^{28}$ is selected from Arg and Ser;
and, optionally, one or more of said amino acid residues $X^8$, $X^{10}$, $X^{11}$, $X^{13}$, $X^{14}$, $X^{16}$, $X^{19}$, $X^{20}$, $X^{24}$, $X^{26}$ and $X^{28}$ independently, is replaced with a modified lysine residue comprising a lipophilic substituent having the formula $Z^1Z^2\text{—}$, wherein $Z^2$ is a spacer moiety or is absent, and $Z^1$ is a lipophilic moiety conjugated, either via $Z^2$ or directly, to the side-chain of said lysine residue;
or a pharmaceutically acceptable salt or solvate of any of the above.

In certain embodiments, the invention provides a compound of formula I $$R^1\text{—}Z\text{—}R^2 \tag{I}$$

wherein
$R^1$ is hydrogen, $C_{1-4}$ alkyl, formyl, acetyl, trifluoroacetyl or benzoyl;
$R^2$ is —OH or —$NH_2$; and
Z is an amino acid sequence having the formula Ib:

or is a truncated form thereof lacking from 1 to 23 amino acids from the C-terminus;
wherein
$X^1$ is an amino acid residue selected from Ala, Inp, Pro, DPro, Sar, Aib, Phe and Ser;
$X^2$ is Ser; or
$X^1$ and $X^2$ together constitute a residue of a non-naturally occurring amino acid, wherein the shortest bond separation between the amino nitrogen atom and the carbon atom of the carbonyl group in the non-naturally occurring amino acid is 3 to 7 bonds;
when $X^1$ is an amino acid residue selected from Pro, DPro, Phe and Ser, or when $X^1$ and $X^2$ together constitute a residue of the non-naturally occurring amino acid, then $X^3$ is selected among:

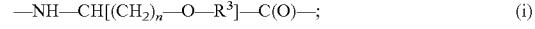

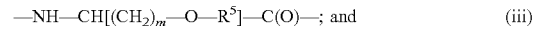

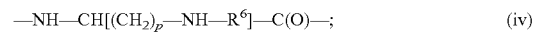

and when $X^1$ is an amino acid residue selected from Ala, Sar, Inp and Aib, then $X^3$ is selected among:

$$—NH—CH[(CH_2)_n—O—R^3]—C(O)—; \text{ and} \qquad (i)$$

$$—NH—CH(R^4)—C(O)—; \qquad (ii)$$

wherein
$R^3$ and $R^4$ are, independently, $C_{1-35}$-alkyl or -alkenyl groups;
$R^5$ and $R^6$ are, independently, $C_{1-35}$-acyl groups; and
n, m and p are integers 1, 2, 3, 4 or 5;
when present
$X^{10}$ is selected from Gln and Ser;
$X^{11}$ is selected from Arg and Lys;
$X^{12}$ is selected from Val, Ala, Thr and Leu;
$X^{13}$ is selected from Gln and Ser;
$X^{14}$ is selected from Gln and Ser, or is absent;
$X^{16}$ is Lys;
$X^{19}$ is Lys;
$X^{20}$ is Lys;
$X^{24}$ is Lys; and
$X^{26}$ is selected from Gln and Ser;
$X^{28}$ is Arg;
and, optionally, one or more of said amino acid residues $X^{10}$, $X^{11}$, $X^{13}$, $X^{14}$, $X^{16}$, $X^{19}$, $X^{20}$, $X^{24}$, $X^{26}$ and $X^{28}$ independently, is replaced with a modified lysine residue comprising a lipophilic substituent having the formula $Z^1Z^2$—, wherein $Z^2$ is a spacer moiety or is absent, and $Z^1$ is a lipophilic moiety conjugated, either via $Z^2$ or directly, to the side-chain of said lysine residue;
or a pharmaceutically acceptable salt or solvate of any of the above.

In some embodiments of compounds of the invention the compound is a compound of formula (I):

$$R^1—Z—R^2 \qquad (I)$$

wherein
$R^1$ is hydrogen, $C_{1-4}$ alkyl, formyl, acetyl, trifluoroacetyl or benzoyl;
$R^2$ is —OH or —$NH_2$; and
Z is an amino acid sequence having the formula Ib:

$$X^1\text{-}X^2\text{-}X^3\text{-Phe-Leu-Ser-Pro-Glu-His-}X^{10}\text{-}X^{11}\text{-}X^{12}\text{-} \\ X^{13}\text{-}X^{14}\text{-Arg-}X^{16}\text{-Glu-Ser-}X^{19}\text{-}X^{20}\text{-Pro-Pro-Ala-} \\ X^{24}\text{-Leu-}X^{26}\text{-Pro-}X^{28} \qquad \text{(Ib) (SEQ ID NO: 3)}$$

or is a truncated form thereof lacking from 1 to 23 amino acids from the C-terminus;
wherein
$X^1$ is an amino acid residue selected from Ala, Inp, Pro, DPro, Sar, Aib, Phe and Ser;
$X^2$ is Ser; or
$X^1$ and $X^2$ together constitute a residue of a non-naturally occurring amino acid, wherein the shortest bond separation between the amino nitrogen atom and the carbon atom of the carbonyl group in the non-naturally occurring amino acid is 3 to 7 bonds;
when $X^1$ is an amino acid residue selected from Pro, DPro, Phe and Ser, or when $X^1$ and $X^2$ together constitute a residue of the non-naturally occurring amino acid selected from cACC, tACC, Mamb and Cmp, then $X^3$ is selected from among:

$$—NH—CH[(CH_2)_n—O—R^3]—C(O)—; \qquad (i)$$

$$—NH—CH(R^4)—C(O)—; \qquad (ii)$$

$$—NH—CH[(CH_2)_m—O—R^5]—C(O)—; \text{ and} \qquad (iii)$$

$$—NH—CH[(CH_2)_p—NH—R^6]—C(O)—; \qquad (iv)$$

and when $X^1$ is an amino acid residue selected from Ala, Sar, Inp and Aib, then $X^3$ is selected from among:

$$—NH—CH[(CH_2)_n—O—R^3]—C(O)—; \text{ and} \qquad (i)$$

$$—NH—CH(R^4)—C(O)—; \qquad (ii)$$

wherein
$R^3$ and $R^4$ are, independently, $C_{1-35}$-alkyl or -alkenyl groups;
$R^5$ and $R^6$ are, independently, $C_{1-35}$-acyl groups; and
n, m and p are integers 1, 2, 3, 4 or 5;
when present
$X^{10}$ is Gln;
$X^{11}$ is selected from Arg and Lys;
$X^{12}$ is selected from Val, Ala, Thr and Leu;
$X^{13}$ is Gln;
$X^{14}$ is Gln or is absent;
$X^{16}$ is Lys;
$X^{19}$ is Lys;
$X^{20}$ is Lys;
$X^{24}$ is Lys; and
$X^{26}$ is Gln;
$X^{28}$ is Arg;
and optionally, wherein one or more of said amino acid residues $X^{10}$, $X^{11}$, $X^{13}$, $X^{14}$, $X^{16}$, $X^{19}$, $X^{20}$, $X^{24}$, $X^{26}$ and $X^{28}$ independently, is replaced with a modified lysine residue comprising a lipophilic substituent having the formula $Z^1Z^2$—, wherein $Z^2$ is a spacer moiety or is absent, and $Z^1$ is a lipophilic moiety conjugated, either via $Z^2$ or directly, to the side-chain of said lysine residue;
or a pharmaceutically acceptable salt or solvate of any of the above.

In any of the above formulae, it may be desirable that $X^1$ is Pro and $X^3$ is selected from $$—NH—CH[(CH_2)_n—O—R^3]—C(O)—; \text{ and} \qquad (i)$$

$$—NH—CH[(CH_2)_p—NH—R^6]—C(O)—. \qquad (iv)$$

Thus the invention further provides a compound comprising the formula I:

$$R^1—Z—R^2 \qquad (I)$$

wherein
$R^1$ is hydrogen, $C_{1-4}$ alkyl, formyl, acetyl, trifluoroacetyl or benzoyl;
$R^2$ is OH or $NH_2$; and
Z is an amino acid sequence having the formula Ic:

$$\text{Pro-Ser-}X^3\text{-Phe-Leu-Ser-Pro-Glu-His-}X^{10}\text{-}X^{11}\text{-}X^{12}\text{-} \\ X^{13}\text{-}X^{14}\text{-Arg-}X^{16}\text{-Glu-Ser-}X^{19}\text{-}X^{20}\text{-Pro-Pro-Ala-} \\ X^{24}\text{-Leu-}X^{26}\text{-Pro-}X^{28} \qquad \text{(Ic) (SEQ ID NO: 4)}$$

or is a truncated form thereof lacking from 1 to 23 amino acids from the C-terminus;
wherein
$X^3$ is selected from among:

$$—NH—CH[(CH_2)_n—O—R^3]—C(O)—; \text{ and} \qquad (i)$$

$$—NH—CH[(CH_2)_p—NH—R^6]—C(O)—; \qquad (iv)$$

wherein
$R^3$ is a $C_{1-35}$-alkyl or -alkenyl group;
$R^6$ is a $C_{1-35}$-acyl group; and
n and p are integers 1, 2, 3, 4 or 5;
when present
$X^{10}$ is selected from Gln and Ser; $X^{11}$ is selected from Arg and Lys;
$X^{12}$ is selected from Val, Ala, Thr and Leu;
$X^{13}$ is selected from Gln and Ser;
$X^{14}$ is selected from Gln and Ser, or is absent;
$X^{16}$ is Lys;

$X^{19}$ is Lys;
$X^{20}$ is Lys;
$X^{24}$ is Lys; and
$X^{26}$ is selected from Gln and Ser;
$X^{28}$ is Arg;
and optionally, wherein one or more of said amino acid residues $X^{10}$, $X^{11}$, $X^{13}$, $X^{14}$, $X^{16}$, $X^{19}$, $X^{20}$, $X^{24}$, $X^{26}$ and $X^{28}$ independently, is replaced with a modified lysine residue comprising a lipophilic substituent having the formula $Z^1Z^2$—, wherein $Z^2$ is a spacer moiety or is absent, and $Z^1$ is a lipophilic moiety conjugated, either via $Z^2$ or directly, to the side-chain of said lysine residue;
or a pharmaceutically acceptable salt or solvate of any of the above In certain embodiments, $X^3$ is —NH—CH[(CH$_2$)$_n$—O—R$^3$]—C(O)— (where n and R$^3$ are as defined above), $X^{12}$ is Val and $X^{20}$ is Ser.

Thus the compound may have the formula I:

$$R^1—Z—R^2 \qquad (I)$$

wherein
$R^1$ is hydrogen, $C_{1-4}$ alkyl, formyl, acetyl, trifluoroacetyl or benzoyl;
$R^2$ is OH or NH$_2$; and
Z is an amino acid sequence having the formula Id:

Pro-Ser-X$^3$-Phe-Leu-Ser-Pro-Glu-His-X$^{10}$-X$^{11}$-Val-X$^{13}$-X$^{14}$-Arg-X$^{16}$-Glu-Ser-X$^{19}$-Ser-Pro-Pro-Ala-X$^{24}$-Leu-X$^{26}$-Pro-X$^{28}$ (Id) (SEQ ID NO: 5)

or is a truncated form thereof lacking from 1 to 23 amino acids from the C-terminus;
wherein
$X^3$ is —NH—CH[(CH$_2$)$_n$—O—R$^3$]—C(O)—
wherein
$R^3$ is a $C_{1-35}$-alkyl or -alkenyl group and n is an integer 1, 2, 3, 4 or 5;
when present
$X^{10}$ is selected from Gln and Ser;
$X^{11}$ is selected from Arg and Lys;
$X^{13}$ is selected from Gln and Ser;
$X^{14}$ is selected from Gln and Ser, or is absent;
$X^{16}$ is Lys;
$X^{19}$ is Lys;
$X^{24}$ is Lys; and
$X^{26}$ is selected from Gln and Ser;
$X^{28}$ is Arg;
and optionally, wherein one or more of said amino acid residues $X^{10}$, $X^{11}$, $X^{13}$, $X^{14}$, $X^{16}$, $X^{19}$, $X^{24}$, $X^{26}$ and $X^{28}$ independently, is replaced with a modified lysine residue comprising a lipophilic substituent having the formula $Z^1Z^2$—, wherein $Z^2$ is a spacer moiety or is absent, and $Z^1$ is a lipophilic moiety conjugated, either via $Z^2$ or directly, to the side-chain of said lysine residue;
or a pharmaceutically acceptable salt or solvate of any of the above.

In alternative embodiments, $X^3$ is —NH—CH[(CH$_2$)$_p$—NH—R$^6$]—C(O)—, $X^{12}$ is Val and $X^{20}$ is Ser.

Thus the compound may have the formula I:

$$R^1—Z—R^2 \qquad (I)$$

wherein
$R^1$ is hydrogen, $C_{1-4}$ alkyl, formyl, acetyl, trifluoroacetyl or benzoyl;
$R^2$ is OH or NH$_2$; and
Z is an amino acid sequence having the formula Id:

Pro-Ser-X$^3$-Phe-Leu-Ser-Pro-Glu-His-X$^{10}$-X$^{11}$-Val-X$^{13}$-X$^{14}$-Arg-X$^{16}$-Glu-Ser-X$^{19}$-Ser-Pro-Pro-Ala-X$^{24}$-Leu-X$^{26}$-Pro-X$^{28}$ (Id) (SEQ ID NO: 5)

or is a truncated form thereof lacking from 1 to 23 amino acids from the C-terminus;
wherein
$X^3$—NH—CH[(CH$_2$)$_p$—NH—R$^6$]—C(O)—
wherein
$R^6$ is a $C_{1-35}$-acyl group and p is an integer 1, 2, 3, 4 or 5;
when present
$X^{10}$ is selected from Gln, Glu and Ser;
$X^{11}$ is selected from Arg and Lys;
$X^{13}$ is selected from Gln and Ser;
$X^{14}$ is selected from Gln and Ser, or is absent;
$X^{16}$ is Lys;
$X^{19}$ is Lys;
$X^{24}$ is Lys; and
$X^{26}$ is selected from Gln and Ser;
$X^{28}$ is Arg;
and optionally, wherein one or more of said amino acid residues $X^{10}$, $X^{11}$, $X^{13}$, $X^{14}$, $X^{16}$, $X^{19}$, $X^{24}$, $X^{26}$ and $X^{28}$ independently, is replaced with a modified lysine residue comprising a lipophilic substituent having the formula $Z^1Z^2$—, wherein $Z^2$ is a spacer moiety or is absent, and $Z^1$ is a lipophilic moiety conjugated, either via $Z^2$ or directly, to the side-chain of said lysine residue;
or a pharmaceutically acceptable salt or solvate of any of the above.

In some embodiments $X^{28}$ is not one of the residues which may be replaced by the modified lysine residue.

In some embodiments of a compound (or a pharmaceutically acceptable salt or solvate thereof, said salts or solvates to be understood as being included in any embodiment of the invention described herein unless specifically excluded), of the invention, $X^1$ is an amino acid residue selected from Ala, Inp, Pro, DPro, Sar, Aib, Phe and Ser; and $X^3$ is selected from among: (i) —NH—CH[(CH$_2$)$_n$—O—R$^3$]—C(O)—; and (ii) —NH—CH(R$^4$)—C(O)—.

In further embodiments of a compound, or a pharmaceutically acceptable salt or solvate thereof, of the invention, $X^1$ is an amino acid residue selected from Pro, DPro, Phe and Ser; and $X^3$ is selected from among: (i) —NH—CH[(CH$_2$)$_n$—O—R$^3$]—C(O)—; (ii) —NH—CH(R$^4$)—C(O)—; (iii) —NH—CH[(CH$_2$)$_m$—O—R$^5$]—C(O)—; and (iv) —NH—CH[(CH$_2$)$_p$—NH—R$^6$]—C(O)—.

In certain embodiments of a compound, or a pharmaceutically acceptable salt or solvate thereof, of the invention, $X^1$ is an amino acid residue selected from Pro, DPro and Aib, such as an amino acid residue selected from Pro and DPro.

More generally, $X^1$ and $X^2$ together may constitute one of a wide variety of amino acid residues in which the spatial relationship of at least some atoms or functional groups is similar to that of the Gly1-Ser2 fragment of ghrelin, such as the spatial relationship between the carbonyl carbon of Ser and the basic α-amino nitrogen of Gly. Spatial relationship may, for example, be similar in terms of three-dimensional orientation of, or distances between, atoms or functional groups, but spatial relationship of atoms or functional groups may also be with reference to simpler features, such as the number of bonds between atoms or functional groups.

In the present invention, the spatial relationship of atoms or functional groups relates to the shortest bond separation (3 to 7) between the amino nitrogen atom and the carbon atom of the carbonyl group in the non-naturally occurring amino acid.

For a Gly-Ser fragment the number of bonds between the carbonyl carbon of Ser and the α-amino nitrogen of Gly is 5. In residues of the specific non-naturally occurring amino acids cACC, tACC, Cmp, and Mamb that are present in certain embodiments of compounds of the present invention, a separation of 5 bonds is likewise present between the carbonyl carbon and the amino nitrogen. A separation of from 3 to 7 bonds (such as 5 bonds) provides spatial similarity to the corresponding distance in a Gly-Ser fragment. Such residues may or may not contain cyclic moieties.

Thus, in some embodiments, $X^1$ and $X^2$ together constitute a residue of a non-naturally occurring amino acid, wherein the shortest bond separation between the amino nitrogen atom and the carbon atom of the carbonyl group in the non-naturally occurring amino acid is 3 to 7 bonds.

In some embodiments of a compound, or a pharmaceutically acceptable salt or solvate thereof, of the invention, $X^1$ and $X^2$ together constitute a residue of a non-naturally occurring amino acid selected from cACC, tACC, Mamb and Cmp.

Examples of other non-naturally occurring amino acid residues that may be of relevance in this connection include, but are not limited to, the following:

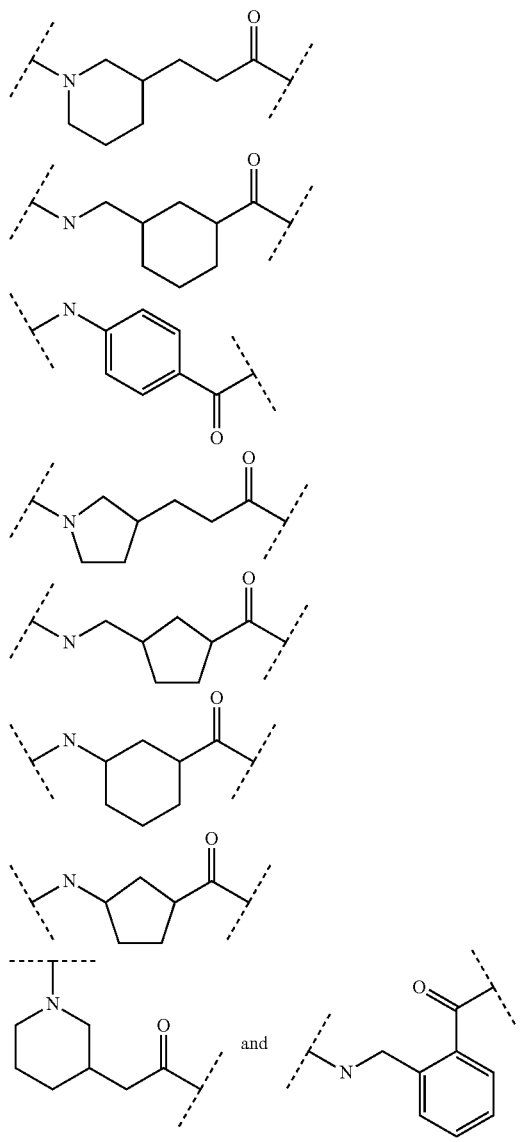

Further non-naturally occurring amino acid residues that may likewise be of relevance in this connection include ornithine (Orn) and α-N-acetylornithine(AcOrn).

For the avoidance of doubt, "non-naturally occurring amino acid residue" and equivalent terms are used to signify amino acid residues other than the group of 20 amino acids normally incorporated into proteins by mammalian transcription and translation systems before any post-translational modification (i.e. amino acids other than Glycine, Alanine, Valine, Leucine, Isoleucine, Serine, Cysteine, Threonine, Methionine, Proline, Phenylalanine, Tyrosine, Tryptophan, Histidine, Lysine, Arginine, Aspartate, Glutamate, Asparagine and Glutamine). They should not be taken to require that the amino acid itself does not occur in nature (although such amino acids may certainly be used).

In certain embodiments of a compound, or a pharmaceutically acceptable salt or solvate thereof, of the invention, $X^3$ is selected among: (i) —NH—CH[(CH$_2$)$_n$—O—R$^3$]—C(O)—; and (ii) —NH—CH(R$^4$)—C(O)—. In certain embodiments, $X^3$ is selected from among: (iii) —NH—CH[(CH$_2$)$_m$—O—R$^5$]—C(O)—; and (iv) —NH—CH[(CH$_2$)$_p$—NH—R$^6$]—C(O)—.

In some embodiments of a compound, or a pharmaceutically acceptable salt or solvate thereof, of the invention, $R^3$, when present, is a $C_{5-16}$-alkyl or -alkenyl group. In some embodiments of a compound, or a pharmaceutically acceptable salt or solvate thereof, of the invention, $R^3$, when present, is a $C_{7-10}$-alkyl or -alkenyl group. In certain embodiments of a compound, or a pharmaceutically acceptable salt or solvate thereof, of the invention, $R^3$, when present, is a $C_8$-alkyl or -alkenyl group In some embodiments of a compound, or a pharmaceutically acceptable salt or solvate thereof, of the invention, $R^4$, when present, is a $C_{7-18}$-alkyl or -alkenyl group. In some embodiments of a compound, or a pharmaceutically acceptable salt or solvate thereof, of the invention, $R^4$, when present, is a $C_{7-12}$-alkyl or -alkenyl group, such as a $C_{7-10}$-alkyl or -alkenyl group. In certain embodiments of a compound, or a pharmaceutically acceptable salt or solvate thereof, of the invention, $R^4$, when present, is a $C_{10}$-alkyl or -alkenyl group In certain embodiments of compound, or a pharmaceutically acceptable salt or solvate thereof, of the invention, $R^5$, when present, is a $C_{5-16}$-acyl group. In some embodiments of compound, or a pharmaceutically acceptable salt or solvate thereof, of the invention, $R^5$, when present, is a $C_{7-10}$-acyl group. In certain embodiments of compound, or a pharmaceutically acceptable salt or solvate thereof, of the invention, $R^5$, when present, is a $C_8$-acyl group.

In certain embodiments of a compound, or a pharmaceutically acceptable salt or solvate thereof, of the invention, $R^6$, when present, is a $C_{5-16}$-acyl group. In some embodiments of compound, or a pharmaceutically acceptable salt or solvate thereof, of the invention, $R^6$, when present, is a $C_{7-10}$-acyl group. In certain embodiments of compound, or a pharmaceutically acceptable salt or solvate thereof, of the invention, $R^6$, when present, is a $C_8$-acyl group.

In the compound, or a pharmaceutically acceptable salt or solvate thereof, of the invention, the alkyl or alkenyl groups $R^3$ and $R^4$, and the alkyl or alkenyl groups present in the acyl groups $R^5$ and $R^6$ may independently be linear or branched.

Examples of linear saturated $C_{5-16}$-alkyl groups and $C_{7-18}$-alkyl groups include, but are not limited to, —(CH$_2$)$_n$CH$_3$ where n is an integer from 4 to 17, —CH$_2$CH$_2$CH$_2$CH—$_2$CH$_2$CH$_2$CH$_3$ (heptyl), —CH$_2$CH$_2$CH$_2$CH$_2$CH$_2$CH$_2$CH$_3$ (octyl) and —CH$_2$CH$_2$CH$_2$CH$_2$CH$_2$CH$_2$CH$_2$CH$_3$ (nonyl).

Examples of branched saturated $C_{5-16}$-alkyl groups and $C_{7-18}$-alkyl groups include, but are not limited to, —CH(CH$_3$)CH$_2$CH$_2$CH$_2$CH$_2$CH$_2$CH$_3$, —CH$_2$CH(CH$_3$)

$CH_2CH_2CH_2CH_2CH_3$, $—CH_2CH_2CH(CH_3)CH_2CH_2CH_3$, $—CH_2CH_2CH_2CH(CH_3)CH_2CH_2CH_3$, $—CH_2CH_2CH_2CH_2CH(CH_3)CH_2CH_3$, $—CH_2CH_2CH_2CH_2CH_2CH(CH_3)_2$, $—CH(CH_2CH_3)CH_2CH_2CH_2CH_2CH_2—$, $—CH_2CH(CH_2CH_3)CH_2CH_2CH_2CH_3$, $—CH_2CH_2CH(CH_2CH_3)CH_2CH_2CH_3$, $—CH_2CH_2CH_2CH(CH_2CH_3)CH_2CH_3$, $—CH_2CH_2CH_2CH_2CH(CH_2CH_3)CH_3$.

Examples of linear partially unsaturated $C_{5-16}$-alkenyl groups and $C_{7-16}$-alkenyl groups include, but are not limited to, $—CH=CH—CH_2—CH_2—CH_2—CH_2—CH_3$, $—CH_2—CH=CH_2—CH_2—CH_2—CH_2—CH_3$, $—CH_2—CH_2—CH=CH_2—CH_2—CH_2—CH_3$, $—CH_2—CH_2—CH_2—CH=CH_2—CH_2—CH_3$, $—CH_2—CH_2—CH_2—CH_2—CH=CH_2—CH_3$, $—CH_2—CH_2—CH_2—CH_2—CH_2—CH=CH_2$, $—CH=CH—CH=CH—CH_2—CH_2—CH_3$, $—CH=CH—CH=CH—CH_2—CH=CH_2$, $—CH=CH—CH_2—CH_2—CH=CH—CH_3$, $—CH=CH—CH=CH—CH_2—CH=CH_2$, $—CH=CH—CH=CH—CH=CH_2$.

Examples of branched partially unsaturated $C_{5-16}$-alkenyl groups and $C_{7-16}$-alkenyl groups include, but are not limited to, $—C(CH_3)=CH—CH_2—CH_2—CH_2—CH_3$, $—C(CH_3)=CH—CH_2—CH_2—CH_2—CH_2—CH_3$, $—CH=CH—CH_2—CH_2—CH_2—CH(CH_3)_2$, $—CH_2—CH_2—CH=CH—CH_2—CH(CH_3)_2$.

$C_{5-16}$-acyl groups may be represented as $—C(=O)R^4$, wherein $R^4$ is a linear or branched $C_{4-15}$-alkyl group (in which case such an acyl group may also be referred to as a $C_{5-16}$-alkanoyl group) or a linear or branched $C_{4-15}$-alkenyl group (in which case such an acyl group may also be referred to as a $C_{5-16}$-alkenoyl group). Examples of acyl groups include, but are not limited to, $—C(=O)CH_2CH_2CH_2CH_2CH_2CH_3$ (heptanoyl), $—C(=O)CH_2CH_2CH_2CH_2CH_2CH_2CH_3$ (octanoyl) and $—C(=O)CH_2CH_2CH_2CH_2CH_2CH_2CH_2CH_3$ (nonanoyl).

In some embodiments of a compound, or a pharmaceutically acceptable salt or solvate thereof, of the invention, the integer n, m, or p is 1.

The compounds of the invention may carry one or more intramolecular bridge within the peptide sequence Z. Each such bridge is formed between the side chains of two amino acid residues of Z. The two residues may be separated by one, two, three or more amino acids in the linear sequence of Z. Thus the bridge may be formed between a pair of residues at positions $X^A$ and $X^{A+2}$, positions $X^A$ and $X^{A+3}$, positions $X^A$ and $X^{A+4}$, or any other suitable pair of residues.

For example, a Lys residue at position $X^8$ may form an intramolecular bridge with any Glu residue in the molecule, e.g. a Glu residue at position $X^{10}$ or $X^{20}$.

A Lys residue at position $X^{11}$ may form an intramolecular bridge with any Glu residue in the molecule, e.g. a Glu residue at position $X^8$ or $X^{20}$.

A Lys residue at position $X^{12}$ may form an intramolecular bridge with any Glu residue in the molecule, e.g. a Glu residue at position $X^8$, $X^{10}$ or $X^{20}$.

A Lys residue at position $X^{16}$ may form an intramolecular bridge with any Glu residue in the molecule, e.g. a Glu residue at position $X^8$, $X^{10}$ or $X^{20}$.

A Lys residue at position $X^{19}$ may form an intramolecular bridge with any Glu residue in the molecule, e.g. a Glu residue at position $X^8$ or $X^{10}$.

A Lys residue at position $X^{20}$ may form an intramolecular bridge with any Glu residue in the molecule, e.g. a Glu residue at position $X^8$ or $X^{10}$.

A Lys residue at position $X^{24}$ may form an intramolecular bridge with any Glu residue in the molecule, e.g. a Glu residue at position $X^8$, $X^{10}$ or $X^{20}$.

A Glu residue at position $X^8$ may form an intramolecular bridge with any Lys residue in the molecule, e.g. a Lys residue at position $X^{11}$, $X^{12}$, $X^{14}$, $X^{16}$, $X^{19}$, $X^{20}$ or $X^{24}$.

A Glu residue at position $X^{10}$ may form an intramolecular bridge with any Lys residue in the molecule, e.g. a Lys residue at position $X^8$, $X^{12}$, $X^{14}$, $X^{16}$, $X^{19}$, $X^{20}$ or $X^{24}$.

A Glu residue at position $X^{20}$ may form an intramolecular bridge with any Lys residue in the molecule, e.g. a Lys residue at position $X^8$, $X^{11}$, $X^{12}$, $X^{14}$, $X^{16}$ or $X^{24}$.

By way of example, the bridge may be formed between the side chains of residue pairs $X^8$ and $X^{12}$, $X^{10}$ and $X^{14}$, or $X^{16}$ and $X^{20}$. The two side chains can be linked to one another through ionic interactions, or by covalent bonds, typically to form a lactam ring.

Typically, the two amino acids which form the intramolecular bridge are Lys and Glu.

Thus, when a Glu is present at position $X^8$, a Lys may be present at position $X^{12}$.

When a Glu is present at position $X^{10}$, a Lys may be present at position $X^{14}$.

When a Lys is present at position $X^{16}$, a Glu may be present at position $X^{20}$.

In some embodiments of a compound, or a pharmaceutically acceptable salt or solvate thereof, of the invention, $Z^1$ is a long-chain fatty acid acyl moiety, such as a fatty acid moiety selected from dodecanoyl, 2-butyloctanoyl, tetradecanoyl, hexadecanoyl, heptadecanoyl, octadecanoyl, and eicosanoyl.

In some embodiments of a compound, or a pharmaceutically acceptable salt or solvate thereof, of the invention, $Z^2$ is a spacer moiety comprising one or more amino acid residues. $Z^2$ may, for example, be an amino acid residue selected from Glu, γGlu (derived from γ-glutamic acid) and Bal, or a residue of an amino acid selected from 3-aminopropanoic acid, 4-aminobutanoic acid, 8-aminooctanoic acid and 8-amino-3,6-dioxaoctanoic acid.

Specific embodiments of compounds of the invention include compounds selected from the group consisting of:
H-PS-S(O-octanoyl)-FLSPEHQRVQQRKESKKPPAK-LQPR-OH (SEQ ID NO: 7);
H-[DPro]-S-S(O-octanoyl)-FLSPEHQRVQQRKESKKP-PAKLQPR-OH (SEQ ID NO: 8);
H-FS-S(O-octanoyl)-FLSPEHQRVQQRKESKKPPAK-LQPR-OH (SEQ ID NO: 9);
H-SS-S(O-octanoyl)-FLSPEHQRVQQRKESKKPPAK-LQPR-OH (SEQ ID NO: 10);
H-Cmp-S(O-octanoyl)-FLSPEHQRVQQRKESKKPPAK-LQPR-OH (SEQ ID NO: 11);
H-Mamb-S(O-octanoyl)-FLSPEHQRVQQRKESKKPPAK-LQPR-OH (SEQ ID NO: 12);
H-[cACC]-S(O-octanoyl)-FLSPEHQRVQQRKESKKP-PAKLQPR-OH (SEQ ID NO: 13);
H-[tACC]-S(O-octanoyl)-FLSPEHQRVQQRKESKKP-PAKLQPR-OH (SEQ ID NO: 14);
H-Inp-S-S(O-octyl)-FLSPEHQRV-K(hexadecanoyl)-QRKESKKPPAKLQPR-OH (SEQ ID NO: 15);
H-Inp-S-S(O-octyl)-FLSPEHQRVQQRKES-K(hexadecanoyl)-KPPAKLQPR-OH (SEQ ID NO: 16);
H-Inp-S-S(O-octyl)-FLSPEHQRVQQRKESKKPPAKL-K(hexadecanoyl)-PR-OH (SEQ ID NO: 17);
H-PS-S(O-octyl)-FLSPEHQRVQQRKES-K(hexadecanoyl)-KPPAKLQPR-OH (SEQ ID NO: 18);
H-[DPro]-S-S(O-octyl)-FLSPEHQRVQQRKES-K(hexadecanoyl)-KPPAKLQPR-OH (SEQ ID NO: 19);

H-Aib-S-S(O-octyl)-FLSPEHQRVQQRKES-K(hexadecanoyl)-KPPAKLQPR-OH (SEQ ID NO: 20);
H-PS-S(O-octyl)-FLSPEHQRVQQRKESKKPPAKLQPR-OH (SEQ ID NO: 21);
H-[DPro]-S-S(O-octyl)-FLSPEHQRVQQRKESKKPPAKLQPR-OH (SEQ ID NO: 22); and
H-Aib-S-S(O-octyl)-FLSPEHQRVQQRKESKKPPAKLQPR-OH (SEQ ID NO: 23).

Pharmaceutically acceptable salts or solvates of any of the above compounds are likewise within the scope of the invention.

Further specific embodiments of compounds of the invention include compounds selected from the group consisting of:
H-AS-S(O-octyl)-FLSPEHQRVQQRKESKKPPAKLQPR-OH (SEQ ID NO: 24);
H-[cACC]-S(O-octyl)-FLSPEHQRVQQRKESKKPPAKLQPR-OH (SEQ ID NO: 25);
H-Cmp-S(O-octyl)-FLSPEHQRV-K(hexadecanoyl)-QRKESKKPPAKLQPR-OH (SEQ ID NO: 26);
H-FS-S(O-octyl)-FLSPEHQRVQQR-K(hexadecanoyl)-ESKKPPAKLQPR-OH (SEQ ID NO: 27);
H-[DPro]-S-S(O-octyl)-FLSPEHQRVQQRKES-K(hexadecanoyl)-KPPAKLQPR-OH (SEQ ID NO: 28);
H-Aib-S-S(O-octyl)-FLSPEHQRVQQRKESK-K(hexadecanoyl)-PPAKLQPR-OH (SEQ ID NO: 29);
H-Sar-S-S(O-octyl)-FLSPEHQRVQQRKESKKPPAKL-K(hexadecanoyl)-PR-OH (SEQ ID NO: 30);
H-AS-S(O-octyl)-FLSPEHQRVQQRKESKKPPAKLQPR-NH$_2$ (SEQ ID NO: 31);
H-Inp-S-S(O-octyl)-FLSPEHQRVQQRKESKKPPAKLQPR-NH$_2$ (SEQ ID NO: 32);
H-PS-S(O-octyl)-FLSPEHQRVQQRKESKKPPAKLQPR-NH$_2$ (SEQ ID NO: 33);
H-[DPro]-S-S(O-octyl)-FLSPEHQRVQQRKESKKPPAKLQPR-NH$_2$ (SEQ ID NO: 34);
H-PS-S(O-octyl)-FLSPEHQRV-K(hexadecanoyl)-QRKESKKPPAKLQPR-NH$_2$ (SEQ ID NO: 35);
H-Mamb-S(O-octyl)-FLSPEHQRV-K(hexadecanoyl)-QRKESKKPPAKLQPR-NH$_2$ (SEQ ID NO: 36);
H-SS-S(O-octyl)-FLSPEHQRVQQRKES-K(hexadecanoyl)-KPPAKLQPR-NH$_2$ (SEQ ID NO: 37);
H-AS-S(O-octyl)-FLSPEHQRVQQRKESKKPPAKL-K(hexadecanoyl)-PR-NH$_2$ (SEQ ID NO: 38);
H-Aib-S-S(O-octyl)-FLSPEHQRVQQRKESKKPPAKL-K(hexadecanoyl)-PR-NH$_2$ (SEQ ID NO: 39);
H-PS-[NH—CH(n-C$_{10}$H$_{21}$)—C(O)]-FLSPEHQRVQQRKESKKPPAKLQPR-OH (SEQ ID NO: 40);
H-[DPro]-S—[NH—CH(n-C$_{10}$H$_{21}$)—C(O)]-FLSPEHQRVQQRKESKKPPAKLQPR-OH (SEQ ID NO: 41);
H-Cmp-[NH—CH(n-C$_{10}$H$_{21}$)—C(O)]-FLSPEHQRVQQRKESKKPPAKLQPR-OH (SEQ ID NO: 42);
H-[DPro]-S—[NH—CH(n-C$_{10}$H$_{21}$)—C(O)]-FLSPEHQRV-K(hexadecanoyl)-QRKESKKPPAKLQPR-OH (SEQ ID NO: 43);
H-Sar-S—[NH—CH(n-C$_{10}$H$_{21}$)—C(O)]-FLSPEHQRVQQR-K(hexadecanoyl)-ESKKPPAKLQPR-OH (SEQ ID NO: 44);
H-Aib-S—[NH—CH(n-C$_{10}$H$_{21}$)—C(O)]-FLSPEHQRVQQR-K(hexadecanoyl)-ESKKPPAKLQPR-OH (SEQ ID NO: 45);
H-[cACC]-[NH—CH(n-C$_{10}$H$_{21}$)—C(O)]-FLSPEHQRVQQRKES-K(hexadecanoyl)-KPPAKLQPR-OH (SEQ ID NO: 46);
H-[DPro]-S—[NH—CH(n-C$_{10}$H$_{21}$)—C(O)]-FLSPEHQRVQQRKESK-K(hexadecanoyl)-PPAKLQPR-OH (SEQ ID NO: 47);
H-AS-[NH—CH(n-C$_{10}$H$_{21}$)—C(O)]-FLSPEHQRVQQRKESKKPPAKL-K(hexadecanoyl)-PR-OH (SEQ ID NO: 48);
H-Mamb-[NH—CH(n-C$_{10}$H$_{21}$)—C(O)]-FLSPEHQRVQQRKESKKPPAKLK(hexadecanoyl)-PR-OH (SEQ ID NO: 49);
H-AS-[NH—CH(n-C$_{10}$H$_{21}$)—C(O)]-FLSPEHQRVQQRKESKKPPAKLQPR-NH$_2$ (SEQ ID NO: 50);
H-Inp-S—[NH—CH(n-C$_{10}$H$_{21}$)—C(O)]-FLSPEHQRVQQRKESKKPPAKLQPR-NH$_2$ (SEQ ID NO: 51);
H-PS-[NH—CH(n-C$_{10}$H$_{21}$)—C(O)]-FLSPEHQRVQQRKESKKPPAKLQPR-NH$_2$ (SEQ ID NO: 52);
H-[DPro]-S—[NH—CH(n-C$_{10}$H$_{21}$)—C(O)]-FLSPEHQRVQQRKESKKPPAKLQPR-NH$_2$ (SEQ ID NO: 53);
H-SS-[NH—CH(n-C$_{10}$H$_{21}$)—C(O)]-FLSPEHQRVQQRKESKKPPAKLQPR-NH$_2$ (SEQ ID NO: 54);
H-Cmp-[NH—CH(n-C$_{10}$H$_{21}$)—C(O)]-FLSPEHQRVQQRKESKKPPAKLQPR-NH$_2$ (SEQ ID NO: 55);
H-[cACC]-[NH—CH(n-C$_{10}$H$_{21}$)—C(O)]-FLSPEHQRVQQRKESKKPPAKLQPR-NH$_2$ (SEQ ID NO: 56);
H-Sar-S—[NH—CH(n-C$_{10}$H$_{21}$)—C(O)]-FLSPEHQRV-K(hexadecanoyl)-QRKESKKPPAKLQPR-NH$_2$ (SEQ ID NO: 57);
H-Aib-S—[NH—CH(n-C$_{10}$H$_{21}$)—C(O)]-FLSPEHQRV-K(hexadecanoyl)-QRKESKKPPAKLQPR-NH$_2$ (SEQ ID NO: 58);
H-Cmp-[NH—CH(n-C$_{10}$H$_{21}$)—C(O)]-FLSPEHQRV-K(hexadecanoyl)-QRKESKKPPAKLQPR-NH$_2$ (SEQ ID NO: 59);
H-Inp-S—[NH—CH(n-C$_{10}$H$_{21}$)—C(O)]-FLSPEHQRVQQR-K(hexadecanoyl)-ESKKPPAKLQPR-NH$_2$ (SEQ ID NO: 60);
H-[DPro]-S—[NH—CH(n-C$_{10}$H$_{21}$)—C(O)]-FLSPEHQRVQQRKES-K(hexadecanoyl)-KPPAKLQPR-NH$_2$ (SEQ ID NO: 61);
H-SS-[NH—CH(n-C$_{10}$H$_{21}$)—C(O)]-FLSPEHQRVQQRKES-K(hexadecanoyl)-KPPAKLQPR-NH$_2$ (SEQ ID NO: 62);
H-Sar-S—[NH—CH(n-C$_{10}$H$_{21}$)—C(O)]-FLSPEHQRVQQRKESK-K(hexadecanoyl)-PPAKLQPR-NH$_2$ (SEQ ID NO: 63);
H-AS-[NH—CH(n-C$_{10}$H$_{21}$)—C(O)]-FLSPEHQRVQQRKESKKPPAKL-K(hexadecanoyl)-PR-NH$_2$ (SEQ ID NO: 64); and
H-PS-[NH—CH(n-C$_{10}$H$_{21}$)—C(O)]-FLSPEHQRVQQRKESKKPPAKL-K(hexadecanoyl)-PR-NH$_2$ (SEQ ID NO: 65);
H-PS-S(O-octanoyl)-FLSPEHQRV-K(hexadecanoyl)-QRKESKKPPAKLQPR-NH$_2$ (SEQ ID NO: 66);
H-[DPro]-S-S(O-octanoyl)-FLSPEHQRV-K(hexadecanoyl)-QRKESKKPPAKLQPR-NH$_2$ (SEQ ID NO: 67);
H-SS-S(O-octanoyl)-FLSPEHQRV-K(hexadecanoyl)-QRKESKKPPAKLQPR-NH$_2$ (SEQ ID NO: 68);
H-Cmp-S(O-octanoyl)-FLSPEHQRV-K(hexadecanoyl)-QRKESKKPPAKLQPR-NH$_2$ (SEQ ID NO: 69);
H-Cmp-S(O-octanoyl)-FLSPEHQRVQQR-K(hexadecanoyl)-ESKKPPAKLQPR-NH$_2$ (SEQ ID NO: 70);
H-[cACC]-S(O-octanoyl)-FLSPEHQRVQQR-K(hexadecanoyl)-ESKKPPAKLQPR-NH$_2$ (SEQ ID NO: 71);
H-[tACC]-S(O-octanoyl)-FLSPEHQRVQQRKES-K(hexadecanoyl)-KPPAKLQPR-NH$_2$ (SEQ ID NO: 72);
H-SS-S(O-octanoyl)-FLSPEHQRVQQRKESK-K(hexadecanoyl)-PPAKLQPR-NH$_2$ (SEQ ID NO: 73);
H-PS-Dap(N-octanoyl)-FLSPEHQRVQQRKESKKPPAKLQPR-OH (SEQ ID NO: 74);
H-[DPro]-S-Dap(N-octanoyl)-FLSPEHQRVQQRKESKKPPAKLQPR-OH (SEQ ID NO: 75);

H-SS-Dap(N-octanoyl)-FLSPEHQRVQQRKESKKPPAK-LQPR-OH (SEQ ID NO: 76);
H-PS-Dap(N-octanoyl)-FLSPEHQRVQQR-K(hexadecanoyl)-ESKKPPAKLQPR-OH (SEQ ID NO: 77);
H-Mamb-Dap(N-octanoyl)-FLSPEHQRVQQRKES-K(hexadecanoyl)-KPPAKLQPROH (SEQ ID NO: 78);
H-PS-Dap(N-octanoyl)-FLSPEHQRVQQRKESKKPPAK-LQPR-NH$_2$ (SEQ ID NO: 79);
H-[DPro]-S-Dap(N-octanoyl)-FLSPEHQRVQQRKESK-KPPAKLQPR-NH$_2$ (SEQ ID NO: 80);
H-SS-Dap(N-octanoyl)-FLSPEHQRVQQRKESKKPPAK-LQPR-NH$_2$ (SEQ ID NO: 81);
H-PS-Dap(N-octanoyl)-FLSPEHSRVSSRKESKKPPAKL-SPR-NH$_2$ (SEQ ID NO: 82);
H-Cmp-Dap(N-octanoyl)-FLSPEHQRVQQRKESKKP-PAKLQPR-NH$_2$ (SEQ ID NO: 83);
H-[cACC]-Dap(N-octanoyl)-FLSPEHQRVQQRKESKKP-PAKLQPR-NH$_2$ (SEQ ID NO: 84);
H-PS-Dap(N-octanoyl)-FLSPEHQRV-K(hexadecanoyl)-QRKESKKPPAKLQPR-NH$_2$ (SEQ ID NO: 85);
H-[DPro]-S-Dap(N-octanoyl)-FLSPEHQRV-K(hexadecanoyl)-QRKESKKPPAKLQPRNH$_2$ (SEQ ID NO: 86);
H-FS-Dap(N-octanoyl)-FLSPEHQRV-K(hexadecanoyl)-QRKESKKPPAKLQPR-NH$_2$ (SEQ ID NO: 87);
H-SS-Dap(N-octanoyl)-FLSPEHQRV-K(hexadecanoyl)-QRKESKKPPAKLQPR-NH$_2$ (SEQ ID NO: 88);
H-[DPro]-S-Dap(N-octanoyl)-FLSPEHQRVQQR-K(hexadecanoyl)-ESKKPPAKLQPR-NH$_2$ (SEQ ID NO: 89);
H-Mamb-Dap(N-octanoyl)-FLSPEHQRVQQR-K(hexadecanoyl)-ESKKPPAKLQPR-NH$_2$ (SEQ ID NO: 90);
H-PS-Dap(N-octanoyl)-FLSPEHQRVQQRKESK-K(hexadecanoyl)-PPAKLQPR-NH$_2$ (SEQ ID NO: 91);
H-SS-Dap(N-octanoyl)-FLSPEHQRVQQRKESK-K(hexadecanoyl)-PPAKLQPR-NH$_2$ (SEQ ID NO: 92);
and H-Cmp-Dap(N-octanoyl)-FLSPEHQRVQQRKESK-KPPAKL-K(hexadecanoyl)-PR-NH$_2$ (SEQ ID NO: 93).

Further specific embodiments of compounds of the invention include compounds selected from the group consisting of:
H-GS-S(octanoyl)-FLSPE(HQRK(QQRKESKKPPAK-LQPR-OH (SEQ ID NO: 94);
H-GS-S(octanoyl)-FLSPEHE(RVQK(RKESKKPPAK-LQPR-OH (SEQ ID NO: 95);
H-GS-S(octanoyl)-FLSPEHQRVQQRK(ESKE(PPAK-LQPR-OH (SEQ ID NO: 96);
H-PS-S(O-octyl)-FLSPEOH(  )QRKQQRKESKKPPAK-LQPR-NH$_2$ (SEQ ID NO: 97);
H-PS-S(O-octyl)-FLSPEHE(RVQK(RKESKKPPAK-LQPR-NH$_2$ (SEQ ID NO: 98);
H-Orn-S(O-octyl)-FLSPEHQRVQQRKESKKPPAKLQPR-NH$_2$ (SEQ ID NO: 99);
Ac-Orn-S(O-octyl)-FLSPEHQRVQQRKESKKPPAK-LQPR-NH$_2$ (SEQ ID NO: 99);
H-PS-Dap(N-octanoyl)-FLSPEHQRVQRKESKKPPAK-LQPR-NH$_2$ (SEQ ID NO: 100);
H-PS-S(O-octyl)-FLSPEHQRVQRKESKKPPAKLQPR-NH$_2$ (SEQ ID NO: 101);
H-PS-Dap(N-octanoyl)-FLSPK-NH$_2$ (SEQ ID NO: 102);
H-PS-S(O-octyl)-FLSPK-NH$_2$ (SEQ ID NO: 103);
H-PS-[NH—CH(n-C$_{10}$H$_{21}$)—C(O)]-FLSPK-NH$_2$ (SEQ ID NO: 104);
H-PS-Dap(N-octanoyl)-FLSPY-NH$_2$ (SEQ ID NO: 105);
H-PS-S(O-octyl)-FLSPEHQRVQQRKES-K(hexadecanoyl-isoGlu)-KPPAKLQPR-NH$_2$ (SEQ ID NO: 106);
H-PS-Dap(N-octanoyl)-FLSPEHSRVSSRKES-K(hexadecanoyl-isoGlu)-KPPA-NH$_2$ (SEQ ID NO: 107);
H-PS-S(O-octyl)-FLSPEHSRVSSRKESSKPPAKLSPR-NH$_2$ (SEQ ID NO: 108);
H-PS-S(O-octyl)-FLSPEHSRVSSRKESKSPPAKLSPR-NH$_2$ (SEQ ID NO: 109);
H-PS-S(O-octyl)-FLSPEHSRVSSRKESSSPPAKLSPR-NH$_2$ (SEQ ID NO: 110);
H-PS-S(O-octyl)-FLSPEHSRPSSR-NH$_2$ (SEQ ID NO: 111);
H-PS-S(O-octyl)-FLSPEHSRVSSRPESSSPPAKLSPR-NH$_2$ (SEQ ID NO: 112);
H-PS-S(O-octyl)-FLSPEHSRPSSRPESSSPPAKLSPR-NH$_2$ (SEQ ID NO: 113);
H-PS-S(octanoyl)-FLSPEHQSVQQRKESKKPPAKLQPR-NH$_2$ (SEQ ID NO: 114);
H-PS-S(octanoyl)-FLSPEHQRVQQSKESKKPPAKLQPR-NH$_2$ (SEQ ID NO: 115);
H-PS-S(octanoyl)-FLSPEHQRVQQRSESKKPPAKLQPR-NH$_2$ (SEQ ID NO: 116);
H-PS-S(octanoyl)-FLSPEHQRVQQRKESSKPPAKLQPR-NH$_2$ (SEQ ID NO: 117);
H-PS-S(octanoyl)-FLSPEHQRVQQRKESKSPPAKLQPR-NH$_2$ (SEQ ID NO: 118);
H-PS-S(octanoyl)-FLSPEHQRVQQRKESKKPPASLQPR-NH$_2$ (SEQ ID NO: 119);
H-PS-S(octanoyl)-FLSPEHQRVQQRKESKKPPAKLQPS-NH$_2$ (SEQ ID NO: 120);
H-PS-S(octanoyl)-FLSPYHQRVQQRKESKKPPAK-LQPR-NH$_2$ (SEQ ID NO: 121);
H-PS-S(octanoyl)-FLSPEHQRVQYRKESKKPPAKLQPR-NH$_2$ (SEQ ID NO: 122);
H-PS-S(octanoyl)-FLSPEHQRVQQRKESKKPPAYLQPR-NH$_2$ (SEQ ID NO: 123);
H-PS-S(octanoyl)-FLSPYHQRVQYRKESKKPPAYLQPR-NH$_2$ (SEQ ID NO: 124);
H-PS-S(O-octyl)-FLSPEHQRVQQRKESKKPPAKLQPR-NH$_2$ (SEQ ID NO: 125);
H-PS-S(O-octyl)-FLSPEHQRVQRKESKKPPAKLQPR-NH$_2$ (SEQ ID NO: 126);
H-PS-S(O-octyl)-FLSPEHQRVQQRKESKKPPA-NH$_2$ (SEQ ID NO: 127);
H-PS-S(O-octyl)-FLSPEHQRVQQRKES-NH$_2$ (SEQ ID NO: 128);
H-PS-[NH—CH(n-C$_{10}$H$_{21}$)—C(O)]-FLSPE-HQRVQQRKESKKPPAKLQPR-NH$_2$ (SEQ ID NO: 129);
H-PS-[NH—CH(n-C$_{10}$H$_{21}$)—C(O)]-FLSPE-HQRVQRKESKKPPAKLQPR-NH$_2$ (SEQ ID NO: 130);
H-[cACC]-S(O-octyl)-FLSPEHQRVQQRKESKKPPAK-LQPR-NH$_2$ (SEQ ID NO: 131);
H-PS-S(O-octyl)-FLSPEHSR-NH$_2$ (SEQ ID NO: 132);
H-PS-S(O-octyl)-FLSPEHSRVSSR-NH$_2$ (SEQ ID NO: 133); and
H-PS-S(O-octyl)-FLSPEHSRVSSRKESKKPPAKLSPR-NH$_2$ (SEQ ID NO: 134).

In the present description and claims, double parentheses "()" after the one-letter abbreviations for two amino acid residues in an amino acid sequence, e.g. "E( )" and "K( )", signify the presence of an intramolecular bond formed between the side-chains of the amino acid residues in question. In the case of "E( )" and "K( )", the intramolecular bond will typically be a lactam bridge.

Additional specific embodiments of compounds of the invention include compounds selected from the group consisting of:
H-PS-Dap(N-octanoyl)-FLSPEHQRVQQRKESKKPPAK-LQP-NH$_2$ (SEQ ID NO: 135);
H-PS-Dap(N-octanoyl)-FLSPEHQRVQQRKESKKP-PAKLQ-NH$_2$ (SEQ ID NO: 136);

H-PS-Dap(N-octanoyl)-FLSPEHQRVQQRKESKKP-PAKL-NH$_2$ (SEQ ID NO: 137);
H-PS-Dap(N-octanoyl)-FLSPEHQRVQQRKESKKPPAK-NH$_2$ (SEQ ID NO: 138);
H-PS-Dap(N-octanoyl)-FLSPEHQRVQQRKESKKPPA-NH$_2$ (SEQ ID NO: 139);
H-PS-Dap(N-octanoyl)-FLSPEHQRVQQRKESKKPP-NH$_2$ (SEQ ID NO: 140);
H-PS-Dap(N-octanoyl)-FLSPEHQRVQQRKESKKP-NH$_2$ (SEQ ID NO: 141);
H-PS-Dap(N-octanoyl)-FLSPEHQRVQQRKESKK-NH$_2$ (SEQ ID NO: 142);
H-PS-Dap(N-octanoyl)-FLSPEHQRVQQRKESK-NH$_2$ (SEQ ID NO: 143);
H-PS-Dap(N-octanoyl)-FLSPEHQRVQQRKES-NH$_2$ (SEQ ID NO: 144);
H-PS-Dap(N-octanoyl)-FLSPEHQRVQQRKE-NH$_2$ (SEQ ID NO: 145);
H-PS-Dap(N-octanoyl)-FLSPEHQRVQQRK-NH$_2$ (SEQ ID NO: 146);
H-PS-Dap(N-octanoyl)-FLSPEHQRVQQR-NH$_2$ (SEQ ID NO: 147);
H-PS-Dap(N-octanoyl)-FLSPEHQRVQQ-NH$_2$ (SEQ ID NO: 148);
H-PS-Dap(N-octanoyl)-FLSPEHQRVQ-NH$_2$ (SEQ ID NO: 149);
H-PS-Dap(N-octanoyl)-FLSPEHQRV-NH$_2$ (SEQ ID NO: 150);
H-PS-Dap(N-octanoyl)-FLSPEHQR-NH$_2$ (SEQ ID NO: 151);
H-PS-Dap(N-octanoyl)-FLSPEHQ-NH$_2$ (SEQ ID NO: 152);
H-PS-Dap(N-octanoyl)-FLSPEH-NH$_2$ (SEQ ID NO: 153);
H-PS-Dap(N-octanoyl)-FLSPE-NH$_2$ (SEQ ID NO: 154);
H-PS-Dap(N-octanoyl)-FLSP-NH$_2$ (SEQ ID NO: 155);
H-PS-Dap(N-octanoyl)-FLS-NH$_2$ (SEQ ID NO: 156);
H-PS-Dap(N-octanoyl)-FL-NH$_2$ (SEQ ID NO: 157);
H-PS-Dap(N-octanoyl)-FLSPEHSRVSSRKESKKP-PAKLSP-NH$_2$ (SEQ ID NO: 158);
H-PS-Dap(N-octanoyl)-FLSPEHSRVSSRKESKKP-PAKLS-NH$_2$ (SEQ ID NO: 159);
H-PS-Dap(N-octanoyl)-FLSPEHSRVSSRKESKKPPAKL-NH$_2$ (SEQ ID NO: 160);
H-PS-Dap(N-octanoyl)-FLSPEHSRVSSRKESKKPPAK-NH$_2$ (SEQ ID NO: 161);
H-PS-Dap(N-octanoyl)-FLSPEHSRVSSRKESKKPPA-NH$_2$ (SEQ ID NO: 162);
H-PS-Dap(N-octanoyl)-FLSPEHSRVSSRKESKKPP-NH$_2$ (SEQ ID NO: 163);
H-PS-Dap(N-octanoyl)-FLSPEHSRVSSRKESKKP-NH$_2$ (SEQ ID NO: 164);
H-PS-Dap(N-octanoyl)-FLSPEHSRVSSRKESKK-NH$_2$ (SEQ ID NO: 165);
H-PS-Dap(N-octanoyl)-FLSPEHSRVSSRKESK-NH$_2$ (SEQ ID NO: 166);
H-PS-Dap(N-octanoyl)-FLSPEHSRVSSRKES-NH$_2$ (SEQ ID NO: 167);
H-PS-Dap(N-octanoyl)-FLSPEHSRVSSRKE-NH$_2$ (SEQ ID NO: 168);
H-PS-Dap(N-octanoyl)-FLSPEHSRVSSRK-NH$_2$ (SEQ ID NO: 169);
H-PS-Dap(N-octanoyl)-FLSPEHSRVSSR-NH$_2$ (SEQ ID NO: 170);
H-PS-Dap(N-octanoyl)-FLSPEHSRVSS-NH$_2$ (SEQ ID NO: 171);
H-PS-Dap(N-octanoyl)-FLSPEHSRVS-NH$_2$ (SEQ ID NO: 172);
H-PS-Dap(N-octanoyl)-FLSPEHSRV-NH$_2$ (SEQ ID NO: 173);
H-PS-Dap(N-octanoyl)-FLSPEHSR-NH$_2$ (SEQ ID NO: 174);
H-PS-Dap(N-octanoyl)-FLSPEHS-NH$_2$ (SEQ ID NO: 175);
H-PS-[NH—CH(n-C$_{10}$H$_{21}$)—C(O)]-FLSPEHQRVQQRKESKKPPA-NH$_2$ (SEQ ID NO: 176);
H-PS-[NH—CH(n-C$_{10}$H$_{21}$)—C(O)]-FLSPEHQRVQQRKESKKPP-NH$_2$ (SEQ ID NO: 177);
H-PS-[NH—CH(n-C$_{10}$H$_{21}$)—C(O)]-FLSPEHQRVQQRKESKKP-NH$_2$ (SEQ ID NO: 178);
H-PS-[NH—CH(n-C$_{10}$H$_{21}$)—C(O)]-FLSPEHQRVQQRKESKK-NH$_2$ (SEQ ID NO: 179);
H-PS-[NH—CH(n-C$_{10}$H$_{21}$)—C(O)]-FLSPEHQRVQQRKESK-NH$_2$ (SEQ ID NO: 180);
H-PS-[NH—CH(n-C$_{10}$H$_{21}$)—C(O)]-FLSPEHQRVQQRKES-NH$_2$ (SEQ ID NO: 181);
H-PS-[NH—CH(n-C$_{10}$H$_{21}$)—C(O)]-FLSPEHQRVQQRKE-NH$_2$ (SEQ ID NO: 182);
H-PS-[NH—CH(n-C$_{10}$H$_{21}$)—C(O)]-FLSPEHQRVQQRK-NH$_2$ (SEQ ID NO: 183);
H-PS-[NH—CH(n-C$_{10}$H$_{21}$)—C(O)]-FLSPEHQRVQQR-NH$_2$ (SEQ ID NO: 184);
H-PS-[NH—CH(n-C$_{10}$H$_{21}$)—C(O)]-FLSPEHQRVQQ-NH$_2$ (SEQ ID NO: 185);
H-PS-[NH—CH(n-C$_{10}$H$_{21}$)—C(O)]-FLSPEHQRVQ-NH$_2$ (SEQ ID NO: 186);
H-PS-[NH—CH(n-C$_{10}$H$_{21}$)—C(O)]-FLSPEHQRV-NH$_2$ (SEQ ID NO: 187);
H-PS-[NH—CH(n-C$_{10}$H$_{21}$)—C(O)]-FLSPEHQR-NH$_2$ (SEQ ID NO: 188);
H-PS-[NH—CH(n-C$_{10}$H$_{21}$)—C(O)]-FLSPEHQ-NH$_2$ (SEQ ID NO: 189);
H-PS-[NH—CH(n-C$_{10}$H$_{21}$)—C(O)]-FLSPEH-NH$_2$ (SEQ ID NO: 190);
H-PS-[NH—CH(n-C$_{10}$H$_{21}$)—C(O)]-FLSPE-NH$_2$ (SEQ ID NO: 191);
H-PS-[NH—CH(n-C$_{10}$H$_{21}$)—C(O)]-FLSP-NH$_2$ (SEQ ID NO: 192);
H-PS-[NH—CH(n-C$_{10}$H$_{21}$)—C(O)]-FLS-NH$_2$ (SEQ ID NO: 193); and
H-PS-[NH—CH(n-C$_{10}$H$_{21}$)—C(O)]-FL-NH$_2$. (SEQ ID NO: 194).

Further specific embodiments of compounds of the invention include compounds selected from the group consisting of:
H-PS-Dap(N-octanoyl)-FLSPEHQRVQQRKESKKPPAK-LQP-OH (SEQ ID NO: 135);
H-PS-Dap(N-octanoyl)-FLSPEHQRVQQRKESKKP-PAKLQ-OH (SEQ ID NO: 136);
H-PS-Dap(N-octanoyl)-FLSPEHQRVQQRKESKKP-PAKL-OH (SEQ ID NO: 137);
H-PS-Dap(N-octanoyl)-FLSPEHQRVQQRKESKKPPAK-OH (SEQ ID NO: 138);
H-PS-Dap(N-octanoyl)-FLSPEHQRVQQRKESKKPPA-OH (SEQ ID NO: 139);
H-PS-Dap(N-octanoyl)-FLSPEHQRVQQRKESKKPP-OH (SEQ ID NO: 140);
H-PS-Dap(N-octanoyl)-FLSPEHQRVQQRKESKKP-OH (SEQ ID NO: 141);
H-PS-Dap(N-octanoyl)-FLSPEHQRVQQRKESKK-OH (SEQ ID NO: 142);
H-PS-Dap(N-octanoyl)-FLSPEHQRVQQRKESK-OH (SEQ ID NO: 143);
H-PS-Dap(N-octanoyl)-FLSPEHQRVQQRKES-OH (SEQ ID NO: 144);

H-PS-Dap(N-octanoyl)-FLSPEHQRVQQRKE-OH (SEQ ID NO: 145);
H-PS-Dap(N-octanoyl)-FLSPEHQRVQQRK-OH (SEQ ID NO: 146);
H-PS-Dap(N-octanoyl)-FLSPEHQRVQQR-OH (SEQ ID NO: 147);
H-PS-Dap(N-octanoyl)-FLSPEHQRVQQ-OH (SEQ ID NO: 148);
H-PS-Dap(N-octanoyl)-FLSPEHQRVQ-OH (SEQ ID NO: 149);
H-PS-Dap(N-octanoyl)-FLSPEHQRV-OH (SEQ ID NO: 150);
H-PS-Dap(N-octanoyl)-FLSPEHQR-OH (SEQ ID NO: 151);
H-PS-Dap(N-octanoyl)-FLSPEHQ-OH (SEQ ID NO: 152);
H-PS-Dap(N-octanoyl)-FLSPEH-OH (SEQ ID NO: 153);
H-PS-Dap(N-octanoyl)-FLSPE-OH (SEQ ID NO: 154);
H-PS-Dap(N-octanoyl)-FLSP-OH (SEQ ID NO: 155);
H-PS-Dap(N-octanoyl)-FLS-OH (SEQ ID NO: 156);
H-PS-Dap(N-octanoyl)-FL-OH (SEQ ID NO: 157);
H-PS-Dap(N-octanoyl)-FLSPEHSRVSSRKESKKPPAKLSP-OH (SEQ ID NO: 158);
H-PS-Dap(N-octanoyl)-FLSPEHSRVSSRKESKKPPAKLS-OH (SEQ ID NO: 159);
H-PS-Dap(N-octanoyl)-FLSPEHSRVSSRKESKKPPAKL-OH (SEQ ID NO: 160);
H-PS-Dap(N-octanoyl)-FLSPEHSRVSSRKESKKPPAK-OH (SEQ ID NO: 161);
H-PS-Dap(N-octanoyl)-FLSPEHSRVSSRKESKKPPA-OH (SEQ ID NO: 162);
H-PS-Dap(N-octanoyl)-FLSPEHSRVSSRKESKKPP-OH (SEQ ID NO: 163);
H-PS-Dap(N-octanoyl)-FLSPEHSRVSSRKESKKP-OH (SEQ ID NO: 164);
H-PS-Dap(N-octanoyl)-FLSPEHSRVSSRKESKK-OH (SEQ ID NO: 165);
H-PS-Dap(N-octanoyl)-FLSPEHSRVSSRKESK-OH (SEQ ID NO: 166);
H-PS-Dap(N-octanoyl)-FLSPEHSRVSSRKES-OH (SEQ ID NO: 167);
H-PS-Dap(N-octanoyl)-FLSPEHSRVSSRKE-OH (SEQ ID NO: 168);
H-PS-Dap(N-octanoyl)-FLSPEHSRVSSRK-OH (SEQ ID NO: 169);
H-PS-Dap(N-octanoyl)-FLSPEHSRVSSR-OH (SEQ ID NO: 170);
H-PS-Dap(N-octanoyl)-FLSPEHSRVSS-OH (SEQ ID NO: 171);
H-PS-Dap(N-octanoyl)-FLSPEHSRVS-OH (SEQ ID NO: 172);
H-PS-Dap(N-octanoyl)-FLSPEHSRV-OH (SEQ ID NO: 173);
H-PS-Dap(N-octanoyl)-FLSPEHSR-OH (SEQ ID NO: 174);
H-PS-Dap(N-octanoyl)-FLSPEHS-OH (SEQ ID NO: 175);
H-PS-[NH—CH(n-$C_{10}H_{21}$)—C(O)]-FLSPEHQRVQQRKESKKPPA-OH (SEQ ID NO: 176);
H-PS-[NH—CH(n-$C_{10}H_{21}$)—C(O)]-FLSPEHQRVQQRKESKKPP-OH (SEQ ID NO: 177);
H-PS-[NH—CH(n-$C_{10}H_{21}$)—C(O)]-FLSPEHQRVQQRKESKKP-OH (SEQ ID NO: 178);
H-PS-[NH—CH(n-$C_{10}H_{21}$)—C(O)]-FLSPEHQRVQQRKESKK-OH (SEQ ID NO: 179);
H-PS-[NH—CH(n-$C_{10}H_{21}$)—C(O)]-FLSPEHQRVQQRKESK-OH (SEQ ID NO: 180);
H-PS-[NH—CH(n-$C_{10}H_{21}$)—C(O)]-FLSPEHQRVQQRKES-OH (SEQ ID NO: 181);
H-PS-[NH—CH(n-$C_{10}H_{21}$)—C(O)]-FLSPEHQRVQQRKE-OH (SEQ ID NO: 182);
H-PS-[NH—CH(n-$C_{10}H_{21}$)—C(O)]-FLSPEHQRVQQRK-OH (SEQ ID NO: 183);
H-PS-[NH—CH(n-$C_{10}H_{21}$)—C(O)]-FLSPEHQRVQQR-OH (SEQ ID NO: 184);
H-PS-[NH—CH(n-$C_{10}H_{21}$)—C(O)]-FLSPEHQRVQQ-OH (SEQ ID NO: 185);
H-PS-[NH—CH(n-$C_{10}H_{21}$)—C(O)]-FLSPEHQRVQ-OH (SEQ ID NO: 186);
H-PS-[NH—CH(n-$C_{10}H_{21}$)—C(O)]-FLSPEHQRV-OH (SEQ ID NO: 187);
H-PS-[NH—CH(n-$C_{10}H_{21}$)—C(O)]-FLSPEHQR-OH (SEQ ID NO: 188);
H-PS-[NH—CH(n-$C_{10}H_{21}$)—C(O)]-FLSPEHQ-OH (SEQ ID NO: 189);
H-PS-[NH—CH(n-$C_{10}H_{21}$)—C(O)]-FLSPEH-OH (SEQ ID NO: 190);
H-PS-[NH—CH(n-$C_{10}H_{21}$)—C(O)]-FLSPE-OH (SEQ ID NO: 191);
H-PS-[NH—CH(n-$C_{10}H_{21}$)—C(O)]-FLSP-OH (SEQ ID NO: 192);
H-PS-[NH—CH(n-$C_{10}H_{21}$)—C(O)]-FLS-OH (SEQ ID NO: 193); and
H-PS-[NH—CH(n-$C_{10}H_{21}$)—C(O)]-FL-OH (SEQ ID NO: 194).

Pharmaceutically acceptable salts or solvates of any of the compounds of the invention, e.g., compounds within the latter two groups, are likewise within the scope of the present invention.

In each of the sequences described above, and in each sequence described herein, a C-terminal "—OH" moiety may be substituted for a C-terminal "—NH$_2$" moiety, and vice-versa.

Each of the specific compounds of the invention mentioned above, taken alone, constitutes an individual embodiment of a compound of the invention.

In the above, the abbreviations Ser(O-octanoyl) and Ser(O-octyl) for the residue in position 3 (as they occur, e.g., in the compound of the invention:
H-PS-S(O-octanoyl)-FLSPEHQRVQQRKESKKPPAKLQPR-OH (SEQ ID NO: 7); in the compound of the invention:
H-[DPro]-S-S(O-octanoyl)-FLSPEHQRVQQRKESKKPPAKLQPR-OH (SEQ ID NO: 8); in the compound of the invention:
H-PS-S(O-octanoyl)-FLSPEHQRV-K(hexadecanoyl)-QRKESKKPPAKLQPR-NH$_2$ (SEQ ID NO: 66); in the compound of the invention:
H-[DPro]-S-S(O-octanoyl)-FLSPEHQRV-K(hexadecanoyl)-QRKESKKPPAKLQPR-NH$_2$ (SEQ ID NO: 67); in the compound of the invention:
H-SS-S(O-octanoyl)-FLSPEHQRVQQRKESK-K(hexadecanoyl)-PPAKLQPR-NH$_2$ (SEQ ID NO: 73); in the compound of the invention:
H-[DPro]-S-S(O-octyl)-FLSPEHQRVQQRKESKKPPAKLQPR-OH (SEQ ID NO: 22); and in the compound of the invention:
H-Aib-S-S(O-octyl)-FLSPEHQRVQQRKESKKPPAKLQPR-OH) (SEQ ID NO: 23) refer to a modified serine residue in which the hydrogen atom of the side-chain hydroxy group in serine is replaced by an n-octanoyl group or n-octyl group, respectively. The abbreviation Dap(N-octanoyl) for the residue in position 3 (as it occurs, by way of example, in the compound of the invention:

H-PS-Dap(N-octanoyl)-FLSPEHQRVQQRKESKKPPAK-LQPR-OH (SEQ ID NO: 74); in the compound of the invention:
H-[DPro]-S-Dap(N-octanoyl)-FLSPEHQRVQQRKESK-KPPAKLQPR-OH (SEQ ID NO: 75); in the compound of the invention:
H-Mamb-Dap(N-octanoyl)-FLSPEHQRVQQRKES-K(hexadecanoyl)-KPPAKLQPROH (SEQ ID NO: 78); in the compound of the invention:
H-PS-Dap(N-octanoyl)-FLSPEHQRVQQRKESKKPPAK-LQPR-NH$_2$ (SEQ ID NO: 79); in the compound of the invention:
H-[DPro]-S-Dap(N-octanoyl)-FLSPEHQRVQQRKESK-KPPAKLQPR-NH$_2$ (SEQ ID NO: 80); in the compound of the invention:
H-PS-Dap(N-octanoyl)-FLSPEHSRVSSRKESKKPPAKL-SPR-NH$_2$ (SEQ ID NO: 82); and in the compound of the invention:
H-SS-Dap(N-octanoyl)-FLSPEHQRVQQRKESKKPPAK-LQPR-NH$_2$) (SEQ ID NO: 81); refers to a modified residue of the non-naturally occurring amino acid 2,3-diaminopropanoic acid in which the side-chain amino group (3-amino group) is N-acylated with an n-octanoyl group.

In further aspects of the invention, in addition to those residues specified above in relation to position $X^1$, additional amino acid residues which may be of relevance as $X^1$ residues in compounds of the invention include, but are not limited to, Bal, βPro and Lys.

In still further aspects of the invention, in addition to those residues specified above in relation to the positions $X^{10}$, $X^{13}$, $X^{14}$ and $X^{26}$, the amino acid residue at one or more of those four positions may, independently, be selected from the group consisting of Glu, Leu, Lys, Ser and Arg.

The peptide sequence Z in formula I may be considered to consist of up to 28 positions, designated $X^1$ to $X^{28}$. The amino acid residues at positions $X^4$ to $X^7$, $X^9$, $X^{17}$, $X^{18}$, $X^{21}$ to $X^{23}$, $X^{25}$ and $X^{27}$, when present, are fixed as set out in formula Ia. The amino acid residues at positions $X^1$ to $X^3$, $X^8$, $X^{10}$ to $X^{16}$, $X^{19}$, $X^{20}$, $X^{24}$, $X^{26}$ and $X^{28}$, when present, may vary within the parameters described in this specification.

In certain embodiments described by formula Ib, positions $X^8$, $X^{15}$ and $X^{28}$ are also fixed.

In some aspects, Z is full-length. That is to say, at least positions $X^1$ to $X^{13}$ and $X^{15}$ to $X^{28}$ are present. Position $X^{14}$ may independently be present or absent.

In yet further aspects, the invention also provides compounds having an amino acid sequence (Z in formula I above) that is truncated (shortened), from the C-terminus, relative to the full length of the sequence Z in compounds of the invention of formula I as disclosed above. In some embodiments, the truncated compounds are truncated by up to 23, e.g., up to 22, residues counting from the C-terminus of a compound of the invention of formula I as disclosed above (which in its longest form as disclosed above has an Arg residue at the C-terminus). Thus, such compounds may be truncated by 1, 2, 3, 4, 5, 6, 7, 8, 9, 10, 11, 12, 13, 14, 15, 16, 17, 18, 19, 20, 21, 22, or 23 amino acid residues, counting from the C-terminus of a compound of the invention of formula I as disclosed above.

Thus, the peptide sequence Z will always comprise residue positions $X^1$ to $X^5$, and may comprise $X^1$ to $X^6$, $X^1$ to $X^7$, $X^1$ to $X^8$, $X^1$ to $X^9$, $X^1$ to $X^{10}$, $X^1$ to $X^{11}$, $X^1$ to $X^{12}$, $X^1$ to $X^{13}$, $X^1$ to $X^{14}$, $X^1$ to $X^{15}$, $X^1$ to $X^{16}$, $X^1$ to $X^{17}$, $X^1$ to $X^{18}$, $X^1$ to $X^{19}$, $X^1$ to $X^{20}$, $X^1$ to $X^{21}$, $X^1$ to $X^{22}$, $X^1$ to $X^{23}$, $X^1$ to $X^{24}$, $X^1$ to $X^{25}$, $X^1$ to $X^{26}$, $X^1$ to $X^{27}$, or $X^1$ to $X^{28}$. In any of these, position $X^{14}$ may be independently absent.

Without wishing to be bound by theory, the more highly truncated certain compounds of the invention are, the more advantageous they may be with regard to ghrelin receptor agonist activity to have an —NH$_2$ group rather than an —OH group at the C-terminus thereof ($R^2$ in compounds of the invention of formula I as already disclosed above).

In some embodiments, the compounds of the invention may have at least 40%, e.g., at least 45%, 50%, 55%, 60%, 65%, 70%, 75%, 80%, 85%, 90%, 95%, 96%, 97%, 98%, or 99%, 99.5%, or 99.9% amino acid sequence identity to native human ghrelin. The percentage identity is calculated only over the length of overlap between the relevant compound and the native human ghrelin sequence. Thus, for example, a compound consisting solely of positions $X^1$ to $X^{14}$ of native human ghrelin would considered to have 100% identity to ghrelin, not 50%. (Needless to say, such a compound is not a compound of the invention.) For the avoidance of doubt, a modified residue (such as a Lys residue carrying a lipophilic substituent) is considered to be different to the unmodified form for the purposes of determining sequence identity. If position 14 is absent, that should not be taken into account in the assessment of sequence identity.

As an alternative to percentage sequence identity, it may be convenient to consider the number of residues in a given compound which are different from the corresponding residues in native human ghrelin.

The compounds of the invention differ from native human ghrelin at least at positions 1 and 3. They may have a maximum of 3 differences, a maximum of 4 differences, a maximum of 5 differences, a maximum of 6 differences, a maximum of 7 differences, a maximum of 8 differences, a maximum of 9 differences, a maximum of 10 differences, a maximum of 11 differences, a maximum of 12 differences, a maximum of 13 differences, a maximum of 14 differences, a maximum of 15 differences or a maximum of 16 differences compared to native human ghrelin, depending on the length of the compound itself, including any absence of position 14. It may be desirable that one of these differences is a Lys modified by acylation as described herein.

Thus, a compound consisting of positions $X^1$ to $X^5$, $X^1$ to $X^6$, or $X^1$ to $X^7$ has a maximum of 3 residues which are different to the corresponding residues in human ghrelin.

A compound consisting of positions $X^1$ to $X^8$ or $X^1$ to $X^9$ may have a maximum of 3 or a maximum of 4 residues which are different to the corresponding residues in human ghrelin.

A compound consisting of positions $X^1$ to $X^{10}$ may have a maximum of 3, a maximum of 4 or a maximum of 5 residues which are different to the corresponding residues in human ghrelin.

A compound consisting of positions $X^1$ to $X^1$ may have a maximum of 3, a maximum of 4, a maximum of 5, or a maximum of 6 residues which are different to the corresponding residues in human ghrelin.

A compound consisting of positions $X^1$ to $X^{12}$ may have a maximum of 3, a maximum of 4, a maximum of 5, a maximum of 6, or a maximum of 7 residues which are different to the corresponding residues in human ghrelin.

A compound consisting of positions $X^1$ to $X^{13}$ may have a maximum of 3, a maximum of 4, a maximum of 5, a maximum of 6, a maximum of 7, or a maximum of 8 residues which are different to the corresponding residues in human ghrelin.

A compound consisting of positions $X^1$ to $X^{14}$ may have a maximum of 3, a maximum of 4, a maximum of 5, a maximum of 6, a maximum of 7, a maximum of 8, or a maximum of 9 residues which are different to the corresponding residues in human ghrelin.

A compound consisting of positions $X^1$ to $X^{15}$ may have a maximum of 3, a maximum of 4, a maximum of 5, a maximum of 6, a maximum of 7, a maximum of 8, a maximum of 9, or a maximum of 10 residues which are different to the corresponding residues in human ghrelin.

A compound consisting of positions $X^1$ to $X^{16}$, $X^1$ to $X^{17}$, or $X^1$ to $X^{18}$ may have a maximum of 3, a maximum of 4, a maximum of 5, a maximum of 6, a maximum of 7, a maximum of 8, a maximum of 9, a maximum of 10, or a maximum of 11 residues which are different to the corresponding residues in human ghrelin.

A compound consisting of positions $X^1$ to $X^{19}$ may have a maximum of 3, a maximum of 4, a maximum of 5, a maximum of 6, a maximum of 7, a maximum of 8, a maximum of 9, a maximum of 10, a maximum of 11, or a maximum of 12 residues which are different to the corresponding residues in human ghrelin.

A compound consisting of positions $X^1$ to $X^{20}$, $X^1$ to $X^{21}$, or $X^1$ to $X^{22}$ or $X^1$ to $X^{23}$, may have a maximum of 3, a maximum of 4, a maximum of 5, a maximum of 6, a maximum of 7, a maximum of 8, a maximum of 9, a maximum of 10, a maximum of 11, a maximum of 12, or a maximum of 13 residues which are different to the corresponding residues in human ghrelin.

A compound consisting of positions $X^1$ to $X^{24}$ or $X^1$ to $X^{25}$ may have a maximum of 3, a maximum of 4, a maximum of 5, a maximum of 6, a maximum of 7, a maximum of 8, a maximum of 9, a maximum of 10, a maximum of 11, a maximum of 12, a maximum of 13, or a maximum of 14 residues which are different to the corresponding residues in human ghrelin.

A compound consisting of positions $X^1$ to $X^{26}$ or $X^1$ to $X^{27}$ may have a maximum of 3, a maximum of 4, a maximum of 5, a maximum of 6, a maximum of 7, a maximum of 8, a maximum of 9, a maximum of 10, a maximum of 11, a maximum of 12, a maximum of 13, a maximum of 14, or a maximum of 15 residues which are different to the corresponding residues in human ghrelin.

A compound consisting of positions $X^1$ to $X^{28}$ may have a maximum of 3, a maximum of 4, a maximum of 5, a maximum of 6, a maximum of 7, a maximum of 8, a maximum of 9, a maximum of 10, a maximum of 11, a maximum of 12, a maximum of 13, a maximum of 14, a maximum of 15, or a maximum of 16 residues which are different to the corresponding residues in human ghrelin.

For the purposes of this assessment, absence of position $X^{14}$ is considered a difference relative to human ghrelin.

In some embodiments, the polypeptides of the invention may comprise the amino acid sequence of any one of Compound Nos: 5-23 (see Table 1, below), or a functional variant thereof that has at least about 70%, 75%, 80%, 85%, 90%, 95%, 97%, 98%, 99% or 99.5% sequence identity to ghrelin. A functional variant of a polypeptide of the invention may have at least, e.g., 50%, 55%, 60%, 65%, 70%, 75%, 80%, 85%, 90%, 95%, 97%, 98%, 99%, 99.5%, or 100% of at least one biological activity of a native ghrelin polypeptide. For example, in some embodiments, a polypeptide of the invention may comprise one or more amino acid substitutions, e.g., conservative amino acid substitutions, and bind to and/or activate the ghrelin receptor by at least 50% compared to the binding and/or activation by native human ghrelin.

The term "conservative substitution" as used herein denotes that one or more amino acids are replaced by another, biologically similar residue. Examples include substitution of amino acid residues with similar characteristics, e.g. small amino acids, acidic amino acids, polar amino acids, basic amino acids, hydrophobic amino acids and aromatic amino acids. See, for example, the table below. An example of a conservative substitution with a residue normally not found in endogenous, mammalian peptides and proteins is the conservative substitution of Arg or Lys with, for example, ornithine, canavanine, aminoethylcysteine or another basic amino acid. For further information concerning phenotypically silent substitutions in peptides and proteins, see, e.g., Bowie et al., Science 247, 1306-1310, 1990. In the scheme below are conservative substitutions of amino acids grouped by physicochemical properties. I: neutral, hydrophilic, II: acids and amides, III: basic, IV: hydrophobic, V: aromatic, bulky amino acids.

| I | II | III | IV | V |
|---|----|-----|----|---|
| A | N | H | M | F |
| S | D | R | L | Y |
| T | E | K | I | W |
| P | Q |   | V |   |
| G |   |   | C |   |

In some embodiments, the polypeptide of the invention may comprise functional fragments or variants thereof that have, at most, 20, 15, 10, 9, 8, 7, 6, 5, 4, 3, 2, or 1 amino acid substitutions compared to a wild-type or native human ghrelin sequence. The polypeptide of the invention may further be with or without a signal sequence.

In some embodiments, a polypeptide of the invention shares at least 95% amino acid sequence identity to any one of Compound Nos: 5-21.

As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type N(R1)(R2)(R3)(R4)+, wherein R1, R2, R3 and R4 independently will typically designate hydrogen, optionally substituted $C_{1-6}$-alkyl groups or optionally substituted $C_{2-6}$-alkenyl groups. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977).

The term "solvate" in the context of the present invention refers to a complex of defined stoichiometry formed between a solute (in casu, a peptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

Some embodiments of the invention relate to a peptide compound or pharmaceutically acceptable salt or solvate thereof according to the invention for use as or for the manufacture or preparation of a pharmaceutical composition, or for the use of a peptide compound or pharmaceutically acceptable salts or solvates thereof in methods of treating or preventing a variety of conditions, diseases, disorders, and syndromes, for example, cachexia, low body weight, loss of body weight, low or decreased appetite, low muscle mass, effects of gastrectomy or vagectomy, anorexia, bulimia, chronic obstructive pulmonary disease, growth hormone deficiency, cardiovascular indications (e.g., low blood flow, low cardiac output, and high blood pressure), osteoporosis, arthritis pain, inflammatory disorders (e.g., arthritis and systemic lupus erythematosus) and gastrointestinal disorders including but not limited to gastroparesis, post-operative ileus, inflammatory disorders such as colitis (e.g., ulcerative colitis), gut barrier dysfunction, inflammatory bowel disease (IBD), Crohn's disease, and ischemia reperfusion injury.

In some embodiments, a peptide compound of the invention is a peptide compound for use in treating a subject in need thereof.

In further embodiments, the peptide compound of the invention is a peptide compound for use in increasing, in a subject in need thereof, food intake and/or body weight.

In further embodiments, the peptide compound of the invention is a peptide compound for inducing, in a subject in need thereof, the production of growth hormone.

In further embodiments, the peptide compound of the invention is a peptide compound for increasing, in a subject in need thereof, blood flow (e.g., colonic blood flow) and/or cardiac output.

In further embodiments, the peptide compound of the invention is a peptide compound for decreasing, in a subject in need thereof, blood pressure.

In further embodiments, the peptide compound of the invention is a peptide compound for inducing, in a subject in need thereof, increased motility of the gastrointestinal tract.

In further embodiments, the peptide compound of the invention is a peptide compound for decreasing, in a subject in need thereof, inflammation.

In some embodiments, a pharmaceutical composition of the invention is a pharmaceutical composition for use in treating a subject in need thereof.

In further embodiments, the pharmaceutical composition of the invention is a pharmaceutical composition for use in treating cachexia and/or chronic obstructive pulmonary disease.

In further embodiments, the pharmaceutical composition of the invention is a pharmaceutical composition for use in increasing, in a subject in need thereof, food intake and/or body weight.

In further embodiments, the pharmaceutical composition of the invention is a pharmaceutical composition for inducing, in a subject in need thereof, the production of growth hormone.

In further embodiments, the pharmaceutical composition of the invention is a pharmaceutical composition for increasing, in a subject in need thereof, blood flow (e.g., colonic blood flow) and/or cardiac output.

In further embodiments, the pharmaceutical composition of the invention is a pharmaceutical composition for decreasing, in a subject in need thereof, blood pressure.

In further embodiments, the pharmaceutical composition of the invention is a pharmaceutical composition for inducing, in a subject in need thereof, increased motility of the gastrointestinal tract.

In further embodiments, the pharmaceutical composition of the invention is a pharmaceutical composition for decreasing, in a subject in need thereof, inflammation.

Further embodiments of the invention relate to the use of a peptide compound of the invention in the manufacture or preparation of a pharmaceutical composition for the treatment, in a subject in need thereof, of one or more of the conditions, diseases, disorders, and syndromes disclosed herein.

Among related, additional embodiments of the invention are corresponding methods of treatment of conditions, diseases or disorders among those disclosed herein. Thus, exemplary embodiments of the invention relate to a method for treatment, in a subject in need thereof, of one or more of the conditions, diseases, disorders, and syndromes disclosed herein, the method comprising administering to the subject a therapeutically effective amount of a peptide compound or pharmaceutically acceptable salt or solvate thereof according to the invention.

Other embodiments of the invention relate to a method for increasing food intake and/or body weight in a subject in need thereof, the method comprising administering to the subject a therapeutically effective amount of a peptide compound or pharmaceutically acceptable salt or solvate thereof according to the invention.

Other embodiments of the invention relate to a method for inducing the production of growth hormone in a subject in need thereof, the method comprising administering to the subject a therapeutically effective amount of a peptide compound or pharmaceutically acceptable salt or solvate thereof according to the invention.

Other embodiments of the invention relate to a method for increasing blood flow (e.g., colonic blood flow) and/or cardiac output in a subject in need thereof, the method comprising administering to the subject a therapeutically effective amount of a peptide compound or pharmaceutically acceptable salt or solvate thereof according to the invention.

Other embodiments of the invention relate to a method for decreasing blood pressure in a subject in need thereof, the method comprising administering to the subject a therapeutically effective amount of a peptide compound or pharmaceutically acceptable salt or solvate thereof according to the invention.

Other embodiments of the invention relate to a method for increasing motility of the gastrointestinal tract in a subject in need thereof, the method comprising administering to the subject a therapeutically effective amount of a peptide compound or pharmaceutically acceptable salt or solvate thereof according to the invention.

Other embodiments of the invention relate to a method for decreasing inflammation in a subject in need thereof, the method comprising administering to the subject a therapeutically effective amount of a peptide compound or pharmaceutically acceptable salt or solvate thereof according to the invention.

In some embodiments, a pharmaceutical composition of the invention is a pharmaceutical composition for use in preventing a disease, condition, or syndrome in a subject in need thereof.

In some embodiments, a pharmaceutical composition of the invention is a pharmaceutical composition for use in preventing, in a subject in need thereof, cachexia, and/or chronic obstructive pulmonary disease.

In further embodiments, the pharmaceutical composition of the invention is a pharmaceutical composition for use in preventing, in a subject in need thereof, decreased food intake and/or loss of body weight.

In further embodiments, the pharmaceutical composition of the invention is a pharmaceutical composition for preventing, in a subject in need thereof, a deficiency in the production of growth hormone.

In further embodiments, the pharmaceutical composition of the invention is a pharmaceutical composition for preventing, in a subject in need thereof, low blood flow (e.g., low colonic blood flow) and/or low cardiac output.

In further embodiments, the pharmaceutical composition of the invention is a pharmaceutical composition for preventing, in a subject in need thereof, elevated blood pressure.

In further embodiments, the pharmaceutical composition of the invention is a pharmaceutical composition for preventing, in a subject in need thereof, reduced motility of the gastrointestinal tract.

In further embodiments, the pharmaceutical composition of the invention is a pharmaceutical composition for preventing, in a subject in need thereof, inflammation.

Further embodiments of the invention relate to the use of a peptide compound of the invention in the manufacture or preparation of a pharmaceutical composition for the prevention, in a subject in need thereof, of one or more of the conditions, diseases, disorders, and syndromes disclosed herein.

Among related, additional embodiments of the invention are corresponding methods of preventing conditions, diseases, disorders, and syndromes among those disclosed herein. Thus, exemplary embodiments of the invention relate to a method for prevention, in a subject in need thereof, of one or more of the conditions, diseases, disorders, and syndromes disclosed herein, the method comprising administering to the subject a therapeutically effective amount of a peptide compound or pharmaceutically acceptable salt or solvate thereof according to the invention.

Other embodiments of the invention relate to a method for preventing decreased food intake and/or loss of body weight in a subject in need thereof, the method comprising administering to the subject a therapeutically effective amount of a peptide compound or pharmaceutically acceptable salt or solvate thereof according to the invention.

Other embodiments of the invention relate to a method for preventing reduced production of growth hormone in a subject in need thereof, the method comprising administering to the subject a therapeutically effective amount of a peptide compound or pharmaceutically acceptable salt or solvate thereof according to the invention.

Other embodiments of the invention relate to a method for preventing decreased blood flow (e.g., colonic blood flow) and/or low cardiac output in a subject in need thereof, the method comprising administering to the subject a therapeutically effective amount of a peptide compound or pharmaceutically acceptable salt or solvate thereof according to the invention.

Other embodiments of the invention relate to a method for preventing high blood pressure in a subject in need thereof, the method comprising administering to the subject a therapeutically effective amount of a peptide compound or pharmaceutically acceptable salt or solvate thereof according to the invention.

Other embodiments of the invention relate to a method for preventing decreased motility of the gastrointestinal tract in a subject in need thereof, the method comprising administering to the subject a therapeutically effective amount of a peptide compound or pharmaceutically acceptable salt or solvate thereof according to the invention.

Other embodiments of the invention relate to a method for preventing inflammation in a subject in need thereof, the method comprising administering to the subject a therapeutically effective amount of a peptide compound or pharmaceutically acceptable salt or solvate thereof according to the invention.

Other embodiments of the invention relate to veterinarian use (e.g., use in a non-human animal) of a peptide compound or pharmaceutically acceptable salt or solvate thereof according to the invention.

The term "therapeutically effective amount" as used herein in the context of the above-described methods of treatment, prevention or other therapeutic interventions according to the invention refers to an amount that is sufficient to cure, ameliorate, alleviate or partially arrest the clinical manifestations of the particular disease, disorder or condition that is the object of the treatment, prevention or other therapeutic intervention in question e.g. as measured by established clinical endpoints or other biomarkers (established or experimental). A therapeutically relevant amount may be determined empirically by one skilled in the art based on the indication being treated or prevented and the subject to whom the therapeutically relevant amount is being administered. For example, the skilled worker may measure one or more of the clinically relevant indicators of bioactivity described herein, e.g., growth hormone levels, nutrient levels, and inflammatory cytokine levels. The skilled worker may determine a clinically relevant amount through in vitro or in vivo measurements. Other exemplary measures include weight loss, food intake, and appetite.

An amount adequate to accomplish any one or more of these effects is defined as a therapeutically effective amount. The administered amount and the method of administration can be tailored to achieve optimal efficacy. An amount effective for a given purpose will depend, inter alia, on the severity of the disease, disorder or condition that is the object of the particular treatment, prevention or other therapeutic intervention, on the body weight and general condition of the subject in question, on diet, on possible concurrent medication, and on other factors well known to those skilled in the medical arts. Determination of an appropriate dosage size and dosing regimen most appropriate for administration of a peptide compound or pharmaceutically acceptable salt or solvate thereof according to the invention to a human may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are well known to the skilled person.

The terms "treatment" and grammatical variants thereof (e.g. "treated", "treating", "treat") as employed in the present context refer to an approach for obtaining beneficial or desired clinical results. For the purposes of this invention, beneficial or desired clinical results include, but are not limited to, alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms (e.g., weight loss) relative to the absence of treatment, and is not necessarily meant to imply complete cessation of the relevant disease, disorder or condition.

The terms "preventing" and grammatical variants thereof (e.g., "prevented", "preventing", "prevent") as employed in the present context refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" thus includes slowing the onset of disease relative to the absence of treatment, and is not necessarily meant to imply permanent prevention of the relevant disease, disorder or condition.

In some embodiments of the invention, a subject in need of the particular treatment or other therapeutic intervention referred to in connection with the various aspects of the invention described above is a mammal.

In some embodiments, a mammal is a livestock animal such as, but not limited to, a cow, a sheep, a pig, a goat, or a horse. In some embodiments, a mammal is a pet such as, but not limited to, a cat or a dog. In some embodiments, a mammal is, e.g., a mouse, a rat, a rabbit, a monkey, or a chimpanzee. In some embodiments, a mammal is a non-human mammal. In some embodiments, a mammal is a non-human primate.

In further embodiments, the mammal is a human.

Additional embodiments of the invention relate to pharmaceutical compositions comprising a peptide compound, or a pharmaceutically acceptable salt or solvate thereof, according to the invention, together with a pharmaceutically acceptable carrier, excipient or vehicle.

Synthesis of Peptide Compounds

The peptide compounds of the invention may be manufactured by standard peptide synthetic methods, by use of recombinant expression systems, or by any other suitable method. Thus, the compounds may be synthesized in a number of ways, including, e.g., methods comprising:
(a) synthesizing the peptide compound by standard solid-phase or liquid-phase methodology, either stepwise or by fragment assembly, and isolating and purifying the final peptide compound product;
(b) expressing a nucleic acid construct that encodes the peptide compound or a fragment or precursor thereof in a host cell and recovering the expression product from the host cell culture; or
(c) effecting cell-free in vitro expression of a nucleic acid construct encoding the peptide compound or a fragment or precursor thereof, and recovering the expression product; or by any combination of the methods of (a), (b) or (c) to obtain fragments of the peptide compound, subsequently joining (e.g., ligating) the fragments to obtain the peptide compound, and recovering the peptide compound.

The method of synthesis may comprise the step of chemically modifying one of more amino acid side chains in a precursor peptide to yield a compound of the invention. Such modification may, for example, introduce a non-naturally occurring amino acid, convert one or more amino acids into non-naturally occurring amino acids, introduce an intramolecular bridge between two amino acid side chains, e.g. by forming a lactam ring between a Glu and a Lys residue, or introduce a lipophilic substituent at a lysine residue. It may be preferable to synthesize the peptide compounds of the invention by means of solid-phase or liquid-phase peptide synthesis. In this context, reference may be made to WO 98/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present invention also provides methods for producing a polypeptide of the invention according to above recited methods; a nucleic acid molecule encoding part or all of a polypeptide of the invention or a precursor thereof, a vector comprising at least one nucleic acid of the invention, expression vectors comprising at least one nucleic acid of the invention capable of producing a polypeptide of the invention when introduced into a host cell, and a host cell comprising a nucleic acid molecule, vector or expression vector of the invention.

It will be understood that a nucleic acid will typically only be capable of encoding a polypeptide of the invention when the polypeptide sequence Z consists entirely of the 20 naturally occurring amino acids.

Lipophilic Substituents

As explained above, one or more positions in the formulae Ia, Ib and Ic may independently be replaced by a Lys residue conjugated (i.e. covalently attached) to a lipophilic substituent.

Without wishing to be bound by any particular theory, it is thought that the lipophilic substituent binds albumin in the blood stream, thus shielding the compounds of the invention from enzymatic degradation and thereby enhancing the half-life of the compounds. It may also modulate the potency of the compound, e.g. with respect to the glucagon receptor and/or the GLP-1 receptor.

The positions in question may be any one or more of $X^8$, $X^{10}$, $X^{11}$, $X^{13}$, $X^{14}$, $X^{16}$, $X^{19}$, $X^{20}$, $X^{24}$, $X^{26}$ and (in some formulae) $X^{28}$. In certain embodiments, only one such position comprises a Lys conjugated to a lipophilic substituent. In other embodiments, two amino acid side chains are each conjugated to a lipophilic substituent. In yet further embodiments, three or even more amino acid side chains are each conjugated to a lipophilic substituent. When a compound contains two or more lipophilic substituents, they may be the same or different. Typically, there are no more than two, or no more than three such positions in any given molecule.

The lipophilic substituent comprises or consists of a lipophilic moiety $Z^1$ which may be covalently bonded directly to an atom in the amino acid side chain, or alternatively may be conjugated to the amino acid side chain by a spacer $Z^2$.

The term "conjugated" is used here to describe the physical attachment of one identifiable chemical moiety to another, and the structural relationship between such moieties. It should not be taken to imply any particular method of synthesis.

The lipophilic moiety may be attached to the amino acid side chain or to the spacer via an ester, a sulphonyl ester, a thioester, an amide, a carbamate, a urea or a sulphonamide.

Accordingly it will be understood that preferably the lipophilic substituent includes an acyl group, a sulphonyl group, an N atom, an O atom or an S atom which forms part of the ester, sulphonyl ester, thioester, amide or sulphonamide. Preferably, an acyl group in the lipophilic substituent forms part of an amide or ester with the amino acid side chain or the spacer.

The lipophilic moiety may include a hydrocarbon chain having 4 to 30 C atoms. Preferably it has at least 8 or 12 C atoms, and preferably it has 24 C atoms or fewer, or 20 C atoms or fewer. The hydrocarbon chain may be linear or branched and may be saturated or unsaturated. It will be understood that the hydrocarbon chain is preferably substituted with a moiety which forms part of the attachment to the amino acid side chain or the spacer, for example an acyl group, a sulphonyl group, an N atom, an O atom or an S atom. Most preferably the hydrocarbon chain is substituted with acyl, and accordingly the hydrocarbon chain may be part of an alkanoyl group, for example palmitoyl, caproyl, lauroyl, myristoyl or stearoyl.

Accordingly, the lipophilic moiety may have the formula shown below:

A may be, for example, an acyl group, a sulphonyl group, NH, N-alkyl, an O atom or an S atom, preferably acyl. n is an integer from 3 to 29, preferably from 7 to 25, more preferred 11 to 21, even more preferred 15 to 19.

The hydrocarbon chain may be further substituted. For example, it may be further substituted with up to three substituents selected from $NH_2$, OH and COOH, especially at the free end of the molecule distal from the spacer or peptide. For example, it may comprise a free carboxylic acid group.

If the hydrocarbon chain is further substituted, preferably it is further substituted with only one substituent. Alternatively or additionally, the hydrocarbon chain may include a cycloalkane or heterocycloalkane, for example as shown below:

Preferably the cycloalkane or heterocycloalkane is a six-membered ring. Most preferably, it is piperidine.

Alternatively, the lipophilic moiety may be based on a cyclopentanophenanthrene skeleton, which may be partially or fully unsaturated, or saturated. The carbon atoms in the skeleton each may be substituted with Me or OH. For example, the lipophilic substituent may be cholyl, deoxycholyl or lithocholyl.

As mentioned above, the lipophilic moiety may be conjugated to the amino acid side chain by a spacer. When present, the spacer is attached to the lipophilic moiety and to the amino acid side chain. The spacer may be attached to the lipophilic moiety and to the amino acid side chain independently by an ester, a sulphonyl ester, a thioester, an amide, a carbamate, a urea or a sulphonamide. Accordingly, it may include two moieties independently selected from acyl, sulphonyl, an N atom, an O atom or an S atom. The spacer may have the formula:

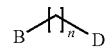

wherein B and D are each independently selected from acyl, sulphonyl, NH, N-alkyl, an O atom and an S atom, preferably from acyl and NH. Preferably, n is an integer from 1 to 10, preferably from 1 to 5. The spacer may be further substituted with one or more substituents selected from $C_{0-6}$ alkyl, $C_{0-6}$ alkyl amine, $C_{0-6}$ alkyl hydroxy and $C_{0-6}$ alkyl carboxy.

Alternatively, the spacer may have two or more repeat units of the formula above. B, D and n are each selected independently for each repeat unit. Adjacent repeat units may be covalently attached to each other via their respective B and D moieties. For example, the B and D moieties of the adjacent repeat units may together form an ester, a sulphonyl ester, a thioester, an amide or a sulphonamide. The free B and D units at each end of the spacer are attached to the amino acid side chain and the lipophilic moiety as described above.

Preferably the spacer has five or fewer, four or fewer or three or fewer repeat units. Most preferably the spacer has two repeat units, or is a single unit.

The spacer (or one or more of the repeat units of the spacer, if it has repeat units) may be, for example, a natural or unnatural amino acid. It will be understood that for amino acids having functionalised side chains, B and/or D may be a moiety within the side chain of the amino acid. The spacer may be any naturally occurring or unnatural amino acid. For example, the spacer (or one or more of the repeat units of the spacer, if it has repeat units) may be Gly, Pro, Ala, Val, Leu, Ile, Met, Cys, Phe, Tyr, Trp, His, Lys, Arg, Gin, Asn, ⊐-Glu, ⊐-Glu, Asp, Ser Thr, Gaba (gamma-aminobutyric acid), Aib, Bal (also referred to as ⊐-Ala), 5-aminopentanoyl, 6-aminohexanoyl, 7-aminoheptanoyl, 8-aminooctanoyl, 9-aminononanoyl or 10-aminodecanoyl.

For example, the spacer may be a single amino acid selected from ⊐⊐-Glu, Gaba, Bal and ⊐-Glu.

A lipophilic substituent may be conjugated to any amino acid side chain in a compound of the invention. Preferably, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gin, His, Lys, Arg, Ser, Thr, Tyr, Trp, Cys or Dbu, Dap or Orn. Preferably, the lipophilic substituent is conjugated to Lys. An amino acid shown as Lys in the formulae provided herein may be replaced by, e.g., Dbu, Dap or Orn where a lipophilic substituent is added.

An example of a lipophilic substituent comprising lipophilic moiety and spacer is shown in the formula below:

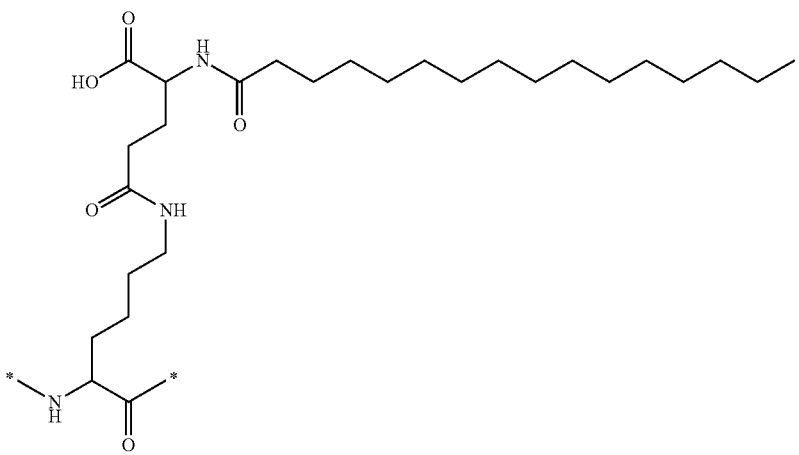 [SMILES: CCCCCCCCCCCCCCCC(=O)NC(CCC(=O)NCCCCC(NC)C(C)=O)C(=O)O]

Here, a Lys residue in the compound of the present invention is covalently attached to ⊐-Glu (the spacer) via an amide moiety. Palmitoyl (i.e. hexadecanoyl) is covalently attached to the ⊐-Glu spacer via an amide moiety, thus creating a hexadecanoyl-isoGlu group.

Nucleic Acids and Expression Methods

For recombinant expression, nucleic acids encoding entire peptides conjugates, precursors, or fragments thereof will normally be inserted in suitable vectors to form cloning or expression vectors; such novel vectors are also part of the invention. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) of the invention are capable of autonomous replication, thereby enabling high copy-numbers for the purposes of high-level expression or high-level replication for subsequent cloning.

In general outline, an expression vector comprises the following features in the 5'→3' direction and in operable linkage: a promoter for driving expression of the nucleic acid fragment of the invention, optionally a nucleic acid sequence encoding a leader peptide enabling secretion (to the extracellular phase or, where applicable, into the periplasma), the nucleic acid fragment encoding the peptide of the invention, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors are used to transform host cells to produce the required compound. Such transformed cells can be cultured cells or cell lines used for propagation of the nucleic acid fragments and vectors, or used for recombinant production of the peptides.

Preferred host cells are micro-organisms such as bacteria [such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (e.g., *Saccharomyces cerevisiae* and *Pichia pastoris*), and protozoans. Alternatively, the transformed cells may be derived from a multicellular organism, i.e. it may be fungal cell, an insect cell, an algal cell, a plant cell, or an animal cell such as a mammalian cell. For the purposes of cloning and/or optimised expression it is preferred that the transformed cell is capable of replicating the encoding nucleic acid. Cells expressing the nucleic fragment are useful embodiments of the invention; they can be used for small-scale or large-scale preparation of the peptides of the invention.

When producing peptides of the invention or fragments or precursors thereof by means of transformed cells, it is convenient, although far from essential, that the expression product is secreted into the culture medium.

Therapeutic Uses

The peptide compounds of the invention have the surprising benefit of a significantly longer half-life as compared to a native human ghrelin polypeptide, and exhibit reduced degradation as compared to a native human ghrelin polypeptide. Thus, the peptide compounds of the invention are well suited for use in the treatment of a variety of conditions, diseases, disorders, and syndromes.

Uses of the peptide compounds of the invention also encompass uses of pharmaceutically acceptable salts or solvates thereof.

The compounds of the invention may provide an attractive treatment option for, inter alia, diseases characterized, in whole or in part, by loss of body weight.

Cachexia is characterized by loss of body weight, loss of appetite, and wasting in an individual. Individuals affected by cachexia also experience fatigue, muscle atrophy, and weakness. Cachexia often is associated with diseases and conditions such as cancer, AIDS, physical trauma, chronic kidney disease and heart failure. Although cachexia represents a serious health problem, its underlying causes are not well-known. However, ghrelin is thought to play a role in the development of cachexia.

The compounds of the present invention may therefore be used as pharmaceutical agents for treating or preventing cachexia, promoting weight gain, reducing weight loss (e.g. by increasing appetite, food intake, and calorie intake), as well as associated diseases and health conditions. For example, the compounds of the invention may be used to treat low or loss of body weight, low or loss of body fat, low or loss of muscle mass, loss of appetite, decreased food intake, anorexia, bulimia, or the inability to gain weight or increase body mass in an individual that has been gastrectomized and/or vagectomized. The compounds of the invention may also be used for treatment of chronic obstructive pulmonary disease, growth hormone deficiency, osteoporosis, cardiovascular indications (e.g., low blood flow, low cardiac output, and high blood pressure), arthritis pain, inflammatory disorders (e.g., arthritis and systemic lupus erythematosus), and gastrointestinal disorders including but not limited to gastroparesis, post-operative ileus, inflammatory disorders such as colitis (e.g., ulcerative colitis), gut barrier dysfunction, inflammatory bowel disease (IBD), Crohn's disease, and ischemia reperfusion injury.

Thus, the invention provides use of a compound of the invention in the treatment of a condition as described above, in an individual in need thereof.

The invention also provides a compound of the invention for use in a method of medical treatment, particularly for use in a method of treatment of a condition as described above.

In preferred embodiments, the compounds described may be used in preventing weight loss or promoting weight gain.

In specific embodiments, the present invention comprises use of a compound of the invention for preventing weight loss or promoting weight gain in an individual in need thereof.

In specific embodiments, the present invention comprises use of a compound of the invention in a method of treatment of a condition caused or characterized by loss of body weight, e.g. the treatment and/or prevention of cachexia or wasting (for example in patients with burns, AIDS, kidney failure or sepsis), or treatment and/or prevention of the effects of gastrectomy, vagectomy, anorexia (e.g. anorexia nervosa) or bulimia, in an individual in need thereof.

In some embodiments, the present invention comprises use of a compound of the invention for treating chronic obstructive pulmonary disease.

In some embodiments, a compound of the invention may be used in promoting the production of growth hormone.

In specific embodiments, the present invention comprises use of a compound of the invention for promoting the production of growth hormone in an individual in need thereof.

In specific embodiments, the present invention comprises use of a compound of the invention in a method of treatment of a condition caused or characterized by low production of growth hormone.

In some embodiments, a compound of the invention may be used in promoting an increase in blood flow or cardiac output.

In specific embodiments, the present invention comprises use of a compound of the invention for promoting an increase in blood flow or cardiac output in an individual in need thereof.

In specific embodiments, the present invention comprises use of a compound of the invention in a method of treatment of a condition caused or characterized by low blood flow or cardiac output, e.g., low cardiac output syndrome or poor circulation.

In some embodiments, a compound of the invention may be used in treating post-operative ileus.

In some embodiments, a compound of the invention may be used in increasing gastrointestinal motility.

In specific embodiments, the present invention comprises use of a compound of the invention for increasing gastrointestinal motility in an individual in need thereof.

In specific embodiments, the present invention comprises use of a compound of the invention in a method of treatment of a condition caused or characterized by low gastrointestinal motility, e.g., gastroparesis.

In some embodiments, a compound of the invention may be used in reducing inflammation.

In specific embodiments, the present invention comprises use of a compound of the invention for reducing inflammation in an individual in need thereof.

In specific embodiments, the present invention comprises use of a compound of the invention in a method of treatment of a condition caused or characterized by inflammation, e.g., arthritis, systemic lupus erythematosus, colitis (e.g., ulcerative colitis), gut barrier dysfunction, inflammatory bowel disease (IBS), Crohn's disease, and ischemia reperfusion injury.

Exemplary effects of treatment using the compounds of the invention include preventing weight loss, promoting weight gain, treating obesity (e.g. by increasing appetite, food intake, and calorie intake), increasing production of growth hormone, increasing blood flow, increasing cardiac output, decreasing blood pressure, increasing gastrointestinal motility, and decreasing inflammation.

In some embodiments, the present invention comprises a pharmaceutical composition or method for suppressing or treating spinal nerve degeneration, damage, or cell death.

In some embodiments, the present invention comprises a pharmaceutical composition or method for promoting spinal nerve regeneration, proliferation or repair.

In some embodiments, the present invention comprises a pharmaceutical composition or method for suppressing or treating hyperglycemia.

In some embodiments, the present invention comprises a pharmaceutical composition or method for promoting insulin production in pancreatic beta cells.

In some embodiments, the present invention comprises a pharmaceutical composition or method for suppressing degeneration or disease of pancreatic beta cells.

In some embodiments, the present invention comprises a pharmaceutical composition or method for promoting health, longevity, neogenesis, or regeneration of pancreatic beta cells.

Pharmaceutical Compositions

The inclusion of one or more of a peptide compound of the invention in a pharmaceutical composition also encompasses inclusion of a pharmaceutically acceptable salt or solvate of a peptide compound of the invention.

The peptide compounds of the present invention may be formulated as pharmaceutical compositions which are suited for administration with or without storage, and which typically comprise a therapeutically effective amount of at least one peptide compound of the invention, together with a pharmaceutically acceptable carrier, excipient or vehicle.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, Pa., USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

A pharmaceutical composition of the invention may be in unit dosage form. In such form, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition. Compositions may be formulated for any suitable route and means of administration. Pharmaceutically acceptable carriers or diluents include those used in formulations suitable for e.g. oral, intraviteral, rectal, vaginal, nasal, topical, enteral or parenteral (including subcutaneous (SC), intramuscular (IM), intravenous (IV), intradermal and transdermal) administration or administration by inhalation. The formulations may conveniently be presented in unit dosage form and may be prepared by any of the methods well known in the art of pharmaceutical formulation.

Further embodiments of the invention relate to devices, dosage forms and packages used to deliver the pharmaceutical formulations of the present invention. Thus, at least one peptide compound or specified portion or variant in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Still further embodiments of the invention relate to oral formulations and administration. Formulations for oral administration may rely on the co-administration of adjuvants (e.g., resorcinols and nonionic surfactants such as polyoxyethylene oleyl ether and n-hexadecylpolyethylene ether) to artificially in-crease the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents, and perfuming agents.

Dosages

A typical dosage of a peptide compound of the invention as employed in the context of the present invention may be in the range from about 0.001-1,000 mg/subject per day, such as about 0.001 mg/subject, 0.01 mg/subject, 0.1 mg/subject, 1 mg/subject, 10 mg/subject, 100 mg/subject, and 1,000 mg/subject per day, administered in one or more doses, such as from one to three doses. As already indicated to some extent above, the exact dosage employed will depend, inter alia, on: the nature and severity of the disease or disorder to be treated; the sex, age, body weight and general condition of the subject to be treated; possible other, concomitant disease or disorder that is undergoing or is to undergo treatment; as well as other factors that will be known to a medical practitioner of skill in the art.

A peptide compound of the invention may be administered continuously (e.g., by intravenous administration or another continuous drug administration method), or may be administered to a subject in intervals, typically in regular time intervals, depending on the desired dosage and the pharmaceutical composition selected by the skilled practitioner for the particular subject. Regular administration dosing intervals include, e.g., once daily, twice daily, once every two, three, four, five or six days, once or twice weekly, once or twice monthly, and the like. Such regular peptide compound administration regimens of the invention may, in certain circumstances such as, e.g., during chronic long term administration, be advantageously interrupted for an interval of time so that the medicated subject reduces the level of or stops taking the medication, often referred to as taking a "drug holiday." Drug holidays are useful for, e.g., maintaining or regaining sensitivity to a drug especially during long term chronic treatment, or, to reduce unwanted side-effects of long term chronic treatment of the subject with the drug. The timing of a drug holiday depends on the timing of the regular dosing regimen and the purpose for taking the drug holiday (e.g., to regain drug sensitivity and/or to reduce unwanted side effects of continuous, long term administration). In some embodiments, the drug holiday may be a reduction in the drug (e.g., below the therapeutically effective amount for a certain interval of time). In other embodiments, administration of the drug is stopped for a certain interval of time before administration is started again, at the same or at a different dosing regimen (e.g., at a lower or higher dose and/or frequency of administration). A drug holiday of the invention may thus be selected from a wide range of times and dosage regimens. An exemplary drug holiday is two or more days, one or more weeks, one or more months, up to about 24 months of drug holiday. So, for example, a regular daily dosing regimen with a peptide compound of the invention may be interrupted by a drug holiday of a week, two weeks, or four weeks, after which time a daily or a weekly dosing schedule is resumed. A variety of other drug holiday regimens are envisioned to be useful for administering the peptide compounds of the invention.

Combination Therapy

As noted above, it will be understood that reference in the following to a peptide compound of the invention also extends to a pharmaceutically acceptable salt or solvate thereof as well as to a composition comprising more than one different peptide compound of the invention.

A peptide compound of the invention may be administered as part of a combination therapy together with another active agent for the treatment of the disease or disorder in question, e.g., cachexia, and in such cases, the two active agents may be given together or separately, e.g. as constituents in the same pharmaceutical composition or formulation, or as separate formulations.

A peptide compound of the invention may further be used in combination with an anti-hypertension agent of a known type, including, but not limited to, an angiotensin-converting enzyme inhibitor, an angiotensin II receptor blocker, a diuretic, a beta-blocker and a calcium channel blocker.

A peptide compound of the invention may still further be used in combination with an anti-dyslipidemia agent of known type, including, but not limited to, a statin, a fibrate, a niacin and/or a cholesterol absorption inhibitor.

A peptide compound of the invention may also be used in combination with a proton pump inhibitor (i.e., a pharmaceutical agent possessing pharmacological activity as an inhibitor H+/K+-ATPase) of known type, including, but not limited to, an agent of the benzimidazole derivative type or of the imidazopyridine derivative type, such as Omeprazole™, Lansoprazole™, Dexlansoprazole™, Esomeprazole™, Pantoprazole™, Rabeprazole™, Zolpidem™, Alpidem™, Saripidem™ or Necopidem™.

A peptide compound of the invention may also be used in combination with a pharmaceutical used to treat impaired gastrointestinal motility of known type, including, but not limited to, Leu13-motilin, prostaglandin F2 alpha, Cisapride®, Propulsid®, metoclopramide, domperidone, ondansetron, tropisetron, mosapride and itopride.

A peptide compound of the invention may also be used in combination with, for example, adenosine-antagonizing pyrazolopyridine compounds, pituitary adenylate cyclase activating peptide (PACAP) receptor antagonist, fedotozine; neuropeptides, and proteinase-activated receptor-2 antagonists (U.S. Pat. No. 5,929,035).

A peptide compound of the invention may, moreover, be used in combination with an anti-inflammatory agent of known type, including, but not limited to: steroids and corticosteroids, such as beclomethasone, methylprednisolone, betamethasone, prednisone, dexamethasone, and hydrocortisone; non-steroidal antiinflammatory agents (NSAIDs), such as propionic acid derivatives (e.g. alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives (e.g. indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac); fenamic acid derivatives (e.g. flufenamic acid, meclofenamic acid, mefenamic acid, niflumic acid and tolfenamic acid); biphenylcarboxylic acid derivatives (e.g. diflunisal and flufenisal); oxicams (e.g. isoxicam, piroxicam, sudoxicam and tenoxicam); salicylates (e.g. acetylsalicylic acid and sulfasalazine); and pyrazolones (e.g. apazone, bezpiperylon, feprazone, mofebutazone, oxyphenbutazone and phenylbutazone); COX II inhibitors, such as rofecoxib and celecoxib; preparations of interferon beta (e.g. interferon beta-1a or interferon beta-1b); and certain other compounds, such as 5-aminosalicylic acid and prodrugs and pharmaceutically acceptable salts thereof.

Each of the embodiments of the invention may be combined individually or in combination with one or more other embodiments of the invention.

Each of the compounds of the invention comprises, consists essentially of, or consists of a sequence as described herein.

EXAMPLES

Abbreviations employed in the following are as follows:
BSA: bovine serum albumin
COMU: 1-[(1-(cyano-2-ethoxy-2-oxoethylideneaminooxy)-dimethylamino-morpholinomethylene)]methanaminium hexafluorophosphate
DCM: dichloromethane
DMEM: Dulbecco's Modified Eagle's Medium
DMF: N,N-dimethylformamide
DMSO: dimethylsulfoxide
DIPEA: diisopropylethylamine
EtOH: ethanol
Et$_2$O: diethyl ether
Fmoc: 9-fluorenylmethoxycarbonyl
HATU: N-[(dimethylamino)-1H-1,2,3-triazol[4,5-b]pyridine-1-ylmethylene]-N-methylmethanaminium hexafluorophosphate N-oxide
HEPES: 4-(2-hydroxyethyl)-1-piperazineethane-sulfonic acid
HPLC: high-performance liquid chromatography
MeCN: acetonitrile
MS: mass spectroscopy
NEP: N-ethylpyrrolidone
NMP: N-methylpyrrolidone
PBS: phosphate-buffered saline
PCR: polymerase chain reaction
RP: reverse phase
TFA: trifluoroacetic acid
TIS: triisopropylsilane General Synthesis Procedure for Ghrelin Analogues Solid-phase peptide synthesis (SPPS) was performed on a microwave assisted synthesizer using standard Fmoc strategy in NMP or NEP on a polystyrene resin [such as TentaGel S PHB-Arg(Pbf)]. HATU or COMU was used as coupling reagent together with DIPEA as base. Piperidine (20% in NEP or DMF) was used for deprotection. Pseudoproline: Fmoc-Glu(OtBu)-Ser(Psi. Me, Me Pro)-OH (purchased from NovaBiochem) was used where applicable. Human ghrelin and rat ghrelin were likewise synthesized and purified using synthesis methodology and purification procedures as described herein.

Cleavage:

The crude peptide was cleaved from the resin by treatment with 95/2.5/2.5% (v/v) TFA/TIS/water at room temperature for 2 h. Most of the TFA was removed at reduced pressure, and the crude peptide was precipitated and washed with diethyl ether and allowed to dry at ambient temperature.

Peptide Purification

The crude peptides were purified by standard RP HPLC with a gradient of buffer A (0.1% aqueous TFA) and buffer B (aqueous solution containing 0.1% TFA and 90% MeCN). Fractions were analysed by analytical HPLC and MS, and relevant fractions were pooled and lyophilised.

The peptides were further purified by preparative RP HPLC using a gradient of buffer A' (0.1% aqueous TFA) and buffer B' (aqueous solution containing 0.1% TFA and 90% MeCN). The final product was characterised by analytical HPLC and MS.

Analytical HPLC Method

The peptides were analyzed by an analytical HPLC method using a gradient of buffer A' (see above) and buffer B' (see above).

Example 1

Synthesis of H-PS-S(O-octyl)-FLSPE-HQRVQQRKESKKPPAKLQPR-OH (Compound No. 19) (SEQ ID NO: 21)

TentaGel S PHB Fmoc-Arg(Pbf) resin (1.30 g; 0.326 mmol; Rapp Polymere) was treated with 20% piperidine in NEP for initial deprotection. A temperature increase to approx. 40° C. within 30 seconds was observed. The reaction vessel was drained and a second portion of 20% piperidine in NEP was added. This round of deprotection took place for 3 minutes, keeping the temperature between 70 and 75° C. The resin was then subjected to repeated introduction of Fmoc-amino acid by COMU/DIPEA, and elimination of Fmoc by 20% piperidine in NEP.

Coupling Step:

the mixture was heated to 75° C. and then allowed to cool down. This heating and cooling cycle was repeated over a period of 5 minutes. During the coupling, nitrogen was bubbled through the reaction vessel.

Fmoc Deprotection Step:

20% piperidine in NEP was added for initial deprotection. A temperature increase to approx. 40° C. within 30 seconds was observed. The reaction vessel was drained and a second portion of 20% piperidine in NEP was added. This round of deprotection took place for 3 minutes, keeping the temperature between 70 and 75° C.

In this sequential manner, the sidechain-protected peptide was assembled on the resin. The O-octyl-derivatised serine residue (at position 3) was introduced using the building block Fmoc-L-Ser(O-octyl)-OH (obtained from WuXi AppTec, China). Pseudoproline used: Fmoc-Glu(OtBu)-Ser (Psi. Me, Me Pro)-OH.

The dried peptide-containing resin (694 mg) was subjected to cleavage using 20 ml of the following mixture: TFA:TIS:water (95:2.5:2.5). After keeping the resin in contact with the cleavage mixture for 2 hours it was removed by filtration. The filtrate was concentrated in vacuo, and diethyl ether was added. The resulting precipitate was recovered by centrifugation and allowed to dry at room temperature, giving the crude peptide (450 mg).

The crude peptide was then dissolved in 10 ml buffer A and applied to a Gemini NX AXIA column (C18; 50 mm×250 mm; 110 Å, 10 micron). The column was eluted with a linear gradient of 95-85% buffer A for the first 3 minutes, and then with 85-60% buffer A for 47 minutes. Flow rate: 35 ml/min. The desired fractions were collected and lyophilized to give approx. 91 mg of the desired compound. Molecular mass determined by MS: 3394.93 Da (theoretical: 3394.93 Da).

Example 2

Synthesis of H-PS-S(O-octanoyl)-FLSPE-HQRVQQRKESKKPPAKLQPR-OH (Compound No. 5) (SEQ ID NO: 7)

TentaGel S PHB Fmoc-Arg(Pbf) resin (3.759 g, divided into three portions which were run in parallel; 0.940 mmol; Rapp Polymere) was treated with 20% piperidine in NEP for initial deprotection. A temperature increase to approx. 40° C. within 30 seconds was observed. The reaction vessel was drained and a second portion of 20% piperidine in NEP was added. This round of deprotection took place for 3 minutes, keeping the temperature between 70 and 75° C. The resin was then subjected to repeated introduction of Fmoc-amino acid by COMU/DIPEA, and elimination of Fmoc by 20% piperidine in NEP.

Coupling Step:

the mixture was heated to 75° C. and then allowed to cool down. This heating and cooling cycle was repeated over a period of 5 minutes. During the coupling, nitrogen was bubbled through the reaction vessel.

Fmoc Deprotection Step:

20% piperidine in NEP was added for initial deprotection. A temperature increase to approx. 40° C. within 30 seconds was observed. The reaction vessel was drained and a second portion of 20% piperidine in NEP was added. This round of deprotection took place for 3 minutes, keeping the temperature between 70 and 75° C. In this sequential manner, the 25 first residues of the sidechain-protected peptide were assembled on the resin. The synthesis was then continued using approx. one-sixth of the total amount of this peptide resin. The O-octanoyl-derivatised serine residue (at position 3) was introduced using the building block Fmoc-L-Ser(O-octanoyl)-OH (obtained from WuXi AppTec, China).

The dried peptide-containing resin (1419 mg) was subjected to cleavage using 40 ml of TFA:TIS:water (95:2.5:2.5). After keeping the resin in contact with the cleavage mixture for 2 hours it was removed by filtration. The filtrate was concentrated in vacuo, and diethyl ether was added. The resulting precipitate was recovered by centrifugation and allowed to dry at room temperature, giving the crude peptide (600 mg).

The crude peptide was then dissolved in 10 ml buffer A and applied to a Gemini NX AXIA column (C18; 50 mm×250 mm; 110 Å, 10 micron). The column was eluted with a linear gradient of 95-85% buffer A for the first 3 minutes, and then with 85-60% buffer A for 47 minutes. Flow rate: 35 ml/min. The desired fractions were collected and lyophilized to give approx. 61 mg of the desired compound. Molecular mass determined by MS: 3408.91 Da (theoretical: 3408.90 Da)

Example 3

Ghrelin Receptor Functional Assay

To test activation of the ghrelin receptor, stable cell lines expressing the human ghrelin receptor were produced. In brief, HEK293 cells were used for transfection of the cDNA for human ghrelin receptor cloned into the transfection plasmid pIRESneo2dNGFR. More specifically, the cDNA encoding the human growth hormone secretagogue receptor type 1a (GHSR1a; ghrelin receptor) was cloned from the cDNA clone AY429112 (accession no. AY429112.1; GI:38016896) (SEQ ID NO: 6). The DNA encoding the ghrelin receptor was amplified by PCR using primers also encoding terminal restriction sites for subcloning. The ghrelin receptor was subcloned into a mammalian expression vector containing a neomycin (G418) resistance marker. The fidelity of the DNA encoding the receptor was confirmed by DNA sequencing. HEK293 cells were used for transfection of the ghrelin receptor expression plasmid. The cells were grown according to standard protocol in growth medium and transfected with the plasmids using Lipofectamin (Invitrogen) according to the manufacturer's protocol. The cells stably expressing ghrelin receptor were selected using G418 in the growth medium (in that only cells that have taken up and incorporated the cDNA expression plasmid survive). The polyclonal cell line was propagated and stocks of cells were frozen for later use.

In vitro effects of compounds of the invention were examined by measuring $Ca^{2+}$ induction (using Fluo-4 Direct™ Calcium Assay Kit, Invitrogen F10471) in the HEK293 cell line stably expressing the human ghrelin receptor. The cells were seeded in Pre-coated Poly-L-lysine 96-well tissue culture plates with 20000 cells per well in 100 µl of standard growth medium (DMEM with Glutamax-I containing (Invitrogen 61965), 10% v/v FBS, Penicillin (100 IU/ml), Streptomycin (100 µg/ml), 1 mM sodium pyruvate, 1× non-essential amino acids (Invitrogen 11140) and 1% G418 (Gibco 10131-027). The cells were placed in an incubator (37° C., 5% $CO_2$) until the next day.

Fluo-4 Mix was prepared by mixing 10 ml of phenol-free DMEM with 10 ml 2× Fluo-4 Direct™ Calcium Reagent Loading Solution. Medium was removed from the cells and replaced with 100 µl of pre-warmed (37° C.) Fluo-4 Mix, and the cells were then placed in the incubator for 30 minutes. Peptides were dissolved to 1 mM in DMSO and diluted to 2× final concentration in modified peptide buffer (0.2% w/v BSA and 2 mM HEPES in PBS, pH 7.4.) in a 96-well plate. Positive control wells contained 200 nM human ghrelin (100 nM final) and negative control wells contained buffer with no peptide.

The plate with test compounds was pre-warmed before starting the measurements. The cell plate and compound plate were placed in a FLIPR instrument (Molecular Devices), and the program was initiated. The program measures basal level of fluorescence of Fluo-4 for 10 seconds, adds 100 µl of peptide solution to the cells and measures the change in fluorescence as a consequence of the changes in $Ca^{2+}$ concentration in the cells. The output used for calculation of activity was selected to be the maximal response (expressed as a ratio to the basal level. $EC_{50}$ values) and maximal response values were determined based on these values.

TABLE 1

$EC_{50}$ results for test compounds

| Compound No. | Sequence | EC50 (nM) |
|---|---|---|
| 1* | H-GS-S(O-octanoyl)-FLSPEHQRVQQRKESKKPPAKLQPR-OH (SEQ ID NO: 1) | 0.307 |
| 2* | H-GSSFLSPEHQRVQQRKESKKPPAKLQPR-OH (SEQ ID NO: 1) | >1,000 |
| 3* | H-GS-S(O-octanoyl)-FLSPEHQKAQQRKESKKPPAKLQPR-OH (SEQ ID NO: 195) | 0.204 |
| 4* | H-GSSFLSPEHQKAQQRKESKKPPAKLQPR-OH (SEQ ID NO: 195) | >1,000 |
| 5 | H-PS-S(O-octanoyl)-FLSPEHQRVQQRKESKKPPAKLQPR-OH (SEQ ID NO: 7) | 0.298 |
| 6 | H-[DPro]-S-S(O-octanoyl)-FLSPEHQRVQQRKESKKPPAKLQPR-OH (SEQ ID NO: 8) | 0.786 |
| 7 | H-FS-S(O-octanoyl)-FLSPEHQRVQQRKESKKPPAKLQPR-OH (SEQ ID NO: 9) | 0.714 |
| 8 | H-SS-S(O-octanoyl)-FLSPEHQRVQQRKESKKPPAKLQPR-OH (SEQ ID NO: 10) | 0.385 |
| 9 | H-Cmp-S(O-octanoyl)-FLSPEHQRVQQRKESKKPPAKLQPR-OH (SEQ ID NO: 11) | 0.558 |
| 10 | H-Mamb-S(O-octanoyl)-FLSPEHQRVQQRKESKKPPAKLQPR-OH (SEQ ID NO: 12) | 1.56 |
| 11 | H-[cACC]-S(O-octanoyl)-FLSPEHQRVQQRKESKKPPAKLQPR-OH (SEQ ID NO: 13) | 0.379 |
| 12 | H-[tACC]-S(O-octanoyl)-FLSPEHQRVQQRKESKKPPAKLQPR-OH (SEQ ID NO: 14) | 1.89 |
| 13 | H-Inp-S-S(O-octyl)-FLSPEHQRV-K(hexadecanoyl)-QRKESKKPPAKLQPR-OH (SEQ ID NO: 15) | 2.55 |
| 14 | H-Inp-S-S(O-octyl)-FLSPEHQRVQQRKES-K(hexadecanoyl)-KPPAKLQPR-OH (SEQ ID NO: 16) | 2.52 |
| 15 | H-Inp-S-S(O-octyl)-FLSPEHQRVQQRKESKKPPAKL-K(hexadecanoyl)-PR-OH (SEQ ID NO: 17) | 1.18 |
| 16 | H-PS-S(O-octyl)-FLSPEHQRVQQRKES-K(hexadecanoyl)-KPPAKLQPR-OH (SEQ ID NO: 18) | 2.88 |
| 17 | H-[DPro]-S-S(O-octyl)-FLSPEHQRVQQRKES-K(hexadecanoyl)-KPPAKLQPR-OH (SEQ ID NO: 19) | 4.63 |
| 18 | H-Aib-S-S(O-octyl)-FLSPEHQRVQQRKES-K(hexadecanoyl)-KPPAKLQPR-OH (SEQ ID NO: 20) | 2.9 |
| 19 | H-PS-S(O-octyl)-FLSPEHQRVQQRKESKKPPAKLQPR-OH (SEQ ID NO: 21) | 0.579 |
| 20 | H-[DPro]-S-S(O-octyl)-FLSPEHQRVQQRKESKKPPAKLQPR-OH (SEQ ID NO: 22) | 0.77 |
| 21 | H-Aib-S-S(O-octyl)-FLSPEHQRVQQRKESKKPPAKLQPR-OH (SEQ ID NO: 23) | 0.46 |

TABLE 1-continued

EC50 results for test compounds

| Compound No. | Sequence | EC50 (nM) |
|---|---|---|
| 22 | H-PS-Dap(N-octanoyl)-FLSPEHQRVQQRKESKKPPAKLQPR-NH$_2$ (SEQ ID NO: 74) | 0.193 |
| 23 | H-PS-Dap(N-octanoyl)-FLSPEHSRVSSRKESKKPPAKLSPR-NH$_2$ (SEQ ID NO: 82) | 0.224 |
| 24 | H-PS-Dap(N-octanoyl)-FLSPEHQRVQQRKESKKPPA-NH$_2$ (SEQ ID NO: 139) | 0.136 |
| 25 | H-PS-Dap(N-octanoyl)-FLSP-NH$_2$ (SEQ ID NO: 155) | 0.26 |
| 26 | H-PS-Dap(N-octanoyl)-FLS-NH$_2$ (SEQ ID NO: 156) | 1.2 |
| 27 | H-PS-Dap(N-octanoyl)-FL-NH$_2$ (SEQ ID NO: 157) | 1.69 |
| 28 | H-PS-[NH-CH(n-C$_{10}$H$_{21}$)-C(O)]-FLSPEHQRVQQRKES-NH$_2$ (SEQ ID NO: 181) | 0.164 |
| 29 | H-PS-[NH-CH(n-C$_{10}$H$_{21}$)-C(O)]-FLSPEHQRVQQRKESKKPPA-NH$_2$ (SEQ ID NO: 176) | 0.255 |
| 30 | H-GS-S(octanoyl)-FLSPEOHQRKOQQRKESKKPPAKLQPR-OH (SEQ ID NO: 94) | 0.534 |
| 31 | H-GS-S(octanoyl)-FLSPEHEURVQKORKESKKPPAKLQPR-OH (SEQ ID NO: 95) | 0.597 |
| 32 | H-GS-S(octanoyl)-FLSPEHQRVQQRKOESKEOPPAKLQPR-OH (SEQ ID NO: 96) | 1.29 |
| 33 | H-PS-S(O-octyl)-FLSPEOHQRKOQQRKESKKPPAKLQPR-NH$_2$ (SEQ ID NO: 97) | 0.365 |
| 34 | H-PS-S(O-octyl)-FLSPEHEURVQKORKESKKPPAKLQPR-NH$_2$ (SEQ ID NO: 98) | 0.155 |
| 35 | H-Orn-S(O-octyl)-FLSPEHQRVQQRKESKKPPAKLQPR-NH$_2$ (SEQ ID NO: 99) | 0.527 |
| 36 | Ac-Orn-S(O-octyl)-FLSPEHQRVQQRKESKKPPAKLQPR-NH$_2$ (SEQ ID NO: 99) | 1.4 |
| 37 | H-PS-Dap(N-octanoyl)-FLSPEHQRVQRKESKKPPAKLQPR-NH$_2$ (SEQ ID NO: 100) | 0.253 |
| 38 | H-PS-S(O-octyl)-FLSPEHQRVQRKESKKPPAKLQPR-NH$_2$ (SEQ ID NO: 101) | 0.33 |
| 39 | H-PS-Dap(N-octanoyl)-FLSPK-NH$_2$ (SEQ ID NO: 102) | 0.364 |
| 40 | H-PS-S(O-octyl)-FLSPK-NH$_2$ (SEQ ID NO: 103) | 0.388 |
| 41 | H-PS-[NH-CH(n-C$_{10}$H$_{21}$)-C(O)]-R-SPK-NH$_2$ (SEQ ID NO: 104) | 0.432 |
| 42 | H-PS-Dap(N-octanoyl)-FLSPY-NH$_2$ (SEQ ID NO: 105) | 0.195 |
| 43 | H-PS-S(O-octyl)-FLSPEHQRVQQRKES-K(hexadecanoyl-isoGlu)-KPPAKLQPR-NH$_2$ (SEQ ID NO: 106) | 0.496 |
| 44 | H-PS-Dap(N-octanoyl)-FLSPEHSRVSSRKES-K(hexadecanoyl-isoGlu)-KPPA-NH$_2$ (SEQ ID NO: 107) | 0.566 |
| 45 | H-PS-S(O-octyl)-FLSPEHSRVSSRKESSKPPAKLSPR-NH$_2$ (SEQ ID NO: 108) | 0.359 |
| 46 | H-PS-S(O-octyl)-FLSPEHSRVSSRKESKSPPAKLSPR-NH$_2$ (SEQ ID NO: 109) | 0.296 |
| 47 | H-PS-S(O-octyl)-FLSPEHSRVSSRKESSSPPAKLSPR-NH$_2$ (SEQ ID NO: 110) | 0.454 |
| 48 | H-PS-S(O-octyl)-FLSPEHSRPSSR-NH$_2$ (SEQ ID NO: 111) | 0.341 |
| 49 | H-PS-S(O-octyl)-FLSPEHSRVSSRPESSSPPAKLSPR-NH$_2$ (SEQ ID NO: 112) | 0.525 |

TABLE 1-continued

EC$_{50}$ results for test compounds

| Compound No. | Sequence | EC50 (nM) |
|---|---|---|
| 50 | H-PS-S(O-octyl)-FLSPEHSRPSSRPESSSPPAKLSPR-NH$_2$ (SEQ ID NO: 113) | 0.642 |
| 51 | H-PS-S(octanoyl)-FLSPEHQSVQQRKESKKPPAKLQPR-NH$_2$ (SEQ ID NO: 114) | 0.149 |
| 52 | H-PS-S(octanoyl)-FLSPEHQRVQQSKESKKPPAKLQPR-NH$_2$ (SEQ ID NO: 115) | 0.168 |
| 53 | H-PS-S(octanoyl)-FLSPEHQRVQQRSESKKPPAKLQPR-NH$_2$ (SEQ ID NO: 116) | 0.182 |
| 54 | H-PS-S(octanoyl)-FLSPEHQRVQQRKESSKPPAKLQPR-NH$_2$ (SEQ ID NO: 117) | 0.095 |
| 55 | H-PS-S(octanoyl)-FLSPEHQRVQQRKESKSPPAKLQPR-NH$_2$ (SEQ ID NO: 118) | 0.086 |
| 56 | H-PS-S(octanoyl)-FLSPEHQRVQQRKESKKPPASLQPR-NH$_2$ (SEQ ID NO: 119) | 0.183 |
| 57 | H-PS-S(octanoyl)-FLSPEHQRVQQRKESKKPPAKLQPS-NH$_2$ (SEQ ID NO: 120) | 0.039 |
| 58 | H-PS-S(octanoyl)-FLSPYHQRVQQRKESKKPPAKLQPR-NH$_2$ (SEQ ID NO: 121) | 0.719 |
| 59 | H-PS-S(octanoyl)-FLSPEHQRVQYRKESKKPPAKLQPR-NH$_2$ (SEQ ID NO: 122) | 0.198 |
| 60 | H-PS-S(octanoyl)-FLSPEHQRVQQRKESKKPPAYLQPR-NH$_2$ (SEQ ID NO: 123) | 0.252 |
| 61 | H-PS-S(octanoyl)-FLSPYHQRVQYRKESKKPPAYLQPR-NH$_2$ (SEQ ID NO: 124) | 0.594 |
| 62 | H-PS-S(O-octyl)-FLSPEHQRVQQRKESKKPPAKLQPR-NH$_2$ (SEQ ID NO: 125) | 0.396 |
| 63 | H-PS-S(O-octyl)-FLSPEHQRVQRKESKKPPAKLQPR-NH$_2$ (SEQ ID NO: 126) | 0.33 |
| 64 | H-PS-S(O-octyl)-FLSPEHQRVQQRKESKKPPA-NH$_2$ (SEQ ID NO: 127) | 0.231 |
| 65 | H-PS-S(O-octyl)-FLSPEHQRVQQRKES-NH$_2$ (SEQ ID NO: 128) | 0.221 |
| 66 | H-PS-[NH-CH(n-C$_{10}$H$_{21}$)-C(O)]-FLSPEHQRVQQRKESKKPPAKLQPR-NH$_2$ (SEQ ID NO: 129) | 0.333 |
| 67 | H-PS-[NH-CH(n-$_{C10}$H$_{21}$)-C(O)]-FLSPEHQRVQRKESKKPPAKLQPR-NH$_2$ (SEQ ID NO: 130) | 0.23 |
| 68 | H[cACC]-S(O-octyl)-FLSPEHQRVQQRKESKKPPAKLQPR-NH$_2$ (SEQ ID NO: 131) | 0.271 |
| 69 | H-PS-S(O-octyl)-FLSPEHSR-NH$_2$ (SEQ ID NO: 132) | 0.44 |
| 70 | H-PS-S(O-octyl)-FLSPEHSRVSSR-NH$_2$ (SEQ ID NO: 133) | 0.467 |
| 71 | H-PS-S(O-octyl)-FLSPEHSRVSSRKESKKPPAKLSPR-NH$_2$ (SEQ ID NO: 134) | 0.48 |

*Compound No. 1: human ghrelin with an octanoyl moiety at position 3
*Compound No. 2: human ghrelin without octanoyl moiety at position 3
*Compound No. 3: rat ghrelin with octanoyl moiety at position 3
*Compound No. 4: rat ghrelin without octanoyl moiety at position 3

Example 4

Effect of Compounds of the Invention on Food Intake in Normal Mice

Normal chow-fed C57BL/6J male mice were used. The mice were kept in an automated food- and water-intake monitoring system (HM-2) which allows automated on-line measurements of accumulated food intake (FI) and other parameters. Food intake was monitored by the HM-2 system up to 24 h after dosing. The mice were kept 6 per cage, and each dosing group consisted of 6 animals. The animals were dosed once subcutaneously with vehicle (PBS) or with test compound [human ghrelin (Compound 1 in Table 1) or Compound 16, 22, 23 or 43 of the invention] at a dose of 300 nmol/kg body weight, just after the start of the light period in which the mice are inactive and normally do not eat.

In the initial experimental set-up with ghrelin as test compound, animals were allowed free access to food directly after treatment, and the resulting data for food intake are shown in FIG. 1A herein (vide infra).

In order to further investigate the "duration of action" of ghrelin and the other test compounds a new protocol was defined. In the modified protocol the gate to the food chambers was closed prior to dosing with vehicle or test compound and was re-opened 2 hours thereafter. The resulting data for food intake following dosing with ghrelin or vehicle are summarized in FIG. 1B (vide infra), while the corresponding data for food intake following dosing with each of the of the other four test compounds. (Compound 16, 22, 23 or 43 of the invention) or with vehicle are summarized in FIG. 2A (data for monitoring up to 6 hours after dosing) and FIG. 2B (data for monitoring up to 24 hours after dosing).

Results:

When animals had free access to food immediately after dosing, the administration of ghrelin resulted in increased FI when compared to PBS treated controls (FIG. 1A). In contrast, when access to food was delayed for 2 h after ghrelin administration, the effect of ghrelin was essentially lost (FIG. 1B).

Figure 2:
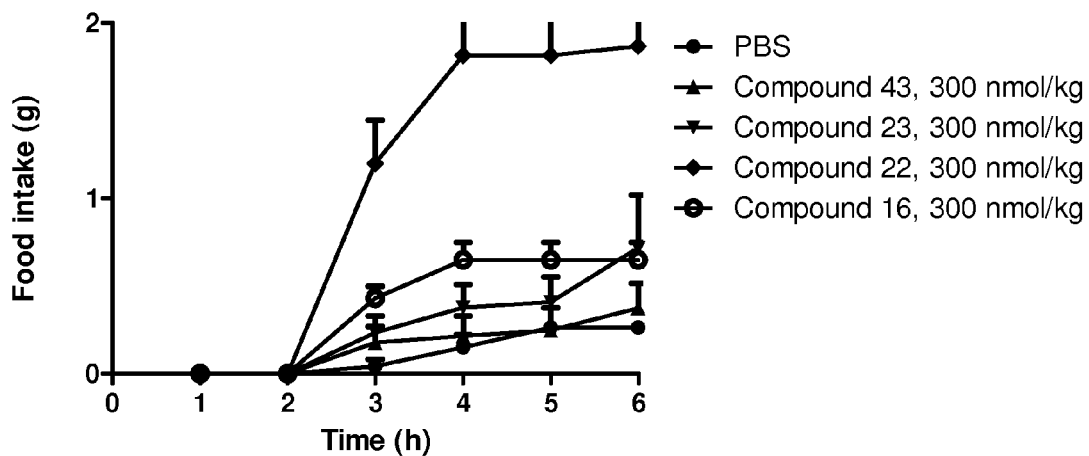
FIG. 2: Effects of administration of test compounds of the invention or vehicle early in the light phase on food intake in normal mice. Animals had access to food 2 hours after compound administration. (A) 0-6 hour accumulated food intake (B) 0-24 hour accumulated food intake.
Figure 2:
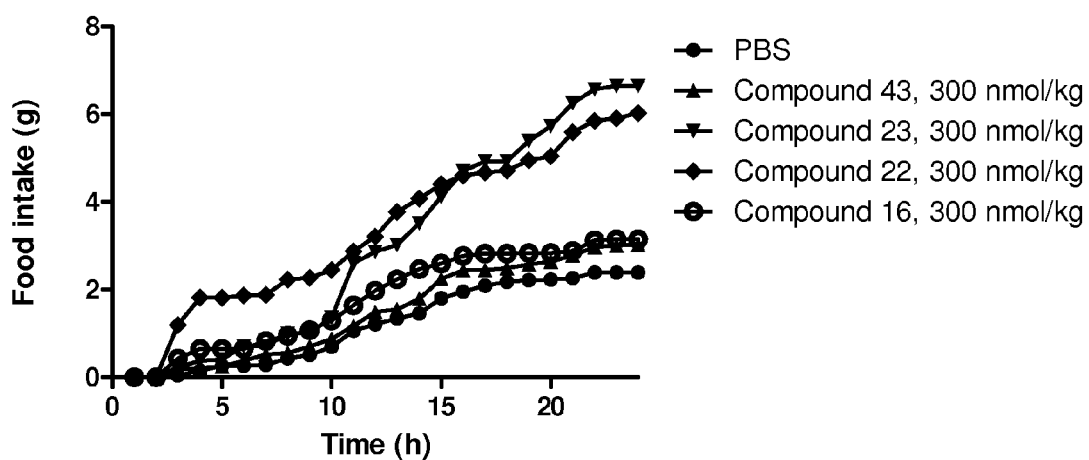

Since ghrelin had little effect on FI in the light phase of the modified protocol, this protocol was used for screening compounds (ghrelin analogues) of the invention having a longer duration of action than ghrelin per se. Examples of FI responses (0-6 h) and (0-24 h) for four compounds of the invention are presented in FIG. 2, while data for accumulated food intake (FI) for a total of 11 compounds of the invention (determined using the modified protocol) are presented in Table 2 (below). Interestingly, Compound 23 of the invention produced moderate effects in the 0-6 h light period (FIG. 2A), but had significant effects on FI during the dark period (FIG. 2B), while Compound 22 had significant effects on FI in both the light period and the dark period. Treatment with vehicle (PBS) had little effect on FI during the light period (FIG. 2A), and animals ate normally during the dark period (FIG. 2B).

TABLE 2

Effect of administration of test compounds (compounds of the invention) or vehicle (PBS) on FI in the light phase (0-6 h) using the modified protocol (vide supra). Data are expressed as accumulated FI (g) over 6 h.

| Compound | Accumulated FI at 6h (g) |
|---|---|
| PBS | 0.26 ± 0.04 |
| 16 | 0.65 ± 0.1 |
| 22 | 1.87 ± 0.23 |
| 43 | 0.37 ± 0.14 |
| 23 | 0.72 ± 0.3 |
| PBS | 0.03 ± 0.002 |
| 29 | 1.36 ± 0.2 |
| 34 | 0.53 ± 0.08 |
| 23 | 0.32 ± 0.23 |
| PBS | 0.08 ± 0.04 |
| 42 | 0.2 ± 0.08 |
| PBS | 0.6 ± 0.19 |
| 45 | 0.38 ± 0.13 |
| 46 | 1.68 ± 0.2 |
| 47 | 1.55 ± 0.16 |
| PBS | 0.12 ± 0.05 |
| 48 | 0 ± 0 |
| 49 | 0.6 ± 0.09 |
| 50 | 0.19 ± 0.05 |

SEQUENCE LISTING

```
<160> NUMBER OF SEQ ID NOS: 195

<210> SEQ ID NO 1
<211> LENGTH: 28
<212> TYPE: PRT
<213> ORGANISM: Homo sapiens
<220> FEATURE:
<221> NAME/KEY: SITE
<222> LOCATION: (3)..(3)
<223> OTHER INFORMATION: Ser(O-octanoyl), a modified (acylated) serine
      residue in which the hydrogen of the side-chain hydroxy group in
      serine is replaced by an n-octanoyl group

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 2
<211> LENGTH: 28
<212> TYPE: PRT
<213> ORGANISM: Artificial sequence
<220> FEATURE:
<223> OTHER INFORMATION: Synthetic sequence: Peptide sequence Z of
      Formula I of PCT/EP2013/052107;  Formula Ia
<220> FEATURE:
<221> NAME/KEY: VARIANT
<222> LOCATION: (1)..(2)
<223> OTHER INFORMATION: In specific compounds, Xaa1 is an amino acid
      residue selected from Ala, Inp, Pro, DPro, Sar, Aib, Phe & Ser,
      and  Xaa2 is Ser
<220> FEATURE:
<221> NAME/KEY: VARIANT
<222> LOCATION: (1)..(2)
<223> OTHER INFORMATION: In specific compounds, Xaa1 & Xaa2 together
      constitute a residue of a non-naturally occurring amino acid as
      defined in Claim 1 of PCT/EP2013/052107
<220> FEATURE:
<221> NAME/KEY: VARIANT
<222> LOCATION: (3)..(3)
<223> OTHER INFORMATION: When Xaa1 is P, DPro, F or S, Xaa3 is
      -NH-CH((CH2)n-O-R3)-C(O)-, -NH-CH(R4)-C(O)-, - NH-CH((CH2)m-O-R5)-
      C-(O)-, or-NH-CH((CH2)p-NH-R6)-C(O)-. (R3-R6, & integers n, m, p,
      are as defined in Claim 1 of PCT/EP2013/052107)
<220> FEATURE:
<221> NAME/KEY: VARIANT
<222> LOCATION: (3)..(3)
<223> OTHER INFORMATION: When X1 & X2 together constitute a non-
      naturally occurring amino acid, X3 is -NH-CH((CH2)n-O-R3)-C(O)-,
      -NH-CH(R4)-C(O)-, -NH-CH((CH2)m-O-R5)-C-(O)-, or-NH-CH((CH2)p-NH-
      R6)-C(O)-. (R3-R6, & integers n, m, p, are defined in Claim 1 of
      PCT/EP2013052107)
<220> FEATURE:
<221> NAME/KEY: VARIANT
<222> LOCATION: (3)..(3)
<223> OTHER INFORMATION: When Xaa1 is selected from A, Sar, Inp, & Aib,
      Xaa3 is selected among (i) -NH-CH((CH2)n-O-R3)-C(O)-; and (ii)
      -NH-CH(R4)-C(O)-. (R3 & R4 are as defined in Claim 1 of
      PCT/EP2013052107, and n is an integer 1, 2, 3, 4 or 5).
<220> FEATURE:
<221> NAME/KEY: VARIANT
<222> LOCATION: (6)..(28)
<223> OTHER INFORMATION: Truncated forms lack from 1 to 23 amino acids
      from the C-terminus
<220> FEATURE:
<221> NAME/KEY: VARIANT
<222> LOCATION: (8)..(8)
<223> OTHER INFORMATION: When present, Xaa is selected from Glu, Lys and
      Tyr
<220> FEATURE:
<221> NAME/KEY: VARIANT
<222> LOCATION: (10)..(10)
<223> OTHER INFORMATION: When present, Xaa is selected from Gln, Glu and
      Ser
<220> FEATURE:
<221> NAME/KEY: VARIANT
<222> LOCATION: (11)..(11)
<223> OTHER INFORMATION: When present, Xaa is selected from Arg, Lys and
      Ser
<220> FEATURE:
<221> NAME/KEY: VARIANT
<222> LOCATION: (12)..(12)
<223> OTHER INFORMATION: When present, Xaa is selected from Val, Ala,
      Pro, Lys, Thr and Leu
<220> FEATURE:
<221> NAME/KEY: VARIANT
<222> LOCATION: (13)..(13)
<223> OTHER INFORMATION: When present, Xaa is selected from Gln & Ser
<220> FEATURE:
<221> NAME/KEY: VARIANT
<222> LOCATION: (14)..(14)
<223> OTHER INFORMATION: May be present or absent. When present, Xaa is
      selected from Gln, Lys, Tyr & Ser
<220> FEATURE:
<221> NAME/KEY: VARIANT
<222> LOCATION: (15)..(15)
```

```
<223> OTHER INFORMATION: When present, Xaa is selected from Arg & Ser
<220> FEATURE:
<221> NAME/KEY: VARIANT
<222> LOCATION: (16)..(16)
<223> OTHER INFORMATION: When present, Xaa is selected from Lys, Ser and
      Pro
<220> FEATURE:
<221> NAME/KEY: VARIANT
<222> LOCATION: (19)..(19)
<223> OTHER INFORMATION: When present, Xaa is selected from Lys and Ser
<220> FEATURE:
<221> NAME/KEY: VARIANT
<222> LOCATION: (20)..(20)
<223> OTHER INFORMATION: When present, Xaa is selected from Lys, Glu and
      Ser
<220> FEATURE:
<221> NAME/KEY: VARIANT
<222> LOCATION: (24)..(24)
<223> OTHER INFORMATION: When present, Xaa is selected from Lys, Tyr and
      Ser
<220> FEATURE:
<221> NAME/KEY: VARIANT
<222> LOCATION: (26)..(26)
<223> OTHER INFORMATION: When present, Xaa is selected from Gln and Ser
<220> FEATURE:
<221> NAME/KEY: VARIANT
<222> LOCATION: (28)..(28)
<223> OTHER INFORMATION: When present, Xaa is selected from Arg and Ser

<400> SEQUENCE: 2

Xaa Xaa Xaa Phe Leu Ser Pro Xaa His Xaa Xaa Xaa Xaa Xaa Xaa
1               5                   10                  15

Glu Ser Xaa Xaa Pro Pro Ala Xaa Leu Xaa Pro Xaa
            20                  25

<210> SEQ ID NO 3
<211> LENGTH: 28
<212> TYPE: PRT
<213> ORGANISM: Artificial sequence
<220> FEATURE:
<223> OTHER INFORMATION: Synthetic sequence: Peptide sequence Z of
      Formula I of PCT/EP2013/052107;  Formula Ib
<220> FEATURE:
<221> NAME/KEY: VARIANT
<222> LOCATION: (1)..(2)
<223> OTHER INFORMATION: In specific compounds, Xaa1 is an amino acid
      residue selected from Ala, Inp, Pro, DPro, Sar, Aib, Phe & Ser,
      and  Xaa2 is Ser
<220> FEATURE:
<221> NAME/KEY: VARIANT
<222> LOCATION: (1)..(2)
<223> OTHER INFORMATION: In specific compounds, Xaa1 & Xaa2 together
      constitute a residue of a non-naturally occurring amino acid as
      defined in Claim 1 of PCT/EP2013/052107
<220> FEATURE:
<221> NAME/KEY: VARIANT
<222> LOCATION: (3)..(3)
<223> OTHER INFORMATION: When Xaa1 is P, DPro, F or S, Xaa3 is
      -NH-CH((CH2)n-O-R3)-C(O)-, -NH-CH(R4)-C(O)-, - NH-CH((CH2)m-O-R5)-
      C-(O)-, or-NH-CH((CH2)p-NH-R6)-C(O)-. (R3-R6, & integers n, m, p,
      are as defined in Claim 1 of PCT/EP2013/052107)
<220> FEATURE:
<221> NAME/KEY: VARIANT
<222> LOCATION: (3)..(3)
<223> OTHER INFORMATION: When X1 & X2 together constitute a non-
      naturally occurring amino acid, X3 is -NH-CH((CH2)n-O-R3)-C(O)-,
      -NH-CH(R4)-C(O)-, -NH-CH((CH2)m-O-R5)-C-(O)-, or-NH-CH((CH2)p-NH-
      R6)-C(O)-. (R3-R6, & integers n, m, p, are defined in Claim 1 of
      PCT/EP2013052107)
<220> FEATURE:
<221> NAME/KEY: VARIANT
<222> LOCATION: (3)..(3)
<223> OTHER INFORMATION: When Xaa1 is selected from A, Sar, Inp, & Aib,
      Xaa3 is selected among (i) -NH-CH((CH2)n-O-R3)-C(O)-; and (ii)
      -NH-CH(R4)-C(O)-. (R3 & R4 are as defined in Claim 1 of
      PCT/EP2013052107, and n is an integer 1, 2, 3, 4 or 5).
```

-continued

```
<220> FEATURE:
<221> NAME/KEY: VARIANT
<222> LOCATION: (6)..(28)
<223> OTHER INFORMATION: Truncated forms lack from 1 to 23 amino acids
      from the C-terminus
<220> FEATURE:
<221> NAME/KEY: VARIANT
<222> LOCATION: (10)..(10)
<223> OTHER INFORMATION: In Claim 2 of PCT/EP2013/052107, Xaa, when
      present, is selected from Gln and Ser
<220> FEATURE:
<221> NAME/KEY: VARIANT
<222> LOCATION: (10)..(10)
<223> OTHER INFORMATION: In Claim 3 of PCT/EP2013/052107, Xaa, when
      present, is Gln
<220> FEATURE:
<221> NAME/KEY: VARIANT
<222> LOCATION: (11)..(11)
<223> OTHER INFORMATION: When present, Xaa is selected from Arg and Lys
<220> FEATURE:
<221> NAME/KEY: VARIANT
<222> LOCATION: (12)..(12)
<223> OTHER INFORMATION: When present, Xaa is selected from Val, Ala,
      Thr and Leu
<220> FEATURE:
<221> NAME/KEY: VARIANT
<222> LOCATION: (13)..(13)
<223> OTHER INFORMATION: In Claim 2 of PCT/EP2013/052107, Xaa, when
      present, is selected from Gln & Ser
<220> FEATURE:
<221> NAME/KEY: VARIANT
<222> LOCATION: (13)..(13)
<223> OTHER INFORMATION: In Claim 3 of PCT/EP2013/052107, Xaa, when
      present, is Gln
<220> FEATURE:
<221> NAME/KEY: VARIANT
<222> LOCATION: (14)..(14)
<223> OTHER INFORMATION: May be present or absent. In Claim 2 of PCT/
      EP2013/052107, Xaa, when present, is selected from Gln & Ser
<220> FEATURE:
<221> NAME/KEY: VARIANT
<222> LOCATION: (14)..(14)
<223> OTHER INFORMATION: May be present or absent. In Claim 3 of PCT/
      EP2013/052107, Xaa, when present, is Gln
<220> FEATURE:
<221> NAME/KEY: VARIANT
<222> LOCATION: (16)..(16)
<223> OTHER INFORMATION: When present, Xaa is Lys
<220> FEATURE:
<221> NAME/KEY: VARIANT
<222> LOCATION: (19)..(19)
<223> OTHER INFORMATION: When present, Xaa is Lys
<220> FEATURE:
<221> NAME/KEY: VARIANT
<222> LOCATION: (20)..(20)
<223> OTHER INFORMATION: When present, Xaa is Lys
<220> FEATURE:
<221> NAME/KEY: VARIANT
<222> LOCATION: (24)..(24)
<223> OTHER INFORMATION: When present, Xaa is Lys
<220> FEATURE:
<221> NAME/KEY: VARIANT
<222> LOCATION: (26)..(26)
<223> OTHER INFORMATION: In Claim 2 of PCT/EP2013/052107, Xaa, when
      present, is selected from Gln and Ser
<220> FEATURE:
<221> NAME/KEY: VARIANT
<222> LOCATION: (26)..(26)
<223> OTHER INFORMATION: In Claim 3 of PCT/EP2013/052107, Xaa, when
      present, is Gln
<220> FEATURE:
<221> NAME/KEY: VARIANT
<222> LOCATION: (28)..(28)
<223> OTHER INFORMATION: When present, Xaa is Arg

<400> SEQUENCE: 3

Xaa Xaa Xaa Phe Leu Ser Pro Glu His Xaa Xaa Xaa Xaa Xaa Arg Xaa
1               5                   10                  15
```

```
Glu Ser Xaa Xaa Pro Pro Ala Xaa Leu Xaa Pro Xaa
            20                  25

<210> SEQ ID NO 4
<211> LENGTH: 28
<212> TYPE: PRT
<213> ORGANISM: Artificial sequence
<220> FEATURE:
<223> OTHER INFORMATION: Synthetic sequence: Peptide sequence Z of
      Formula I of PCT/EP2013/052107;  Formula Ic
<220> FEATURE:
<221> NAME/KEY: VARIANT
<222> LOCATION: (3)..(3)
<223> OTHER INFORMATION: Xaa3 is selected from among (i) -NH-CH((CH2)n-
      O-R3)-C(O)-; and (ii) -NH-CH((CH2)p-NH-R6)-C(O)-. (R3 & R6 are as
      defined in Claim 1 of PCT/EP2013/052107, and n and p are integers
      1, 2, 3, 4 or 5)
<220> FEATURE:
<221> NAME/KEY: VARIANT
<222> LOCATION: (6)..(28)
<223> OTHER INFORMATION: Truncated forms lack from 1 to 23 amino acids
      from the C-terminus
<220> FEATURE:
<221> NAME/KEY: VARIANT
<222> LOCATION: (10)..(10)
<223> OTHER INFORMATION: When present, Xaa is selected from Gln, Glu and
      Ser
<220> FEATURE:
<221> NAME/KEY: VARIANT
<222> LOCATION: (11)..(11)
<223> OTHER INFORMATION: When present, Xaa is selected from Arg and Lys
<220> FEATURE:
<221> NAME/KEY: VARIANT
<222> LOCATION: (12)..(12)
<223> OTHER INFORMATION: When present, Xaa is selected from Val, Ala,
      Thr and Leu
<220> FEATURE:
<221> NAME/KEY: VARIANT
<222> LOCATION: (13)..(13)
<223> OTHER INFORMATION: When present, Xaa is selected from Gln & Ser
<220> FEATURE:
<221> NAME/KEY: VARIANT
<222> LOCATION: (14)..(14)
<223> OTHER INFORMATION: May be present or absent. When present, Xaa is
      selected from Gln & Ser
<220> FEATURE:
<221> NAME/KEY: VARIANT
<222> LOCATION: (16)..(16)
<223> OTHER INFORMATION: When present, Xaa is Lys
<220> FEATURE:
<221> NAME/KEY: VARIANT
<222> LOCATION: (19)..(19)
<223> OTHER INFORMATION: When present, Xaa is Lys
<220> FEATURE:
<221> NAME/KEY: VARIANT
<222> LOCATION: (20)..(20)
<223> OTHER INFORMATION: When present, Xaa is Lys
<220> FEATURE:
<221> NAME/KEY: VARIANT
<222> LOCATION: (24)..(24)
<223> OTHER INFORMATION: When present, Xaa is Lys
<220> FEATURE:
<221> NAME/KEY: VARIANT
<222> LOCATION: (26)..(26)
<223> OTHER INFORMATION: When present, Xaa is selected from Gln and Ser
<220> FEATURE:
<221> NAME/KEY: VARIANT
<222> LOCATION: (28)..(28)
<223> OTHER INFORMATION: When present, Xaa is Arg

<400> SEQUENCE: 4

Pro Ser Xaa Phe Leu Ser Pro Glu His Xaa Xaa Xaa Xaa Xaa Arg Xaa
1               5                   10                  15

Glu Ser Xaa Xaa Pro Pro Ala Xaa Leu Xaa Pro Xaa
            20                  25
```

```
<210> SEQ ID NO 5
<211> LENGTH: 28
<212> TYPE: PRT
<213> ORGANISM: Artificial sequence
<220> FEATURE:
<223> OTHER INFORMATION: Synthetic sequence: Peptide sequence Z of
      Formula I of PCT/EP2013/052107;  Formula Id
<220> FEATURE:
<221> NAME/KEY: VARIANT
<222> LOCATION: (3)..(3)
<223> OTHER INFORMATION: In Claim 10 of PCT/EP2013/052107, Xaa3 is
      -NH-CH((CH2)n-O-R3)-C(O)-, wherein R3 is a C1-35-alkyl or -
      alkenyl group and n is an integer 1, 2, 3, 4 or 5
<220> FEATURE:
<221> NAME/KEY: VARIANT
<222> LOCATION: (3)..(3)
<223> OTHER INFORMATION: In Claim 11 of PCT/EP2013/052107, Xaa3 is
      -NH-CH((CH2)p-NH-R6)-C(O)-, wherein R6 is a C1-35-acyl group and
      p is an integer 1, 2, 3, 4 or 5
<220> FEATURE:
<221> NAME/KEY: VARIANT
<222> LOCATION: (6)..(28)
<223> OTHER INFORMATION: Truncated forms lack from 1 to 23 amino acids
      from the C-terminus
<220> FEATURE:
<221> NAME/KEY: VARIANT
<222> LOCATION: (10)..(10)
<223> OTHER INFORMATION: In Claim 10 of PCT/EP2013/052107, when present,
      Xaa is selected from Gln and Ser
<220> FEATURE:
<221> NAME/KEY: VARIANT
<222> LOCATION: (10)..(10)
<223> OTHER INFORMATION: In Claim 11 of PCT/EP2013/052107, when present,
      Xaa is selected from Gln, Glu and Ser
<220> FEATURE:
<221> NAME/KEY: VARIANT
<222> LOCATION: (11)..(11)
<223> OTHER INFORMATION: When present, Xaa is selected from Arg and Lys
<220> FEATURE:
<221> NAME/KEY: VARIANT
<222> LOCATION: (13)..(13)
<223> OTHER INFORMATION: When present, Xaa is selected from Gln & Ser
<220> FEATURE:
<221> NAME/KEY: VARIANT
<222> LOCATION: (14)..(14)
<223> OTHER INFORMATION: May be present or absent. When present, Xaa is
      selected from Gln & Ser
<220> FEATURE:
<221> NAME/KEY: VARIANT
<222> LOCATION: (16)..(16)
<223> OTHER INFORMATION: When present, Xaa is Lys
<220> FEATURE:
<221> NAME/KEY: VARIANT
<222> LOCATION: (19)..(19)
<223> OTHER INFORMATION: When present, Xaa is Lys
<220> FEATURE:
<221> NAME/KEY: VARIANT
<222> LOCATION: (24)..(24)
<223> OTHER INFORMATION: When present, Xaa is Lys
<220> FEATURE:
<221> NAME/KEY: VARIANT
<222> LOCATION: (26)..(26)
<223> OTHER INFORMATION: When present, Xaa is selected from Gln and Ser
<220> FEATURE:
<221> NAME/KEY: VARIANT
<222> LOCATION: (28)..(28)
<223> OTHER INFORMATION: When present, Xaa is Arg

<400> SEQUENCE: 5

Pro Ser Xaa Phe Leu Ser Pro Glu His Xaa Xaa Val Xaa Xaa Arg Xaa
1               5                   10                  15

Glu Ser Xaa Ser Pro Pro Ala Xaa Leu Xaa Pro Xaa
            20                  25
```

<210> SEQ ID NO 6
<211> LENGTH: 1101
<212> TYPE: DNA
<213> ORGANISM: Homo sapiens

<400> SEQUENCE: 6

```
atgtggaacg cgacgcccag cgaagagccg gggttcaacc tcacactggc cgacctggac      60
tgggatgctt ccccggcaa cgactcgctg ggcgacgagc tgctgcagct cttccccgcg     120
ccgctgctgg cgggcgtcac agccacctgc gtggcactct cgtggtgggg tatcgctggc     180
aacctgctca ccatgctggt ggtgtcgcgc ttccgcgagc tgcgcaccac caccaacctc     240
tacctgtcca gcatggcctt ctccgatctg ctcatcttcc tctgcatgcc cctggacctc     300
gttcgcctct ggcagtaccg gccctggaac ttcggcgacc tcctctgcaa actcttccaa     360
ttcgtcagtg agagctgcac ctacgccacg gtgctcacca tcacagcgct gagcgtcgag     420
cgctacttcg ccatctgctt cccactccgg gccaaggtgg tggtcaccaa ggggcgggtg     480
aagctggtca tcttcgtcat ctgggccgtg gccttctgca gcgccgggcc catcttcgtg     540
ctagtcgggg tggagcacga aacggcacc gacccttggg acaccaacga gtgccgcccc     600
accgagtttg cggtgcgctc tggactgctc acggtcatgg tgtgggtgtc cagcatcttc     660
ttcttccttc ctgtcttctg tctcacggtc ctctacagtc tcatcggcag aagctgtgg     720
cggaggaggc gcggcgatgc tgtcgtgggt gcctcgctca gggaccagaa ccacaagcaa     780
accgtgaaaa tgctggctgt agtggtgttt gccttcatcc tctgctggct ccccttccac     840
gtagggcgat atttattttc caatcctt gagcctggct ccttggagat tgctcagatc     900
agccagtact gcaacctcgt gtcctttgtc ctcttctacc tcagtgctgc catcaacccc     960
attctgtaca acatcatgtc caagaagtac cgggtggcag tgttcagact tctgggattc    1020
gaacccttct cccagagaaa gctctccact ctgaaagatg aaagttctcg ggcctggaca    1080
gaatctagta ttaatacatg a                                               1101
```

<210> SEQ ID NO 7
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octanoyl)

<400> SEQUENCE: 7

Pro Ser Ser Phe Leu Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 8
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)

-continued

```
<223> OTHER INFORMATION: Ser(O-octanoyl)

<400> SEQUENCE: 8

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 9
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octanoyl)

<400> SEQUENCE: 9

Phe Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 10
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octanoyl)

<400> SEQUENCE: 10

Ser Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 11
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Cmp (4-carboxymethyl-piperidine)
<220> FEATURE:
<221> NAME/KEY: SITE
<222> LOCATION: (2)..(2)
<223> OTHER INFORMATION: Ser(O-octanoyl)

<400> SEQUENCE: 11

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 12
<211> LENGTH: 27
<212> TYPE: PRT
<213> ORGANISM: Artificial sequence
```

-continued

```
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Mamb (3-aminomethyl-benzoic acid)
<220> FEATURE:
<221> NAME/KEY: SITE
<222> LOCATION: (2)..(2)
<223> OTHER INFORMATION: Ser(O-octanoyl)

<400> SEQUENCE: 12

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 13
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is cACC (cis-4-aminocyclohexane carboxylic
      acid)
<220> FEATURE:
<221> NAME/KEY: SITE
<222> LOCATION: (2)..(2)
<223> OTHER INFORMATION: Ser(O-octanoyl)

<400> SEQUENCE: 13

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 14
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is tACC (trans-4-aminocyclohexane
      carboxylic acid)
<220> FEATURE:
<221> NAME/KEY: SITE
<222> LOCATION: (2)..(2)
<223> OTHER INFORMATION: Ser(O-octanoyl)

<400> SEQUENCE: 14

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 15
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
```

```
<223> OTHER INFORMATION: Xaa is INP (isonipecotic acid, ie 4-
      carboxypiperidine)
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (13)..(13)
<223> OTHER INFORMATION: Lys(hexadecanoyl)

<400> SEQUENCE: 15

Xaa Ser Ser Phe Leu Ser Pro Glu His Gln Arg Val Lys Gln Arg Lys
1               5                   10                  15

Glu Ser Lys Lys Pro Pro Ala Lys Leu Gln Pro Arg
            20                  25

<210> SEQ ID NO 16
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is INP (isonipecotic acid, ie 4-
      carboxypiperidine)
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (19)
<223> OTHER INFORMATION: Lys(hexadecanoyl)

<400> SEQUENCE: 16

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 17
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is INP (isonipecotic acid, ie 4-
      carboxypiperidine)
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (26)
<223> OTHER INFORMATION: Lys(hexadecanoyl)

<400> SEQUENCE: 17

Xaa Ser Ser Phe Leu Ser Pro Glu His Gln Arg Val Gln Gln Arg Lys
1               5                   10                  15

Glu Ser Lys Lys Pro Pro Ala Lys Leu Lys Pro Arg
            20                  25

<210> SEQ ID NO 18
```

-continued

```
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (19)
<223> OTHER INFORMATION: Lys(hexadecanoyl)

<400> SEQUENCE: 18

Pro Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 19
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (19)
<223> OTHER INFORMATION: Lys(hexadecanoyl)

<400> SEQUENCE: 19

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 20
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: Aib
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (19)
<223> OTHER INFORMATION: Lys(hexadecanoyl)

<400> SEQUENCE: 20

Ala Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 21
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 21

Pro Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 22
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Ser(O-octyl)

<400> SEQUENCE: 22

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 23
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: Aib
<220> FEATURE:
<221> NAME/KEY: SITE
<222> LOCATION: (3)..(3)
<223> OTHER INFORMATION: Ser(O-octyl)

<400> SEQUENCE: 23

Ala Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 24
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)
```

<400> SEQUENCE: 24

Ala Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 25
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is cACC (cis-4-aminocyclohexane
      carboxylic acid)
<220> FEATURE:
<221> NAME/KEY: SITE
<222> LOCATION: (2)
<223> OTHER INFORMATION: Ser(O-octyl)

<400> SEQUENCE: 25

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 26
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Cmp (4-carboxymethyl-piperidine)
<220> FEATURE:
<221> NAME/KEY: SITE
<222> LOCATION: (2)
<223> OTHER INFORMATION: Ser(O-octyl)
<220> FEATURE:
<221> NAME/KEY: SITE
<222> LOCATION: (12)
<223> OTHER INFORMATION: Lys(hexadecanoyl)

<400> SEQUENCE: 26

Xaa Ser Phe Leu Ser Pro Glu His Gln Arg Val Lys Gln Arg Lys Glu
1               5                   10                  15

Ser Lys Lys Pro Pro Ala Lys Leu Gln Pro Arg
            20                  25

<210> SEQ ID NO 27
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (16)
<223> OTHER INFORMATION: Lys(hexadecanoyl)

<400> SEQUENCE: 27

Phe Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 28
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (19)
<223> OTHER INFORMATION: Lys(hexadecanoyl)

<400> SEQUENCE: 28

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 29
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: Aib
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (20)
<223> OTHER INFORMATION: Lys(hexadecanoyl)

<400> SEQUENCE: 29

Ala Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 30
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: MeGly
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE

```
<222> LOCATION: (26)
<223> OTHER INFORMATION: Lys(hexadecanoyl)

<400> SEQUENCE: 30

Gly Ser Ser Phe Leu Ser Pro Glu His Gln Arg Val Gln Gln Arg Lys
 1               5                  10                  15

Glu Ser Lys Lys Pro Pro Ala Lys Leu Lys Pro Arg
            20                  25

<210> SEQ ID NO 31
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 31

Ala Ser Ser Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 32
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is INP (isonipecotic acid, ie 4-
      carboxypiperidine)
<220> FEATURE:
<221> NAME/KEY: SITE
<222> LOCATION: (3)..(3)
<223> OTHER INFORMATION: Ser(O-octyl)

<400> SEQUENCE: 32

Xaa Ser Ser Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 33
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 33

Pro Ser Ser Phe Leu Ser Pro Glu His Gln Arg Val Gln Gln Arg Lys
 1               5                  10                  15

Glu Ser Lys Lys Pro Pro Ala Lys Leu Gln Pro Arg
            20                  25

<210> SEQ ID NO 34
<211> LENGTH: 28
```

```
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Ser(O-octyl)

<400> SEQUENCE: 34

Xaa Ser Ser Phe Leu Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 35
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (13)..(13)
<223> OTHER INFORMATION: Lys(hexadecanoyl)

<400> SEQUENCE: 35

Pro Ser Ser Phe Leu Ser Pro Glu His Gln Arg Val Lys Gln Arg Lys
1               5                   10                  15
Glu Ser Lys Lys Pro Pro Ala Lys Leu Gln Pro Arg
            20                  25

<210> SEQ ID NO 36
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Mamb (3-aminomethyl-benzoic acid)
<220> FEATURE:
<221> NAME/KEY: SITE
<222> LOCATION: (2)
<223> OTHER INFORMATION: Ser(O-octyl)
<220> FEATURE:
<221> NAME/KEY: SITE
<222> LOCATION: (12)
<223> OTHER INFORMATION: Lys(hexadecanoyl)

<400> SEQUENCE: 36

Xaa Ser Phe Leu Ser Pro Glu His Gln Arg Val Lys Gln Arg Lys Glu
1               5                   10                  15
Ser Lys Lys Pro Pro Ala Lys Leu Gln Pro Arg
            20                  25

<210> SEQ ID NO 37
<211> LENGTH: 28
<212> TYPE: PRT
<213> ORGANISM: Artificial sequence
<220> FEATURE:
```

<223> OTHER INFORMATION: Synthetic compound
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (19)
<223> OTHER INFORMATION: Lys(hexadecanoyl)

<400> SEQUENCE: 37

Ser Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 38
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (26)
<223> OTHER INFORMATION: Lys(hexadecanoyl)

<400> SEQUENCE: 38

Ala Ser Ser Phe Leu Ser Pro Glu His Gln Arg Val Gln Gln Arg Lys
1               5                   10                  15

Glu Ser Lys Lys Pro Pro Ala Lys Leu Lys Pro Arg
            20                  25

<210> SEQ ID NO 39
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: Aib
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (26)
<223> OTHER INFORMATION: Lys(hexadecanoyl)

<400> SEQUENCE: 39

Ala Ser Ser Phe Leu Ser Pro Glu His Gln Arg Val Gln Gln Arg Lys
1               5                   10                  15

Glu Ser Lys Lys Pro Pro Ala Lys Leu Lys Pro Arg
            20                  25

<210> SEQ ID NO 40
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE

```
<222> LOCATION: (3)..(3)
<223> OTHER INFORMATION: Xaa is NH-CH(n-C10H21)-C(O)

<400> SEQUENCE: 40

Pro Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 41
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Xaa is NH-CH(n-C10H21)-C(O)

<400> SEQUENCE: 41

Xaa Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 42
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Cmp (4-carboxymethyl-piperidine)
<220> FEATURE:
<221> NAME/KEY: SITE
<222> LOCATION: (2)
<223> OTHER INFORMATION: Xaa is NH-CH(n-C10H21)-C(O)

<400> SEQUENCE: 42

Xaa Xaa Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 43
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (13)..(13)
<223> OTHER INFORMATION: Lys(hexadecanoyl)
```

```
<400> SEQUENCE: 43

Xaa Ser Xaa Phe Leu Ser Pro Glu His Gln Arg Val Lys Gln Arg Lys
1               5                   10                  15

Glu Ser Lys Lys Pro Pro Ala Lys Leu Gln Pro Arg
            20                  25

<210> SEQ ID NO 44
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: MeGly
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (16)
<223> OTHER INFORMATION: Lys(hexadecanoyl)

<400> SEQUENCE: 44

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 45
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: Aib
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (16)
<223> OTHER INFORMATION: Lys(hexadecanoyl)

<400> SEQUENCE: 45

Ala Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 46
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is cACC (cis-4-aminocyclohexane carboxylic
      acid)
<220> FEATURE:
<221> NAME/KEY: SITE
<222> LOCATION: (2)
```

<223> OTHER INFORMATION: Xaa is NH-CH(n-C10H21)-C(O)
<220> FEATURE:
<221> NAME/KEY: SITE
<222> LOCATION: (18)
<223> OTHER INFORMATION: Lys(hexadecanoyl)

<400> SEQUENCE: 46

Xaa Xaa Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 47
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (20)
<223> OTHER INFORMATION: Lys(hexadecanoyl)

<400> SEQUENCE: 47

Xaa Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 48
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (26)
<223> OTHER INFORMATION: Lys(hexadecanoyl)

<400> SEQUENCE: 48

Ala Ser Xaa Phe Leu Ser Pro Glu His Gln Arg Val Gln Gln Arg Lys
1               5                   10                  15

Glu Ser Lys Lys Pro Pro Ala Lys Leu Lys Pro Arg
            20                  25

<210> SEQ ID NO 49
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Mamb (3-aminomethyl-benzoic acid)
<220> FEATURE:
<221> NAME/KEY: SITE

```
<222> LOCATION: (2)
<223> OTHER INFORMATION: Xaa is NH-CH(n-C10H21)-C(O)
<220> FEATURE:
<221> NAME/KEY: SITE
<222> LOCATION: (25)
<223> OTHER INFORMATION: Lys(hexadecanoyl)

<400> SEQUENCE: 49

Xaa Xaa Phe Leu Ser Pro Glu His Gln Arg Val Gln Gln Arg Lys Glu
1               5                   10                  15

Ser Lys Lys Pro Pro Ala Lys Leu Lys Pro Arg
            20                  25

<210> SEQ ID NO 50
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Xaa is NH-CH(n-C10H21)-C(O)

<400> SEQUENCE: 50

Ala Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 51
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is INP (isonipecotic acid, ie 4-
      carboxypiperidine)
<220> FEATURE:
<221> NAME/KEY: SITE
<222> LOCATION: (3)..(3)
<223> OTHER INFORMATION: Xaa is NH-CH(n-C10H21)-C(O)

<400> SEQUENCE: 51

Xaa Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 52
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Xaa is NH-CH(n-C10H21)-C(O)

<400> SEQUENCE: 52

Pro Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

```
<210> SEQ ID NO 53
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Xaa is NH-CH(n-C10H21)-C(O)

<400> SEQUENCE: 53

Xaa Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 54
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Xaa is NH-CH(n-C10H21)-C(O)

<400> SEQUENCE: 54

Ser Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 55
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Cmp (4-carboxymethyl-piperidine)
<220> FEATURE:
<221> NAME/KEY: SITE
<222> LOCATION: (2)
<223> OTHER INFORMATION: Xaa is NH-CH(n-C10H21)-C(O)

<400> SEQUENCE: 55

Xaa Xaa Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 56
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
```

```
<223> OTHER INFORMATION: Xaa is cACC (cis-4-aminocyclohexane
      carboxylic acid)
<220> FEATURE:
<221> NAME/KEY: SITE
<222> LOCATION: (2)
<223> OTHER INFORMATION: Xaa is NH-CH(n-C10H21)-C(O)

<400> SEQUENCE: 56

Xaa Xaa Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 57
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: MeGly
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (13)..(13)
<223> OTHER INFORMATION: Lys(hexadecanoyl)

<400> SEQUENCE: 57

Gly Ser Xaa Phe Leu Ser Pro Glu His Gln Arg Val Lys Gln Arg Lys
1               5                   10                  15

Glu Ser Lys Lys Pro Pro Ala Lys Leu Gln Pro Arg
            20                  25

<210> SEQ ID NO 58
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: Aib
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (13)
<223> OTHER INFORMATION: Lys(hexadecanoyl)

<400> SEQUENCE: 58

Ala Ser Xaa Phe Leu Ser Pro Glu His Gln Arg Val Lys Gln Arg Lys
1               5                   10                  15

Glu Ser Lys Lys Pro Pro Ala Lys Leu Gln Pro Arg
            20                  25

<210> SEQ ID NO 59
<211> LENGTH: 27
<212> TYPE: PRT
<213> ORGANISM: Artificial sequence
<220> FEATURE:
<223> OTHER INFORMATION: Synthetic compound
<220> FEATURE:
```

```
<221> NAME/KEY: SITE
<222> LOCATION: (1)..(1)
<223> OTHER INFORMATION: Xaa is Cmp (4-carboxymethyl-piperidine)
<220> FEATURE:
<221> NAME/KEY: SITE
<222> LOCATION: (2)
<223> OTHER INFORMATION: Xaa is NH-CH(n-C10H21)-C(O)
<220> FEATURE:
<221> NAME/KEY: SITE
<222> LOCATION: (12)
<223> OTHER INFORMATION: Lys(hexadecanoyl)

<400> SEQUENCE: 59

Xaa Xaa Phe Leu Ser Pro Glu His Gln Arg Val Lys Gln Arg Lys Glu
1               5                   10                  15

Ser Lys Lys Pro Pro Ala Lys Leu Gln Pro Arg
            20                  25

<210> SEQ ID NO 60
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is INP (isonipecotic acid, ie 4-
      carboxypiperidine)
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (16)
<223> OTHER INFORMATION: Lys(hexadecanoyl)

<400> SEQUENCE: 60

Xaa Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
                20                  25

<210> SEQ ID NO 61
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (19)
<223> OTHER INFORMATION: Lys(hexadecanoyl)

<400> SEQUENCE: 61

Xaa Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
                20                  25

<210> SEQ ID NO 62
```

```
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (19)
<223> OTHER INFORMATION: Lys(hexadecanoyl)

<400> SEQUENCE: 62

Ser Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 63
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: MeGly
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (20)
<223> OTHER INFORMATION: Lys(hexadecanoyl)

<400> SEQUENCE: 63

Gly Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 64
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (26)
<223> OTHER INFORMATION: Lys(hexadecanoyl)

<400> SEQUENCE: 64

Ala Ser Xaa Phe Leu Ser Pro Glu His Gln Arg Val Gln Gln Arg Lys
1               5                   10                  15

Glu Ser Lys Lys Pro Pro Ala Leu Lys Lys Pro Arg
            20                  25

<210> SEQ ID NO 65
<211> LENGTH: 28
<212> TYPE: PRT
<213> ORGANISM: Artificial sequence
```

```
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Xaa is NH-CH(n-C10H21)-C(O)
<220> FEATURE:
<221> NAME/KEY: SITE
<222> LOCATION: (26)
<223> OTHER INFORMATION: Lys(hexadecanoyl)

<400> SEQUENCE: 65

Pro Ser Xaa Phe Leu Ser Pro Glu His Gln Arg Val Gln Gln Arg Lys
1               5                   10                  15

Glu Ser Lys Lys Pro Pro Ala Lys Leu Lys Pro Arg
            20                  25

<210> SEQ ID NO 66
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octanoyl)
<220> FEATURE:
<221> NAME/KEY: SITE
<222> LOCATION: (13)..(13)
<223> OTHER INFORMATION: Lys(hexadecanoyl)

<400> SEQUENCE: 66

Pro Ser Ser Phe Leu Ser Pro Glu His Gln Arg Val Lys Gln Arg Lys
1               5                   10                  15

Glu Ser Lys Lys Pro Pro Ala Lys Leu Gln Pro Arg
            20                  25

<210> SEQ ID NO 67
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: SITE
<222> LOCATION: (3)..(3)
<223> OTHER INFORMATION: Ser(O-octanoyl)
<220> FEATURE:
<221> NAME/KEY: SITE
<222> LOCATION: (13)..(13)
<223> OTHER INFORMATION: Lys(hexadecanoyl)

<400> SEQUENCE: 67

Xaa Ser Ser Phe Leu Ser Pro Glu His Gln Arg Val Lys Gln Arg Lys
1               5                   10                  15

Glu Ser Lys Lys Pro Pro Ala Lys Leu Gln Pro Arg
            20                  25

<210> SEQ ID NO 68
<211> LENGTH: 28
<212> TYPE: PRT
<213> ORGANISM: Artificial sequence
<220> FEATURE:
<223> OTHER INFORMATION: Synthetic compound
<220> FEATURE:
```

-continued

```
<221> NAME/KEY: SITE
<222> LOCATION: (3)..(3)
<223> OTHER INFORMATION: Ser(O-octanoyl)
<220> FEATURE:
<221> NAME/KEY: SITE
<222> LOCATION: (13)..(13)
<223> OTHER INFORMATION: Lys(hexadecanoyl)

<400> SEQUENCE: 68

Ser Ser Ser Phe Leu Ser Pro Glu His Gln Arg Val Lys Gln Arg Lys
1               5                   10                  15

Glu Ser Lys Lys Pro Pro Ala Lys Leu Gln Pro Arg
            20                  25

<210> SEQ ID NO 69
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Cmp (4-carboxymethyl-piperidine)
<220> FEATURE:
<221> NAME/KEY: SITE
<222> LOCATION: (2)..(2)
<223> OTHER INFORMATION: Ser(O-octanoyl)
<220> FEATURE:
<221> NAME/KEY: SITE
<222> LOCATION: (12)
<223> OTHER INFORMATION: Lys(hexadecanoyl)

<400> SEQUENCE: 69

Xaa Ser Phe Leu Ser Pro Glu His Gln Arg Val Lys Gln Arg Lys Glu
1               5                   10                  15

Ser Lys Lys Pro Pro Ala Lys Leu Gln Pro Arg
            20                  25

<210> SEQ ID NO 70
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Cmp (4-carboxymethyl-piperidine)
<220> FEATURE:
<221> NAME/KEY: SITE
<222> LOCATION: (2)..(2)
<223> OTHER INFORMATION: Ser(O-octanoyl)
<220> FEATURE:
<221> NAME/KEY: SITE
<222> LOCATION: (15)
<223> OTHER INFORMATION: Lys(hexadecanoyl)

<400> SEQUENCE: 70

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 71
<211> LENGTH: 27
<212> TYPE: PRT
<213> ORGANISM: Artificial sequence
<220> FEATURE:
<223> OTHER INFORMATION: Synthetic compound
```

```
<220> FEATURE:
<221> NAME/KEY: SITE
<222> LOCATION: (1)..(1)
<223> OTHER INFORMATION: Xaa is cACC (cis-4-aminocyclohexane
      carboxylic acid)
<220> FEATURE:
<221> NAME/KEY: SITE
<222> LOCATION: (2)..(2)
<223> OTHER INFORMATION: Ser(O-octanoyl)
<220> FEATURE:
<221> NAME/KEY: SITE
<222> LOCATION: (15)
<223> OTHER INFORMATION: Lys(hexadecanoyl)

<400> SEQUENCE: 71

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 72
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is tACC (trans-4-aminocyclohexane
      carboxylic acid)
<220> FEATURE:
<221> NAME/KEY: SITE
<222> LOCATION: (2)..(2)
<223> OTHER INFORMATION: Ser(O-octanoyl)
<220> FEATURE:
<221> NAME/KEY: SITE
<222> LOCATION: (18)
<223> OTHER INFORMATION: Lys(hexadecanoyl)

<400> SEQUENCE: 72

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 73
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octanoyl)
<220> FEATURE:
<221> NAME/KEY: SITE
<222> LOCATION: (20)
<223> OTHER INFORMATION: Lys(hexadecanoyl)

<400> SEQUENCE: 73

Ser Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 74
<211> LENGTH: 28
<212> TYPE: PRT
```

```
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 74

Pro Ser Ser Phe Leu Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 75
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: MOD_RES
<222> LOCATION: (3)..(3)
<223> OTHER INFORMATION: Dpr(N-octanoyl)

<400> SEQUENCE: 75

Xaa Ser Ser Phe Leu Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 76
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 76

Ser Ser Ser Phe Leu Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 77
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)
<220> FEATURE:
<221> NAME/KEY: SITE
<222> LOCATION: (16)
<223> OTHER INFORMATION: Lys(hexadecanoyl)

<400> SEQUENCE: 77

Pro Ser Ser Phe Leu Ser Pro Glu His Gln Arg Val Gln Gln Arg Lys
```

```
                1               5                  10                  15
Glu Ser Lys Lys Pro Pro Ala Lys Leu Gln Pro Arg
            20                  25

<210> SEQ ID NO 78
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Mamb (3-aminomethyl-benzoic acid)
<220> FEATURE:
<221> NAME/KEY: MOD_RES
<222> LOCATION: (2)
<223> OTHER INFORMATION: Dpr(N-octanoyl)
<220> FEATURE:
<221> NAME/KEY: SITE
<222> LOCATION: (18)
<223> OTHER INFORMATION: Lys(hexadecanoyl)

<400> SEQUENCE: 78

Xaa Ser Phe Leu Ser Pro Glu His Gln Arg Val Gln Gln Arg Lys Glu
1               5                  10                  15

Ser Lys Lys Pro Pro Ala Lys Leu Gln Pro Arg
            20                  25

<210> SEQ ID NO 79
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 79

Pro Ser Ser Phe Leu Ser Pro Glu His Gln Arg Val Gln Gln Arg Lys
1               5                  10                  15

Glu Ser Lys Lys Pro Pro Ala Lys Leu Gln Pro Arg
            20                  25

<210> SEQ ID NO 80
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: MOD_RES
<222> LOCATION: (3)..(3)
<223> OTHER INFORMATION: Dpr(N-octanoyl)

<400> SEQUENCE: 80

Xaa Ser Ser Phe Leu Ser Pro Glu His Gln Arg Val Gln Gln Arg Lys
1               5                  10                  15

Glu Ser Lys Lys Pro Pro Ala Lys Leu Gln Pro Arg
            20                  25

<210> SEQ ID NO 81
```

```
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 81

Ser Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 82
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 82

Pro Ser Ser Phe Leu Ser Pro Glu His Ser Arg Val Ser Ser Arg Lys
1               5                   10                  15

Glu Ser Lys Lys Pro Pro Ala Lys Leu Ser Pro Arg
            20                  25

<210> SEQ ID NO 83
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Cmp (4-carboxymethyl-piperidine)
<220> FEATURE:
<221> NAME/KEY: MOD_RES
<222> LOCATION: (2)
<223> OTHER INFORMATION: Dpr(N-octanoyl)

<400> SEQUENCE: 83

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 84
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is cACC (cis-4-aminocyclohexane
      carboxylic acid)
<220> FEATURE:
<221> NAME/KEY: MOD_RES
<222> LOCATION: (2)
<223> OTHER INFORMATION: Dpr(N-octanoyl)
```

<400> SEQUENCE: 84

Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25

<210> SEQ ID NO 85
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)
<220> FEATURE:
<221> NAME/KEY: SITE
<222> LOCATION: (13)..(13)
<223> OTHER INFORMATION: Lys(hexadecanoyl)

<400> SEQUENCE: 85

Pro Ser Ser Phe Leu Ser Pro Glu His Gln Arg Val Lys Gln Arg Lys
1               5                   10                  15

Glu Ser Lys Lys Pro Pro Ala Lys Leu Gln Pro Arg
            20                  25

<210> SEQ ID NO 86
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: MOD_RES
<222> LOCATION: (3)..(3)
<223> OTHER INFORMATION: Dpr(N-octanoyl)
<220> FEATURE:
<221> NAME/KEY: SITE
<222> LOCATION: (13)..(13)
<223> OTHER INFORMATION: Lys(hexadecanoyl)

<400> SEQUENCE: 86

Xaa Ser Ser Phe Leu Ser Pro Glu His Gln Arg Val Lys Gln Arg Lys
1               5                   10                  15

Glu Ser Lys Lys Pro Pro Ala Lys Leu Gln Pro Arg
            20                  25

<210> SEQ ID NO 87
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)
<220> FEATURE:
<221> NAME/KEY: SITE
<222> LOCATION: (13)..(13)
<223> OTHER INFORMATION: Lys(hexadecanoyl)

<400> SEQUENCE: 87

Phe Ser Ser Phe Leu Ser Pro Glu His Gln Arg Val Lys Gln Arg Lys

```
                1               5                  10                  15
Glu Ser Lys Lys Pro Pro Ala Lys Leu Gln Pro Arg
            20                  25
```

<210> SEQ ID NO 88
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)
<220> FEATURE:
<221> NAME/KEY: SITE
<222> LOCATION: (13)..(13)
<223> OTHER INFORMATION: Lys(hexadecanoyl)

<400> SEQUENCE: 88

```
Ser Ser Ser Phe Leu Ser Pro Glu His Gln Arg Val Lys Gln Arg Lys
1               5                  10                  15
Glu Ser Lys Lys Pro Pro Ala Lys Leu Gln Pro Arg
            20                  25
```

<210> SEQ ID NO 89
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is DPro
<220> FEATURE:
<221> NAME/KEY: MOD_RES
<222> LOCATION: (3)..(3)
<223> OTHER INFORMATION: Dpr(N-octanoyl)
<220> FEATURE:
<221> NAME/KEY: SITE
<222> LOCATION: (16)
<223> OTHER INFORMATION: Lys(hexadecanoyl)

<400> SEQUENCE: 89

```
Xaa Ser Ser Phe Leu Ser Pro Glu His Gln Arg Val Gln Gln Arg Lys
1               5                  10                  15
Glu Ser Lys Lys Pro Pro Ala Lys Leu Gln Pro Arg
            20                  25
```

<210> SEQ ID NO 90
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Mamb (3-aminomethyl-benzoic acid)
<220> FEATURE:
<221> NAME/KEY: MOD_RES
<222> LOCATION: (2)
<223> OTHER INFORMATION: Dpr(N-octanoyl)
<220> FEATURE:
<221> NAME/KEY: SITE
<222> LOCATION: (15)
<223> OTHER INFORMATION: Lys(hexadecanoyl)

<400> SEQUENCE: 90

```
Xaa Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25
```

<210> SEQ ID NO 91
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)
<220> FEATURE:
<221> NAME/KEY: SITE
<222> LOCATION: (20)
<223> OTHER INFORMATION: Lys(hexadecanoyl)

<400> SEQUENCE: 91

```
Pro Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

<210> SEQ ID NO 92
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)
<220> FEATURE:
<221> NAME/KEY: SITE
<222> LOCATION: (20)
<223> OTHER INFORMATION: Lys(hexadecanoyl)

<400> SEQUENCE: 92

```
Ser Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25
```

<210> SEQ ID NO 93
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is Cmp (4-carboxymethyl-piperidine)
<220> FEATURE:
<221> NAME/KEY: MOD_RES
<222> LOCATION: (2)
<223> OTHER INFORMATION: Dpr(N-octanoyl)
<220> FEATURE:
<221> NAME/KEY: SITE
<222> LOCATION: (25)
<223> OTHER INFORMATION: Lys(hexadecanoyl)

<400> SEQUENCE: 93

```
Xaa Ser Phe Leu Ser Pro Glu His Gln Arg Val Gln Gln Arg Lys Glu
1               5                   10                  15
```

Ser Lys Lys Pro Pro Ala Lys Leu Lys Pro Arg
            20                  25

<210> SEQ ID NO 94
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)
<220> FEATURE:
<221> NAME/KEY: SITE
<222> LOCATION: (8)..(12)
<223> OTHER INFORMATION: Presence of an intramolecular bond formed
      between the side-chains of the amino acid residues in question.
      The intramolecular bond will typically be a lactam bridge.

<400> SEQUENCE: 94

Gly Ser Ser Phe Leu Ser Pro Glu His Gln Arg Lys Gln Gln Arg Lys
1               5                   10                  15

Glu Ser Lys Lys Pro Pro Ala Lys Leu Gln Pro Arg
            20                  25

<210> SEQ ID NO 95
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)
<220> FEATURE:
<221> NAME/KEY: SITE
<222> LOCATION: (10)..(14)
<223> OTHER INFORMATION: Presence of an intramolecular bond formed
      between the side-chains of the amino acid residues in question.
      The intramolecular bond will typically be a lactam bridge.

<400> SEQUENCE: 95

Gly Ser Ser Phe Leu Ser Pro Glu His Glu Arg Val Gln Lys Arg Lys
1               5                   10                  15

Glu Ser Lys Lys Pro Pro Ala Lys Leu Gln Pro Arg
            20                  25

<210> SEQ ID NO 96
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)
<220> FEATURE:
<221> NAME/KEY: SITE
<222> LOCATION: (16)..(20)
<223> OTHER INFORMATION: Presence of an intramolecular bond formed
      between the side-chains of the amino acid residues in question.
      The intramolecular bond will typically be a lactam bridge.

<400> SEQUENCE: 96

Gly Ser Ser Phe Leu Ser Pro Glu His Gln Arg Val Gln Gln Arg Lys
1               5                   10                  15

Glu Ser Lys Glu Pro Pro Ala Lys Leu Gln Pro Arg

```
                            20                  25

<210> SEQ ID NO 97
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (8)..(12)
<223> OTHER INFORMATION: Presence of an intramolecular bond formed
      between the side-chains of the amino acid residues in question.
      The intramolecular bond will typically be a lactam bridge.

<400> SEQUENCE: 97

Pro Ser Ser Phe Leu Ser Pro Glu His Gln Arg Lys Gln Gln Arg Lys
1               5                   10                  15

Glu Ser Lys Lys Pro Pro Ala Lys Leu Gln Pro Arg
            20                  25

<210> SEQ ID NO 98
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (10)..(14)
<223> OTHER INFORMATION: Presence of an intramolecular bond formed
      between the side-chains of the amino acid residues in question.
      The intramolecular bond will typically be a lactam bridge.

<400> SEQUENCE: 98

Pro Ser Ser Phe Leu Ser Pro Glu His Glu Arg Val Gln Lys Arg Lys
1               5                   10                  15

Glu Ser Lys Lys Pro Pro Ala Lys Leu Gln Pro Arg
            20                  25

<210> SEQ ID NO 99
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (1)..(1)
<223> OTHER INFORMATION: Orn
<220> FEATURE:
<221> NAME/KEY: SITE
<222> LOCATION: (2)
<223> OTHER INFORMATION: Ser(O-octyl)

<400> SEQUENCE: 99

Arg Ser Phe Leu Ser Pro Glu His Gln Arg Val Gln Gln Arg Lys Glu
1               5                   10                  15

Ser Lys Lys Pro Pro Ala Lys Leu Gln Pro Arg
            20                  25
```

```
<210> SEQ ID NO 100
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 100

Pro Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 101
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 101

Pro Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 102
<211> LENGTH: 8
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 102

Pro Ser Ser Phe Leu Ser Pro Lys
1               5

<210> SEQ ID NO 103
<211> LENGTH: 8
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 103

Pro Ser Ser Phe Leu Ser Pro Lys
1               5

<210> SEQ ID NO 104
<211> LENGTH: 8
<212> TYPE: PRT
<213> ORGANISM: Artificial sequence
<220> FEATURE:
```

```
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 104

Pro Ser Xaa Phe Leu Ser Pro Lys
1               5

<210> SEQ ID NO 105
<211> LENGTH: 8
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 105

Pro Ser Ser Phe Leu Ser Pro Tyr
1               5

<210> SEQ ID NO 106
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)
<220> FEATURE:
<221> NAME/KEY: SITE
<222> LOCATION: (19)
<223> OTHER INFORMATION: Lys(hexadecanoyl-isoGlu)

<400> SEQUENCE: 106

Pro Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 107
<211> LENGTH: 23
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)
<220> FEATURE:
<221> NAME/KEY: SITE
<222> LOCATION: (19)
<223> OTHER INFORMATION: Lys(hexadecanoyl-isoGlu)

<400> SEQUENCE: 107

Pro Ser Ser Phe Leu Ser Pro Glu His Ser Arg Val Ser Ser Arg Lys
1               5                   10                  15

Glu Ser Lys Lys Pro Pro Ala
            20

<210> SEQ ID NO 108
<211> LENGTH: 28
```

```
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 108

Pro Ser Ser Phe Leu Ser Pro Glu His Ser Arg Val Ser Ser Arg Lys
1               5                   10                  15

Glu Ser Ser Lys Pro Pro Ala Lys Leu Ser Pro Arg
            20                  25

<210> SEQ ID NO 109
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 109

Pro Ser Ser Phe Leu Ser Pro Glu His Ser Arg Val Ser Ser Arg Lys
1               5                   10                  15

Glu Ser Lys Ser Pro Pro Ala Lys Leu Ser Pro Arg
            20                  25

<210> SEQ ID NO 110
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 110

Pro Ser Ser Phe Leu Ser Pro Glu His Ser Arg Val Ser Ser Arg Lys
1               5                   10                  15

Glu Ser Ser Ser Pro Pro Ala Lys Leu Ser Pro Arg
            20                  25

<210> SEQ ID NO 111
<211> LENGTH: 15
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 111

Pro Ser Ser Phe Leu Ser Pro Glu His Ser Arg Pro Ser Ser Arg
1               5                   10                  15

<210> SEQ ID NO 112
<211> LENGTH: 28
<212> TYPE: PRT
<213> ORGANISM: Artificial sequence
```

```
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 112

Pro Ser Ser Phe Leu Ser Pro Glu His Ser Arg Val Ser Ser Arg Pro
1               5                   10                  15

Glu Ser Ser Ser Pro Pro Ala Lys Leu Ser Pro Arg
            20                  25

<210> SEQ ID NO 113
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 113

Pro Ser Ser Phe Leu Ser Pro Glu His Ser Arg Pro Ser Ser Arg Pro
1               5                   10                  15

Glu Ser Ser Ser Pro Pro Ala Lys Leu Ser Pro Arg
            20                  25

<210> SEQ ID NO 114
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 114

Pro Ser Ser Phe Leu Ser Pro Glu His Gln Ser Val Gln Gln Arg Lys
1               5                   10                  15

Glu Ser Lys Lys Pro Pro Ala Lys Leu Gln Pro Arg
            20                  25

<210> SEQ ID NO 115
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 115

Pro Ser Ser Phe Leu Ser Pro Glu His Gln Arg Val Gln Gln Ser Lys
1               5                   10                  15

Glu Ser Lys Lys Pro Pro Ala Lys Leu Gln Pro Arg
            20                  25

<210> SEQ ID NO 116
<211> LENGTH: 28
<212> TYPE: PRT
```

```
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 116

Pro Ser Ser Phe Leu Ser Pro Glu His Gln Arg Val Gln Gln Arg Ser
1               5                   10                  15

Glu Ser Lys Lys Pro Pro Ala Lys Leu Gln Pro Arg
            20                  25

<210> SEQ ID NO 117
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 117

Pro Ser Ser Phe Leu Ser Pro Glu His Gln Arg Val Gln Gln Arg Lys
1               5                   10                  15

Glu Ser Ser Lys Pro Pro Ala Lys Leu Gln Pro Arg
            20                  25

<210> SEQ ID NO 118
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 118

Pro Ser Ser Phe Leu Ser Pro Glu His Gln Arg Val Gln Gln Arg Lys
1               5                   10                  15

Glu Ser Lys Ser Pro Pro Ala Lys Leu Gln Pro Arg
            20                  25

<210> SEQ ID NO 119
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 119

Pro Ser Ser Phe Leu Ser Pro Glu His Gln Arg Val Gln Gln Arg Lys
1               5                   10                  15

Glu Ser Lys Lys Pro Pro Ala Ser Leu Gln Pro Arg
            20                  25

<210> SEQ ID NO 120
<211> LENGTH: 28
```

```
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 120

Pro Ser Ser Phe Leu Ser Pro Glu His Gln Arg Val Gln Gln Arg Lys
1               5                   10                  15

Glu Ser Lys Lys Pro Pro Ala Lys Leu Gln Pro Ser
            20                  25

<210> SEQ ID NO 121
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 121

Pro Ser Ser Phe Leu Ser Pro Tyr His Gln Arg Val Gln Gln Arg Lys
1               5                   10                  15

Glu Ser Lys Lys Pro Pro Ala Lys Leu Gln Pro Arg
            20                  25

<210> SEQ ID NO 122
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 122

Pro Ser Ser Phe Leu Ser Pro Glu His Gln Arg Val Gln Tyr Arg Lys
1               5                   10                  15

Glu Ser Lys Lys Pro Pro Ala Lys Leu Gln Pro Arg
            20                  25

<210> SEQ ID NO 123
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 123

Pro Ser Ser Phe Leu Ser Pro Glu His Gln Arg Val Gln Gln Arg Lys
1               5                   10                  15

Glu Ser Lys Lys Pro Pro Ala Tyr Leu Gln Pro Arg
            20                  25

<210> SEQ ID NO 124
```

```
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(octanoyl)

<400> SEQUENCE: 124

Pro Ser Ser Phe Leu Ser Pro Tyr His Gln Arg Val Gln Tyr Arg Lys
1               5                   10                  15
Glu Ser Lys Lys Pro Pro Ala Tyr Leu Gln Pro Arg
            20                  25

<210> SEQ ID NO 125
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Ser(O-octyl)

<400> SEQUENCE: 125

Pro Ser Ser Phe Leu Ser Pro Glu His Gln Arg Val Gln Gln Arg Lys
1               5                   10                  15
Glu Ser Lys Lys Pro Pro Ala Lys Leu Gln Pro Arg
            20                  25

<210> SEQ ID NO 126
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Ser(O-octyl)

<400> SEQUENCE: 126

Pro Ser Ser Phe Leu Ser Pro Glu His Gln Arg Val Gln Arg Lys Glu
1               5                   10                  15
Ser Lys Lys Pro Pro Ala Lys Leu Gln Pro Arg
            20                  25

<210> SEQ ID NO 127
<211> LENGTH: 23
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Ser(O-octyl)

<400> SEQUENCE: 127

Pro Ser Ser Phe Leu Ser Pro Glu His Gln Arg Val Gln Gln Arg Lys
1               5                   10                  15
Glu Ser Lys Lys Pro Pro Ala
            20
```

<210> SEQ ID NO 128
<211> LENGTH: 18
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Ser(O-octyl)

<400> SEQUENCE: 128

Pro Ser Ser Phe Leu Ser Pro Glu His Gln Arg Val Gln Gln Arg Lys
1               5                   10                  15

Glu Ser

<210> SEQ ID NO 129
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Xaa is NH-CH(n-C10H21)-C(O)

<400> SEQUENCE: 129

Pro Ser Xaa Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 130
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Xaa is NH-CH(n-C10H21)-C(O)

<400> SEQUENCE: 130

Pro Ser Xaa Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 131
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (1)..(1)
<223> OTHER INFORMATION: Xaa is cACC (cis-4-aminocyclohexane carboxylic
      acid)
<220> FEATURE:
<221> NAME/KEY: SITE
<222> LOCATION: (2)
<223> OTHER INFORMATION: Ser(O-octyl)

<400> SEQUENCE: 131

Xaa Ser Phe Leu Ser Pro Glu His Gln Arg Val Gln Gln Arg Lys Glu
1               5                   10                  15

```
Ser Lys Lys Pro Pro Ala Lys Leu Gln Pro Arg
            20                  25

<210> SEQ ID NO 132
<211> LENGTH: 11
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 132

Pro Ser Ser Phe Leu Ser Pro Glu His Ser Arg
1               5                   10

<210> SEQ ID NO 133
<211> LENGTH: 15
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 133

Pro Ser Ser Phe Leu Ser Pro Glu His Ser Arg Val Ser Ser Arg
1               5                   10                  15

<210> SEQ ID NO 134
<211> LENGTH: 28
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)..(3)
<223> OTHER INFORMATION: Ser(O-octyl)

<400> SEQUENCE: 134

Pro Ser Ser Phe Leu Ser Pro Glu His Ser Arg Val Ser Ser Arg Lys
1               5                   10                  15

Glu Ser Lys Lys Pro Pro Ala Lys Leu Ser Pro Arg
            20                  25

<210> SEQ ID NO 135
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 135

Pro Ser Ser Phe Leu Ser Pro Glu His Gln Arg Val Gln Gln Arg Lys
1               5                   10                  15

Glu Ser Lys Lys Pro Pro Ala Lys Leu Gln Pro
            20                  25
```

```
<210> SEQ ID NO 136
<211> LENGTH: 26
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 136

Pro Ser Ser Phe Leu Ser Pro Glu His Gln Arg Val Gln Gln Arg Lys
1               5                   10                  15

Glu Ser Lys Lys Pro Pro Ala Lys Leu Gln
            20                  25

<210> SEQ ID NO 137
<211> LENGTH: 25
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 137

Pro Ser Ser Phe Leu Ser Pro Glu His Gln Arg Val Gln Gln Arg Lys
1               5                   10                  15

Glu Ser Lys Lys Pro Pro Ala Lys Leu
            20                  25

<210> SEQ ID NO 138
<211> LENGTH: 24
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 138

Pro Ser Ser Phe Leu Ser Pro Glu His Gln Arg Val Gln Gln Arg Lys
1               5                   10                  15

Glu Ser Lys Lys Pro Pro Ala Lys
            20

<210> SEQ ID NO 139
<211> LENGTH: 23
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 139

Pro Ser Ser Phe Leu Ser Pro Glu His Gln Arg Val Gln Gln Arg Lys
1               5                   10                  15

Glu Ser Lys Lys Pro Pro Ala
            20
```

```
<210> SEQ ID NO 140
<211> LENGTH: 22
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 140

Pro Ser Ser Phe Leu Ser Pro Glu His Gln Arg Val Gln Gln Arg Lys
1               5                   10                  15

Glu Ser Lys Lys Pro Pro
            20

<210> SEQ ID NO 141
<211> LENGTH: 21
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 141

Pro Ser Ser Phe Leu Ser Pro Glu His Gln Arg Val Gln Gln Arg Lys
1               5                   10                  15

Glu Ser Lys Lys Pro
            20

<210> SEQ ID NO 142
<211> LENGTH: 20
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 142

Pro Ser Ser Phe Leu Ser Pro Glu His Gln Arg Val Gln Gln Arg Lys
1               5                   10                  15

Glu Ser Lys Lys
            20

<210> SEQ ID NO 143
<211> LENGTH: 19
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 143

Pro Ser Ser Phe Leu Ser Pro Glu His Gln Arg Val Gln Gln Arg Lys
1               5                   10                  15

Glu Ser Lys
```

<210> SEQ ID NO 144
<211> LENGTH: 18
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 144

Pro Ser Ser Phe Leu Ser Pro Glu His Gln Arg Val Gln Gln Arg Lys
1               5                   10                  15

Glu Ser

<210> SEQ ID NO 145
<211> LENGTH: 17
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 145

Pro Ser Ser Phe Leu Ser Pro Glu His Gln Arg Val Gln Gln Arg Lys
1               5                   10                  15

Glu

<210> SEQ ID NO 146
<211> LENGTH: 16
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 146

Pro Ser Ser Phe Leu Ser Pro Glu His Gln Arg Val Gln Gln Arg Lys
1               5                   10                  15

<210> SEQ ID NO 147
<211> LENGTH: 15
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 147

Pro Ser Ser Phe Leu Ser Pro Glu His Gln Arg Val Gln Gln Arg
1               5                   10                  15

<210> SEQ ID NO 148
<211> LENGTH: 14
<212> TYPE: PRT
<213> ORGANISM: Artificial sequence
<220> FEATURE:
<223> OTHER INFORMATION: Synthetic compound -continued

```
<220> FEATURE:
<221> NAME/KEY: MOD_RES
<222> LOCATION: (3)..(3)
<223> OTHER INFORMATION: Dpr(N-octanoyl)

<400> SEQUENCE: 148

Pro Ser Ser Phe Leu Ser Pro Glu His Gln Arg Val Gln Gln
1               5                   10

<210> SEQ ID NO 149
<211> LENGTH: 13
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 149

Pro Ser Ser Phe Leu Ser Pro Glu His Gln Arg Val Gln
1               5                   10

<210> SEQ ID NO 150
<211> LENGTH: 12
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 150

Pro Ser Ser Phe Leu Ser Pro Glu His Gln Arg Val
1               5                   10

<210> SEQ ID NO 151
<211> LENGTH: 11
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 151

Pro Ser Ser Phe Leu Ser Pro Glu His Gln Arg
1               5                   10

<210> SEQ ID NO 152
<211> LENGTH: 10
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 152

Pro Ser Ser Phe Leu Ser Pro Glu His Gln
1               5                   10
```

```
<210> SEQ ID NO 153
<211> LENGTH: 9
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 153

Pro Ser Ser Phe Leu Ser Pro Glu His
1               5

<210> SEQ ID NO 154
<211> LENGTH: 8
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 154

Pro Ser Ser Phe Leu Ser Pro Glu
1               5

<210> SEQ ID NO 155
<211> LENGTH: 7
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 155

Pro Ser Ser Phe Leu Ser Pro
1               5

<210> SEQ ID NO 156
<211> LENGTH: 6
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 156

Pro Ser Ser Phe Leu Ser
1               5

<210> SEQ ID NO 157
<211> LENGTH: 5
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)
```

```
<400> SEQUENCE: 157

Pro Ser Ser Phe Leu
1               5

<210> SEQ ID NO 158
<211> LENGTH: 27
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 158

Pro Ser Ser Phe Leu Ser Pro Glu His Ser Arg Val Ser Ser Arg Lys
1               5                   10                  15

Glu Ser Lys Lys Pro Pro Ala Lys Leu Ser Pro
            20                  25

<210> SEQ ID NO 159
<211> LENGTH: 26
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 159

Pro Ser Ser Phe Leu Ser Pro Glu His Ser Arg Val Ser Ser Arg Lys
1               5                   10                  15

Glu Ser Lys Lys Pro Pro Ala Lys Leu Ser
            20                  25

<210> SEQ ID NO 160
<211> LENGTH: 25
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 160

Pro Ser Ser Phe Leu Ser Pro Glu His Ser Arg Val Ser Ser Arg Lys
1               5                   10                  15

Glu Ser Lys Lys Pro Pro Ala Lys Leu
            20                  25

<210> SEQ ID NO 161
<211> LENGTH: 24
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 161
```

Pro Ser Ser Phe Leu Ser Pro Glu His Ser Arg Val Ser Ser Arg Lys
1               5                   10                  15

Glu Ser Lys Lys Pro Pro Ala Lys
            20

<210> SEQ ID NO 162
<211> LENGTH: 23
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 162

Pro Ser Ser Phe Leu Ser Pro Glu His Ser Arg Val Ser Ser Arg Lys
1               5                   10                  15

Glu Ser Lys Lys Pro Pro Ala
            20

<210> SEQ ID NO 163
<211> LENGTH: 22
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 163

Pro Ser Ser Phe Leu Ser Pro Glu His Ser Arg Val Ser Ser Arg Lys
1               5                   10                  15

Glu Ser Lys Lys Pro Pro
            20

<210> SEQ ID NO 164
<211> LENGTH: 21
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 164

Pro Ser Ser Phe Leu Ser Pro Glu His Ser Arg Val Ser Ser Arg Lys
1               5                   10                  15

Glu Ser Lys Lys Pro
            20

<210> SEQ ID NO 165
<211> LENGTH: 20
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 165

```
Pro Ser Ser Phe Leu Ser Pro Glu His Ser Arg Val Ser Ser Arg Lys
1               5                   10                  15

Glu Ser Lys Lys
            20

<210> SEQ ID NO 166
<211> LENGTH: 19
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 166

Pro Ser Ser Phe Leu Ser Pro Glu His Ser Arg Val Ser Ser Arg Lys
1               5                   10                  15

Glu Ser Lys

<210> SEQ ID NO 167
<211> LENGTH: 18
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 167

Pro Ser Ser Phe Leu Ser Pro Glu His Ser Arg Val Ser Ser Arg Lys
1               5                   10                  15

Glu Ser

<210> SEQ ID NO 168
<211> LENGTH: 17
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 168

Pro Ser Ser Phe Leu Ser Pro Glu His Ser Arg Val Ser Ser Arg Lys
1               5                   10                  15

Glu

<210> SEQ ID NO 169
<211> LENGTH: 16
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 169

Pro Ser Ser Phe Leu Ser Pro Glu His Ser Arg Val Ser Ser Arg Lys
```

<210> SEQ ID NO 170
<211> LENGTH: 15
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 170

Pro Ser Ser Phe Leu Ser Pro Glu His Ser Arg Val Ser Ser Arg
1               5                   10                  15

<210> SEQ ID NO 171
<211> LENGTH: 14
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 171

Pro Ser Ser Phe Leu Ser Pro Glu His Ser Arg Val Ser Ser
1               5                   10

<210> SEQ ID NO 172
<211> LENGTH: 13
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 172

Pro Ser Ser Phe Leu Ser Pro Glu His Ser Arg Val Ser
1               5                   10

<210> SEQ ID NO 173
<211> LENGTH: 12
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 173

Pro Ser Ser Phe Leu Ser Pro Glu His Ser Arg Val
1               5                   10

<210> SEQ ID NO 174
<211> LENGTH: 11
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES

```
<222> LOCATION: (3)..(3)
<223> OTHER INFORMATION: Dpr(N-octanoyl)

<400> SEQUENCE: 174

Pro Ser Ser Phe Leu Ser Pro Glu His Ser Arg
1               5                   10

<210> SEQ ID NO 175
<211> LENGTH: 10
<212> TYPE: PRT
<213> ORGANISM: Artificial sequence
<220> FEATURE:
<223> OTHER INFORMATION: Synthetic compound
<220> FEATURE:
<221> NAME/KEY: MOD_RES
<222> LOCATION: (3)..(3)
<223> OTHER INFORMATION: Dpr(N-octanoyl)

<400> SEQUENCE: 175

Pro Ser Ser Phe Leu Ser Pro Glu His Ser
1               5                   10

<210> SEQ ID NO 176
<211> LENGTH: 23
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 176

Pro Ser Xaa Phe Leu Ser Pro Glu His Gln Arg Val Gln Gln Arg Lys
1               5                   10                  15

Glu Ser Lys Lys Pro Pro Ala
            20

<210> SEQ ID NO 177
<211> LENGTH: 22
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 177

Pro Ser Xaa Phe Leu Ser Pro Glu His Gln Arg Val Gln Gln Arg Lys
1               5                   10                  15

Glu Ser Lys Lys Pro Pro
            20

<210> SEQ ID NO 178
<211> LENGTH: 21
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 178
```

```
Pro Ser Xaa Phe Leu Ser Pro Glu His Gln Arg Val Gln Gln Arg Lys
1               5                   10                  15

Glu Ser Lys Lys Pro
            20
```

<210> SEQ ID NO 179
<211> LENGTH: 20
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 179

```
Pro Ser Xaa Phe Leu Ser Pro Glu His Gln Arg Val Gln Gln Arg Lys
1               5                   10                  15

Glu Ser Lys Lys
            20
```

<210> SEQ ID NO 180
<211> LENGTH: 19
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 180

```
Pro Ser Xaa Phe Leu Ser Pro Glu His Gln Arg Val Gln Gln Arg Lys
1               5                   10                  15

Glu Ser Lys
```

<210> SEQ ID NO 181
<211> LENGTH: 18
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 181

```
Pro Ser Xaa Phe Leu Ser Pro Glu His Gln Arg Val Gln Gln Arg Lys
1               5                   10                  15

Glu Ser
```

<210> SEQ ID NO 182
<211> LENGTH: 17
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 182

```
Pro Ser Xaa Phe Leu Ser Pro Glu His Gln Arg Val Gln Gln Arg Lys
```

```
1               5                   10                  15

Glu

<210> SEQ ID NO 183
<211> LENGTH: 16
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 183

Pro Ser Xaa Phe Leu Ser Pro Glu His Gln Arg Val Gln Gln Arg Lys
1               5                   10                  15

<210> SEQ ID NO 184
<211> LENGTH: 15
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 184

Pro Ser Xaa Phe Leu Ser Pro Glu His Gln Arg Val Gln Gln Arg
1               5                   10                  15

<210> SEQ ID NO 185
<211> LENGTH: 14
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 185

Pro Ser Xaa Phe Leu Ser Pro Glu His Gln Arg Val Gln Gln
1               5                   10

<210> SEQ ID NO 186
<211> LENGTH: 13
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 186

Pro Ser Xaa Phe Leu Ser Pro Glu His Gln Arg Val Gln
1               5                   10

<210> SEQ ID NO 187
<211> LENGTH: 12
<212> TYPE: PRT
<213> ORGANISM: Artificial sequence
<220> FEATURE:
<223> OTHER INFORMATION: Synthetic compound
```

```
<220> FEATURE:
<221> NAME/KEY: SITE
<222> LOCATION: (3)
<223> OTHER INFORMATION: Xaa is NH-CH(n-C10H21)-C(O)

<400> SEQUENCE: 187

Pro Ser Xaa Phe Leu Ser Pro Glu His Gln Arg Val
1               5                   10

<210> SEQ ID NO 188
<211> LENGTH: 11
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 188

Pro Ser Xaa Phe Leu Ser Pro Glu His Gln Arg
1               5                   10

<210> SEQ ID NO 189
<211> LENGTH: 10
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 189

Pro Ser Xaa Phe Leu Ser Pro Glu His Gln
1               5                   10

<210> SEQ ID NO 190
<211> LENGTH: 9
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 190

Pro Ser Xaa Phe Leu Ser Pro Glu His
1               5

<210> SEQ ID NO 191
<211> LENGTH: 8
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 191

Pro Ser Xaa Phe Leu Ser Pro Glu
1               5
```

```
<210> SEQ ID NO 192
<211> LENGTH: 7
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 192

Pro Ser Xaa Phe Leu Ser Pro
1               5

<210> SEQ ID NO 193
<211> LENGTH: 6
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 193

Pro Ser Xaa Phe Leu Ser
1               5

<210> SEQ ID NO 194
<211> LENGTH: 5
<212> TYPE: PRT
<213> ORGANISM: Artificial sequence
<220> FEATURE:
<223> OTHER INFORMATION: Synthetic compound
<220> FEATURE:
<221> NAME/KEY: SITE
<222> LOCATION: (3)
<223> OTHER INFORMATION: Xaa is NH-CH(n-C10H21)-C(O)

<400> SEQUENCE: 194

Pro Ser Xaa Phe Leu
1               5

<210> SEQ ID NO 195
<211> LENGTH: 28
<212> TYPE: PRT
<213> ORGANISM: Rattus norvegicus
<220> FEATURE:
<221> NAME/KEY: SITE
<222> LOCATION: (3)..(3)
<223> OTHER INFORMATION: Ser(O-octanol)

<400> SEQUENCE: 195

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
                20                  25
```

The invention claimed is:

1. A compound having the formula I:

$$R^1—Z—R^2 \quad (I)$$

wherein $R^1$ is hydrogen, $C_{1-4}$ alkyl, formyl, acetyl, trifluoroacetyl or benzoyl;

$R^2$ is OH or $NH_2$; and

Z is an amino acid sequence having the formula Ia:

$X^1$-$X^2$-$X^3$-Phe-Leu-Ser-Pro-$X^8$-His-$X^{10}$-$X^{11}$-$X^{12}$-$X^{13}$-$X^{14}$-$X^{15}$-$X^{16}$-Glu-Ser-$X^{19}$-$X^{20}$-Pro-Pro-Ala-$X^{24}$-Leu-$X^{26}$-Pro $X^{28}$ (Ia) (SEQ ID NO: 2)

or is a truncated form thereof lacking from 1 to 23 amino acids from the C-terminus;

wherein $X^1$ is Pro;

$X^2$ is Ser; and $X^3$ is selected from the group consisting of:

$$-NH-CH[(CH_2)_n-O-R^3]-C(O)-;\quad\quad (i)$$

$$-NH-CH(R^4)-C(O)-;\quad\quad (ii)$$

$$-NH-CH[(CH_2)_m-O-R^5]-C(O)-;\text{ and}\quad\quad (iii)$$

$$-NH-CH[(CH_2)_p-NH-R^6]-C(O)-;\quad\quad (iv)$$

wherein
$R^3$ and $R^4$ are, independently, $C_{1-35}$-alkyl or $C_{1-35}$-alkenyl groups;
$R^5$ and $R^6$ are, independently, $C_{1-35}$-acyl groups; and
n, m and p are integers 1, 2, 3, 4 or 5; and
when present
$X^8$ is selected from Glu, Lys and Tyr;
$X^{10}$ is selected from Gln, Glu and Ser;
$X^{11}$ is selected from Arg, Lys and Ser;
$X^{12}$ is selected from Val, Ala, Pro, Lys, Thr and Leu;
$X^{13}$ is selected from Gln and Ser;
$X^{14}$ is selected from Gln, Lys, Tyr and Ser, or is absent;
$X^{15}$ is selected from Arg and Ser;
$X^{16}$ is selected from Lys, Ser and Pro;
$X^{19}$ is selected from Lys and Ser;
$X^{20}$ is selected from Lys, Glu and Ser;
$X^{24}$ is selected from Lys, Tyr and Ser;
$X^{26}$ is selected from Gln and Ser; and
$X^{28}$ is selected from Arg and Ser;
or a pharmaceutically acceptable salt thereof.

2. The compound according to claim 1, having the formula I:

$$R^1-Z-R^2\quad\quad (I)$$

wherein
$R^1$ is hydrogen, $C_{1-4}$ alkyl, formyl, acetyl, trifluoroacetyl or benzoyl;
$R^2$ is —OH or —NH$_2$; and
Z is an amino acid sequence having the formula Ib:

$X^1$-$X^2$-$X^3$-Phe-Leu-Ser-Pro-Glu-His-$X^{10}$-$X^{11}$-$X^{12}$-$X^{13}$-$X^{14}$-Arg-$X^{16}$-Glu-Ser-$X^{19}$-$X^{20}$-Pro-Pro-Ala-$X^{24}$-Leu-$X^{26}$-Pro-$X^{28}$  (Ib) (SEQ ID NO: 3)

or is a truncated form thereof lacking from 1 to 23 amino acids from the C-terminus;
wherein
$X^1$ is Pro;
$X^2$ is Ser; and
$X^3$ is selected from the group consisting of:

$$-NH-CH[(CH_2)_n-O-R^3]-C(O)-;\quad\quad (i)$$

$$-NH-CH(R^4)-C(O)-;\quad\quad (ii)$$

$$-NH-CH[(CH_2)_m-O-R^5]-C(O)-;\text{ and}\quad\quad (iii)$$

$$-NH-CH[(CH_2)_p-NH-R^6]-C(O)-;\quad\quad (iv)$$

wherein
$R^3$ and $R^4$ are, independently, $C_{1-35}$-alkyl or $C_{1-35}$-alkenyl groups;
$R^5$ and $R^6$ are, independently, $C_{1-35}$-acyl groups; and
n, m and p are integers 1, 2, 3, 4 or 5; and
when present
$X^{10}$ is selected from Gln and Ser;
$X^{11}$ is selected from Arg and Lys;
$X^{12}$ is selected from Val, Ala, Thr and Leu;
$X^{13}$ is selected from Gln and Ser;
$X^{14}$ is selected from Gln and Ser, or is absent;
$X^{16}$ is Lys;
$X^{19}$ is Lys;
$X^{20}$ is Lys;
$X^{24}$ is Lys;
$X^{26}$ is selected from Gln and Ser; and
$X^{28}$ is Arg;
or a pharmaceutically acceptable salt thereof.

3. The compound according to claim 2, having the formula I:

$$R^1-Z-R^2\quad\quad (I)$$

wherein
$R^1$ is hydrogen, $C_{1-4}$ alkyl, formyl, acetyl, trifluoroacetyl or benzoyl;
$R^2$ is —OH or —NH$_2$; and
Z is an amino acid sequence having the formula Ia:

$X^1$-$X^2$-$X^3$-Phe-Leu-Ser-Pro-Glu-His-$X^{10}$-$X^{11}$-$X^{12}$-$X^{13}$-$X^{14}$-Arg-$X^{16}$-Glu-Ser-$X^{19}$-$X^{20}$-Pro-Pro-Ala-$X^{24}$-Leu-$X^{26}$-Pro $X^{28}$  (Ib) (SEQ ID NO: 3)

or is a truncated form thereof lacking from 1 to 23 amino acids from the C-terminus;
wherein
$X^1$ is Pro;
$X^2$ is Ser; and
$X^3$ is selected from the group consisting of:

$$-NH-CH[(CH_2)_n-O-R^3]-C(O)-;\quad\quad (i)$$

$$-NH-CH(R^4)-C(O)-;\quad\quad (ii)$$

$$-NH-CH[(CH_2)_m-O-R^5]-C(O)-;\text{ and}\quad\quad (iii)$$

$$-NH-CH[(CH_2)_p-NH-R^6]-C(O)-;\quad\quad (iv)$$

wherein
$R^3$ and $R^4$ are $C_{1-35}$-alkyl or $C_{1-35}$-alkenyl groups;
$R^5$ and $R^6$ are $C_{1-35}$-acyl groups; and
n, m and p are integers 1, 2, 3, 4 or 5; and
when present
$X^{10}$ is Gln;
$X^{11}$ is selected from Arg and Lys;
$X^{12}$ is selected from Val, Ala, Thr and Leu;
$X^{13}$ is Gln;
$X^{14}$ is Gln or is absent;
$X^{16}$ is Lys;
$X^{19}$ is Lys;
$X^{20}$ is Lys;
$X^{24}$ is Lys;
$X^{26}$ is Gln; and
$X^{28}$ is Arg;
or a pharmaceutically acceptable salt thereof.

4. The compound according to claim 1, wherein Z is an amino acid sequence having the formula Ic:

Pro-Ser-$X^3$-Phe-Leu-Ser-Pro-Glu-His-$X^{10}$-$X^{11}$-$X^{12}$-$X^{13}$-$X^{14}$-Arg-$X^{16}$-Glu-Ser-$X^{19}$-$X^{20}$-Pro-Pro-Ala-$X^{24}$-Leu-$X^{26}$-Pro-$X^{28}$  (Ic) (SEQ ID NO: 4)

or is a truncated form thereof lacking from 1 to 23 amino acids from the C-terminus;
wherein
$X^3$ is selected from the group consisting of:

$$-NH-CH[(CH_2)_n-O-R^3]-C(O)-;\text{ and}\quad\quad (i)$$

$$-NH-CH[(CH_2)_p-NH-R^6]-C(O)-;\quad\quad (ii)$$

wherein
$R^3$ is a $C_{1-35}$-alkyl or $C_{1-35}$-alkenyl group;
$R^6$ is a $C_{1-35}$-acyl group; and
n and p are integers 1, 2, 3, 4 or 5; and
when present
$X^{10}$ is selected from Gln and Ser;
$X^{11}$ is selected from Arg and Lys;

X¹² is selected from Val, Ala, Thr and Leu;
X¹³ is selected from Gln and Ser;
X¹⁴ is selected from Gln and Ser, or is absent;
X¹⁶ is Lys;
X¹⁹ is Lys;
X²⁰ is Lys;
X²⁴ is Lys;
X²⁶ is selected from Gln and Ser; and
X²⁸ is Arg;
or a pharmaceutically acceptable salt thereof.

5. The compound according to claim 1, wherein
Z is an amino acid sequence having the formula Id:

Pro-Ser-X³-Phe-Leu-Ser-Pro-Glu-His-X¹⁰-X¹¹-Val-
X¹³-X¹⁴-Arg-X¹⁶-Glu-Ser-X¹⁹-Ser-Pro-Pro-Ala-
X²⁴-Leu-X²⁶-Pro-X²⁸     (Id) (SEQ ID NO: 5)

or is a truncated form thereof lacking from 1 to 23 amino acids from the C-terminus;
wherein
X³ is —NH—CH[(CH₂)$_n$—O—R³]—C(O)—
wherein
R³ is a $C_{1-35}$-alkyl or $C_{1-35}$-alkenyl group and n is an integer 1, 2, 3, 4 or 5; and
when present
X¹⁰ is selected from Gln and Ser;
X¹¹ is selected from Arg and Lys;
X¹³ is selected from Gln and Ser;
X¹⁴ is selected from Gln and Ser, or is absent;
X¹⁶ is Lys;
X¹⁹ is Lys;
X²⁴ is Lys;
X²⁶ is selected from Gln and Ser; and
X²⁸ is Arg;
or a pharmaceutically acceptable salt thereof.

6. The compound according to claim 1, wherein
Z is an amino acid sequence having the formula Id:

Pro-Ser-X³-Phe-Leu-Ser-Pro-Glu-His-X¹⁰-X¹¹-Val-
X¹³-X¹⁴-Arg-X¹⁶-Glu-Ser-X¹⁹-Ser-Pro-Pro-Ala-
X²⁴-Leu-X²⁶-Pro-X²⁸     (Id) (SEQ ID NO: 5)

or is a truncated form thereof lacking from 1 to 23 amino acids from the C-terminus;
wherein
X³—NH—CH[(CH₂)$_p$—NH—R⁶]—C(O)—
wherein
R⁶ is a $C_{1-35}$-acyl group and p is an integer 1, 2, 3, 4 or 5; and
when present
X¹⁰ is selected from Gln, Glu and Ser;
X¹¹ is selected from Arg and Lys;
X¹³ is selected from Gln and Ser;
X¹⁴ is selected from Gln and Ser, or is absent;
X¹⁶ is Lys;
X¹⁹ is Lys;
X²⁴ is Lys;
X²⁶ is selected from Gln and Ser; and
X²⁸ is Arg;
or a pharmaceutically acceptable salt thereof.

7. The compound according to claim 1, wherein R³ is a $C_{5-16}$-alkyl or $C_{5-16}$-alkenyl group, or a pharmaceutically acceptable salt thereof.

8. The compound according to claim 1, wherein R⁴ is a $C_{7-18}$-alkyl or $C_{7-18}$-alkenyl group, or a pharmaceutically acceptable salt thereof.

9. The compound according to claim 1, wherein R⁵ is a $C_{5-16}$-acyl group, or a pharmaceutically acceptable salt thereof.

10. The compound according to claim 1, wherein R⁶ is a $C_{5-16}$-acyl group, or a pharmaceutically acceptable salt thereof.

11. The compound according to claim 1, wherein n, m or p is 1, or a pharmaceutically acceptable salt thereof.

12. The compound according to claim 1, wherein at least positions X¹ to X¹³ and X¹⁵ to X²⁸ of Z are present, or a pharmaceutically acceptable salt thereof.

13. The compound according to claim 1, selected from the group consisting of:
H-PS-S(O-octanoyl)-FLSPEHQRVQQRKESKKPPAK-LQPR-OH (SEQ ID NO: 7);
H-PS-S(O-octyl)-FLSPEHQRVQQRKESKKPPAK-LQPR-OH (SEQ ID NO: 21);
H-PS-Dap(N-octanoyl)-FLSPEHQRVQQRKESKKP-PAKLQPR-NH₂ (SEQ ID NO: 74);
H-PS-Dap(N-octanoyl)-FLSPEHSRVSSRKESKKP-PAKLSPR-NH₂ (SEQ ID NO: 82);
H-PS-Dap(N-octanoyl)-FLSPEHQRVQQRKESKKPPA-NH₂ (SEQ ID NO: 139);
H-PS-Dap(N-octanoyl)-FLSP-NH₂ (SEQ ID NO: 155);
H-PS-Dap(N-octanoyl)-FLS-NH₂ (SEQ ID NO: 156);
H-PS-Dap(N-octanoyl)-FL-NH₂ (SEQ ID NO: 157);
H-PS-[NH—CH(n-$C_{10}H_{21}$)—C(O)]-FLSPE-HQRVQQRKES-NH₂ (SEQ ID NO: 181);
H-PS-[NH—CH(n-$C_{10}H_{21}$)—C(O)]-FLSPE-HQRVQQRKESKKPPA-NH₂ (SEQ ID NO: 176);
H-PS-S(O-octyl)-FLSPE(HQRK( )QQRKESKKPPAK-LQPR-NH₂ (SEQ ID NO:97);
H-PS-S(O-octyl)-FLSPEHE( )RVQK( )RKESKKPPAK-LQPR-NH₂ (SEQ ID NO: 98);
H-PS-Dap(N-octanoyl)-FLSPEHQRVQRKESKKPPAK-LQPR-NH₂ (SEQ ID NO: 100);
H-PS-S(O-octyl)-FLSPEHQRVQRKESKKPPAKLQPR-NH₂ (SEQ ID NO: 101);
H-PS-Dap(N-octanoyl)-FLSPK-NH₂ (SEQ ID NO: 102);
H-PS-S(O-octyl)-FLSPK-NH₂ (SEQ ID NO: 103);
H-PS-[NH—CH(n-$C_{10}H_{21}$)—C(O)]-FLSPK-NH₂ (SEQ ID NO: 104);
H-PS-Dap(N-octanoyl)-FLSPY-NH₂ (SEQ ID NO: 105);
H-PS-S(O-octyl)-FLSPEHSRVSSRKESSKPPAKLSPR-NH₂ (SEQ ID NO: 108);
H-PS-S(O-octyl)-FLSPEHSRVSSRKESKSPPAKLSPR-NH₂ (SEQ ID NO: 109);
H-PS-S(O-octyl)-FLSPEHSRVSSRKESSSPPAKLSPR-NH₂ (SEQ ID NO: 110);
H-PS-S(O-octyl)-FLSPEHSRPSSR-NH₂ (SEQ ID NO: 111);
H-PS-S(O-octyl)-FLSPEHSRVSSRPESSSPPAKLSPR-NH₂ (SEQ ID NO: 112);
H-PS-S(O-octyl)-FLSPEHSRPSSRPESSSPPAKLSPR-NH₂ (SEQ ID NO: 113);
H-PS-S(octanoyl)-FLSPEHQSVQQRKESKKPPAK-LQPR-NH₂ (SEQ ID NO: 114);
H-PS-S(octanoyl)-FLSPEHQRVQQSKESKKPPAK-LQPR-NH₂ (SEQ ID NO: 115);
H-PS-S(octanoyl)-FLSPEHQRVQQRSESKKPPAK-LQPR-NH₂ (SEQ ID NO: 116);
H-PS-S(octanoyl)-FLSPEHQRVQQRKESSKPPAK-LQPR-NH₂ (SEQ ID NO: 117);
H-PS-S(octanoyl)-FLSPEHQRVQQRKESKSPPAK-LQPR-NH₂ (SEQ ID NO: 118);
H-PS-S(octanoyl)-FLSPEHQRVQQRKESKKP-PASLQPR-NH₂ (SEQ ID NO: 119);

H-PS-S(octanoyl)-FLSPEHQRVQQRKESKKPPAK-LQPS-NH$_2$ (SEQ ID NO: 120);
H-PS-S(octanoyl)-FLSPYHQRVQQRKESKKPPAK-LQPR-NH$_2$ (SEQ ID NO: 121);
H-PS-S(octanoyl)-FLSPEHQRVQYRKESKKPPAK-LQPR-NH$_2$ (SEQ ID NO: 122);
H-PS-S(octanoyl)-FLSPEHQRVQQRKESKKPPAY-LQPR-NH$_2$ (SEQ ID NO: 123);
H-PS-S(octanoyl)-FLSPYHQRVQYRKESKKPPAY-LQPR-NH$_2$ (SEQ ID NO: 124);
H-PS-S(O-octyl)-FLSPEHQRVQQRKESKKPPAK-LQPR-NH$_2$ (SEQ ID NO: 125);
H-PS-S(O-octyl)-FLSPEHQRVQRKESKKPPAKLQPR-NH$_2$ (SEQ ID NO: 126);
H-PS-S(O-octyl)-FLSPEHQRVQQRKESKKPPA-NH$_2$ (SEQ ID NO: 127);
H-PS-S(O-octyl)-FLSPEHQRVQQRKES-NH$_2$ (SEQ ID NO: 128);
H-PS-[NH—CH(n-C$_{10}$H$_{21}$)—C(O)]-FLSPEHQRVQQRKESKKPPAKLQPR-NH$_2$ (SEQ ID NO: 129);
H-PS-[NH—CH(n-C$_{10}$H$_{21}$)—C(O)]-FLSPEHQRVQRKESKKPPAKLQPR-NH$_2$ (SEQ ID NO: 130);
H-PS-S(O-octyl)-FLSPEHSR-NH$_2$ (SEQ ID NO: 132);
H-PS-S(O-octyl)-FLSPEHSRVSSR-NH$_2$ (SEQ ID NO: 133); and
H-PS-S(O-octyl)-FLSPEHSRVSSRKESKKPPAKLSPR-NH$_2$ (SEQ ID NO: 134);
or a pharmaceutically acceptable salt thereof;
wherein parentheses indicate an intramolecular bridge between a Lys and Glu residue.

14. The compound according to claim 1, wherein the compound has at least one biological activity of native human ghrelin.

15. A pharmaceutical composition comprising a compound of claim 1, or a pharmaceutically acceptable salt thereof, and a pharmaceutically acceptable carrier.

16. A method for:
(i) treating cachexia, low body weight, loss of body weight, low or decreased appetite, inability to gain weight due to gastrectomy or vagectomy, gut barrier dysfunction, inflammatory bowel disease (IBD), Crohn's disease, colitis, ulcerative colitis, or ischemia reperfusion injury;
(ii) increasing food intake and/or body weight;
(iii) inducing the production of growth hormone; or
(iv) inducing increased motility of the gastrointestinal tract;
the method comprising the step of administering to a subject in need thereof a therapeutically effective amount of a compound of claim 1, or a pharmaceutically acceptable salt thereof.

* * * * *